US012806234B2

(12) United States Patent
Spragg

(10) Patent No.: US 12,806,234 B2
(45) Date of Patent: Nov. 24, 2026

(54) JELLYFISH COLLAGEN USE

(71) Applicant: JELLAGEN LIMITED, Cardiff (GB)

(72) Inventor: Andrew Mearns Spragg, Stirling (GB)

(73) Assignee: JELLAGEN LIMITED, Cardiff (GB)

( * ) Notice: Subject to any disclaimer, the term of this patent is extended or adjusted under 35 U.S.C. 154(b) by 660 days.

(21) Appl. No.: 17/917,545

(22) PCT Filed: Apr. 7, 2021

(86) PCT No.: PCT/GB2021/050856
§ 371 (c)(1),
(2) Date: Oct. 6, 2022

(87) PCT Pub. No.: WO2021/205167
PCT Pub. Date: Oct. 14, 2021

(65) Prior Publication Data

US 2023/0148082 A1 May 11, 2023

(30) Foreign Application Priority Data

Apr. 7, 2020 (GB) ..................................... 2005141

(51) Int. Cl.
*A61K 35/614* (2015.01)
*A61K 45/06* (2006.01)
*A61P 17/02* (2006.01)

(52) U.S. Cl.
CPC ............ *A61K 35/614* (2013.01); *A61K 45/06* (2013.01); *A61P 17/02* (2018.01)

(58) Field of Classification Search
None
See application file for complete search history.

(56) References Cited

U.S. PATENT DOCUMENTS

| | | | |
|---|---|---|---|
| 2008/0234195 | A1 | 9/2008 | Long et al. |
| 2008/0249486 | A1 | 10/2008 | Effing |
| 2018/0118809 | A1 | 5/2018 | Mearns Spragg |
| 2019/0216972 | A1 | 7/2019 | Spragg |
| 2019/0388586 | A1 | 12/2019 | Qiu et al. |

FOREIGN PATENT DOCUMENTS

| | | | | |
|---|---|---|---|---|
| CN | 104906624 | * | 9/2015 | |
| JP | 2001-506908 | A | 5/2001 | |
| JP | 2002-528407 | A | 9/2002 | |
| JP | 2009-519917 | A | 5/2009 | |
| JP | 2011-509734 | A | 3/2011 | |
| JP | 2018-512441 | A | 5/2018 | |
| KR | 2006-0091350 | A | 8/2006 | |
| KR | 2020/0029363 | | 3/2020 | |
| WO | WO 98/28013 | A2 | 7/1998 | |
| WO | WO 00/24378 | A1 | 5/2000 | |
| WO | WO 2009/090655 | | 7/2009 | |
| WO | WO 2016/166524 | | 10/2016 | |
| WO | WO-2018046920 | A1 * | 3/2018 | ............. A61L 27/52 |
| WO | WO 2018/060994 | | 4/2018 | |
| WO | WO 2019/211854 | A1 | 11/2019 | |

OTHER PUBLICATIONS

Kallis, P. J. et al., "Collagen Powder in Wound Healing," *Journal of Drugs in Dermatology*, 17.4 (2018): 1-6.
Di Lullo et al., "Mapping the Ligand-binding Sites and Disease-associated Mutations on the Most Abundant Protein in the Human, Type I Collagen", *The Journal of Biological Chemistry*, 277(6):4223-4231, 2002.
Fernández-Cervantes et al., "Cell-free scaffold from jellyfish *Cassiopea andromeda* (Cnidaria; Scyphozoa) for skin tissue engineering", *Materials Science & Engineering C*, 111:110748, 2020.
Jellagen—"Jellyfish collagen biomaterials" website extract from www.mediwales.com, at Feb. 11, 2016.
Song et al., "Collagen scaffolds derived from a marine source and their biocompatibility", *Biomaterial*, 27:2951-2961, 2006.
Yasui et al., "Dual-Site Recognition of Different Extracellular matrix components by Anti-Angiogenic/Neurotrophic Serpin, PEDF", *Biochemistry*, 42:3160-3167, 2003.
Zecherle et al., "The C-terminal domain of *Escherichia coli* ribosomal protein L7/L12 can occupy a location near the factor-binding domain of the 50S subunit as shown by cross- linking with N-[4-(p-azidosalicylamido)butyl]-3-(2'-pyridyldithio)propionamide", *Biochemistry*, 31:9526-9532, 1992.
Cheng, X. et al., "Isolation, Characterization and Evaluation of Collagen from Jellyfish *Rhopilema esculentum* Kishinouye for use in Hemostatic Applications," *PLoS One*, 12.1 (2017): e0169731, 1-21.
Felician, F. F. et al., "The wound healing potential of collagen peptides derived from the jellyfish *Rhopilema esculentum*," *Chinese Journal of Traumatology*, 22 (2019): 12-20.
Widdowson, J. P. et al., "In vivo comparison of jellyfish and bovine collagen sponges as prototype medical devices," *Journal of Biomedical Materials Research B: Applied Biomaterials*, 106B.4 (2018): 1524-15.

* cited by examiner

*Primary Examiner* — Michael V Meller
(74) *Attorney, Agent, or Firm* — pH IP Law

(57) ABSTRACT

The present invention relates to the use of jellyfish collagen in the treatment of wounds and the manufacture of said jellyfish collagen.

19 Claims, 36 Drawing Sheets

JELL-01.03 - Control (film dressing only) - Group 1 500 μm

JELL-01.19 - Non-crosslinked sponge - Group 2 500 μm

JELL-01.27 -0.5% - EDC crosslinked Powder - Group 3 500 μm

JELL-01.35 - 1.0% EDC crosslinked Powder - Group 4 500 μm

JELL-01.46 - Commercial Comparator - Promogran™ - Group 5 500 μm

JELLYFISH COLLAGEN USE

This application is a national phase application under 35 U.S.C. § 371 of International Application No. PCT/GB2021/050856, filed Apr. 7, 2021, which claims the benefit of Great Britain Patent Application No. 2005141.3, filed Apr. 7, 2020, the entirety of each of which is incorporated herein by reference.

FIELD OF THE INVENTION

The present invention relates to jellyfish collagen for use in the treatment of wounds and the manufacture thereof.

BACKGROUND OF THE INVENTION

Wound healing is a complex process that involves coordinated interactions between diverse immunological and biological systems. Long-term wounds remain a challenging clinical problem, affecting approximately 6 million patients per year, with a high economic impact.

Wound healing is a process whereby the skin (or another organ-tissue) repairs itself after injury. In normal skin, the epidermis (outermost layer) and dermis (inner or deeper layer) exist in a steady-state equilibrium and shielded from the external environment. When the skin is broken, the normal (physiologic) process of wound healing begins. The classic model of wound healing comprises three or four sequential, yet overlapping, phases:

Phase 1: Haemostasis.

Phase 2: Inflammation.

Phase 3: Proliferation.

Phase 4: Remodelling.

Upon injury to the skin, a set of complex biochemical events takes place in a closely orchestrated cascade to repair the damage. Due to a number of potential stimuli (local tissue ischaemia, bioburden, necrotic tissue, repeated trauma, etc.), wounds can stall in the inflammatory phase contributing to the chronicity of the wound. One key component of chronic wounds is an elevated level of matrix metalloproteinases (MMPs). At elevated levels, MMPs not only degrade nonviable collagen but also viable collagen. In addition, fibroblasts in a chronic wound may not secrete tissue inhibitors of MMPs (TIMPs) at an adequate level to control the activity of MMPs. These events prevent the formation of the scaffold needed for cell migration and ultimately prevent the formation of the extracellular matrix (ECM) and granulation tissue. In the case of chronic wounds including diabetic foot ulcers, a combination of the associated chronic microbial infection and inflammation can lead to blood capillary degradation (reduced blood flow) and amputation. Thus, new medicaments targeting diabetic foot ulcers (DFU) may advantageously provide the ability to stimulate blood flow to the affected region and promote wound healing.

Collagen-based wound dressings have been shown to be uniquely suited to address the issue of elevated levels of MMPs by acting as a 'sacrificial substrate' in the wound. It has also been demonstrated that collagen breakdown products are chemotactic for a variety of cell types required for the formation of granulation tissue. In addition, collagen based dressings have the ability to absorb wound exudates and maintain a moist wound environment.

A number of different collagen dressings are available, which employ a variety of carriers/combining agents such as gels, pastes, polymers, oxidized regenerated cellulose (ORC), and ethylene diamine tetraacetic acid (EDTA). The collagen within these products tends to be derived from bovine, porcine, equine, or avian sources, which is purified in order to render it nonantigenic. However, there are a number of disadvantages associated with the use of these collagen types, including poor angiogenic properties, enhanced risk of disease and virus transmission, and the considerable cost associated with obtaining these collagens.

Accordingly, a source of collagen which would be suitable for use in the treatment of wounds, without displaying the disadvantages above, would be particularly advantageous.

SUMMARY OF THE INVENTION

The present invention relates to a jellyfish collagen for use in the treatment of a wound. As will be evident from the in vivo and in vitro data presented below, the inventors have surprisingly found that compositions comprising jellyfish collagen are useful in the treatment of wounds as an alternative to mammalian collagens (for example, bovine), whilst displaying equivalent results and providing a number of superior qualities, such as angiogenic properties, increased stability, low immunogenicity and a lower risk of virus transfer and disease/prion transmission. This is an entirely unexpected finding given the vastly different physicochemical and amino acid properties of jellyfish collagen compared to mammalian collagen.

Accordingly, a first aspect of the invention relates to a composition for use in the treatment of a wound, wherein the composition comprises jellyfish collagen.

A second aspect of the invention relates to a method of manufacturing the aforementioned jellyfish collagen, comprising at least the steps of:

i) extracting acid soluble collagen from a jellyfish collagen source; and ii) purifying said jellyfish collagen to provide a solution of purified jellyfish collagen.

DESCRIPTION OF THE FIGURES

Embodiments of the present invention will now be described, by way of example only, with reference to the accompanying figures, in which.

DETAILED DESCRIPTION OF THE INVENTION

Figure 1:
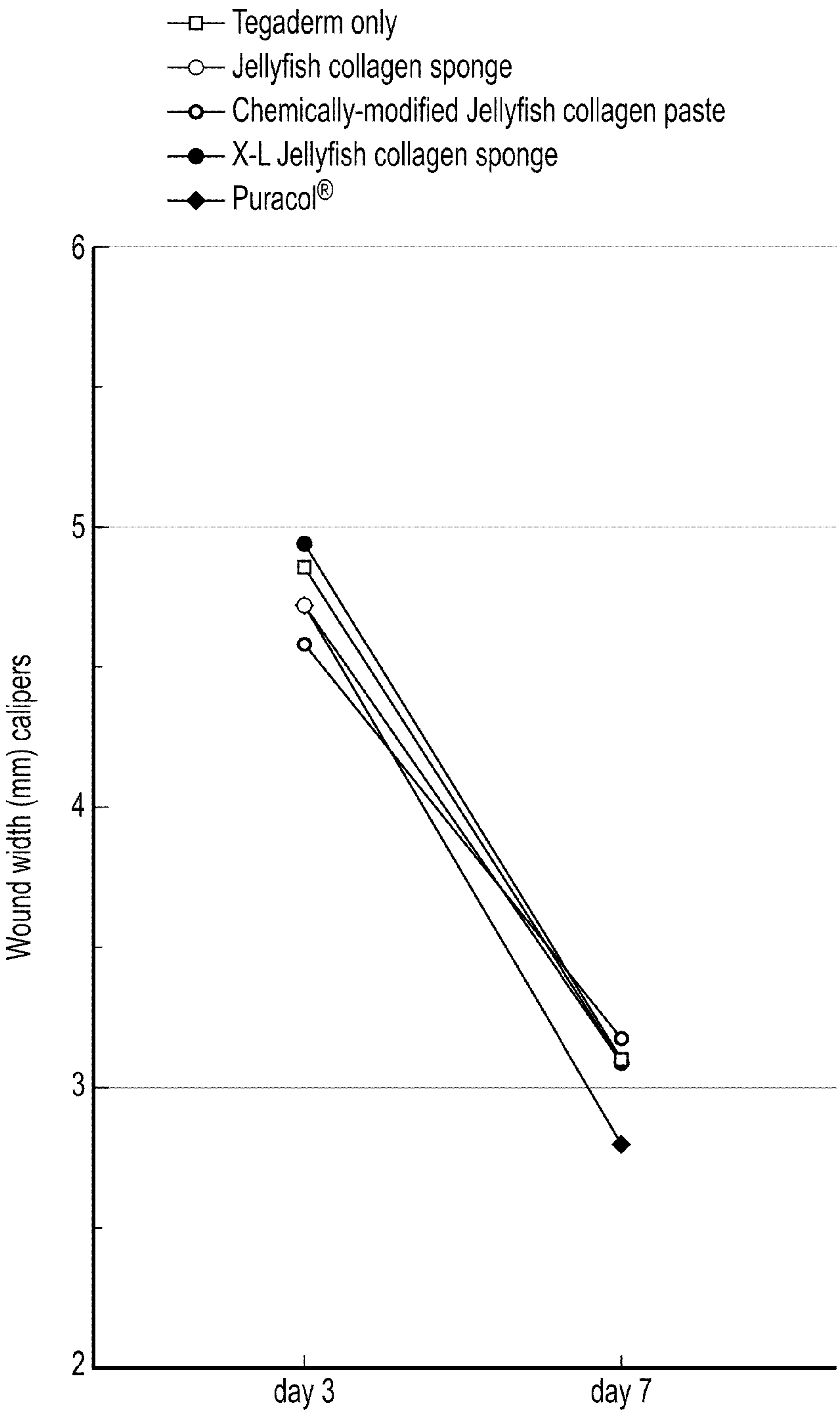
FIG. 1 shows the change in group mean width (mm) from day 3 to day 7, determined by caliper measurement.

In the following detailed description, numerous specific details are set forth in order to provide a thorough understanding of the present invention. It will be understood by those of ordinary skill in the art that embodiments of the present invention may be practiced without these specific details while still remaining within the scope of the claims.

In a first aspect, the present invention provides for a composition for use in the treatment of a wound, wherein the composition comprises jellyfish collagen.

The phrase 'treatment of a wound' or the term 'wound treatment' refers to any treatment which aids the complex process by which the skin and any associated tissues repair themselves after injury. Examples of wounds which may benefit from the use of jellyfish collagen include, but are not limited to, pressure sores, transplant sites, surgical wounds, ulcers, burns (thermal, chemical or electrical), lacerations, abrasions, punctures, avulsions, seromas and/or hematomas. In a preferred embodiment, the wound is not associated with Epidermolysis Bullosa.

In some embodiments, the jellyfish collagen is not in a hydrolysate form. By "hydrolysate form" we include the meaning of a collagen that has been degraded by heat or by protease/collagenase activity to produce collagen fragments defined as collagen peptides and gelatin-like molecules.

The jellyfish collagen for use in the treatment of a wound may be in its atelo form. By "atelo form" we include the meaning of a low-immunogenic derivative of collagen obtained by removal of N- and C-terminal telopeptide components, which are known to induce antigenicity in humans. Telopeptides are generally removed by treatment of collagen with type I pepsin.

The jellyfish collagen for use in the treatment of a wound may be in its telo form. By "telo form" we include the meaning of a collagen extracted in acid conditions producing a soluble collagen that includes telopeptides.

The jellyfish collagen for use in the treatment of a wound may be thiolated. The term 'thiolated' is intended to refer to a jellyfish collagen which has been reacted with a thiol, resulting in the introduction of a —SH group, or 'thiol' group.

The jellyfish collagen for use in the treatment of a wound may be cross-linked. In the context of the present invention, the term 'cross-linked' refers to the linkage of two independent collagen molecules via a covalent bond. Preferably, the collagen molecules to be cross-linked are in the form of collagen fibres, resulting in inter-fibril cross-linking occurring. In order to create the cross-linked thiolated jellyfish collagen, a 'cross-linking agent' or 'cross-linker' may be used. The term 'cross-linking agent' or 'cross-linker' refers to an agent that can, under certain conditions, form covalent linkages between two independent molecules. In the context of the present invention, a cross-linking agent is used to covalently link two independent collagen molecules. Preferably, the collagen molecules to be cross-linked are in the form of collagen fibres. Preferably inter-fibril cross-linking takes place. In some instances, the cross-linking agents are typically composed of two or more reactive functional groups linked together by a hydrocarbon chain. The two or more functional groups do not necessarily have to be the same. The length of the hydrocarbon chain can also be varied to control the distance between the functional groups. The exact length of the hydrocarbon chain in the context of the present invention is not intended to be limiting.

The jellyfish collagen for use in the treatment of a wound may be non-cross-linked.

The source of the jellyfish collagen may be from the sub-phylum Scyphozoa. The source of the jellyfish collagen for use in the treatment of a wound may be selected from the group consisting of: the order Rhizostomeae, including, but not limited to, *Rhizostomas pulmo, Rhopilema esculentum, Rhopilema nomadica, Stomolophus meleagris, Cassiopea* sp. (upside-down jellyfish), including but not limited to *Cassiopea andromeda*, the order Semaeostomease, including *Aurelia* sp., and other species such as *Nemopilema nomurai, Rhopilema esculentum, Rhopilema nomadica, Stomolophus meleagris*, or any combination thereof. Preferably the source of the jellyfish collagen is *Rhizostomas pulmo*. Accordingly, the collagen may comprise at least 20%, at least 30%, at least 40%, at least 50%, at least 60%, at least 70%, at least 80%, at least 90%, at least 91%, at least 92%. At least 93%, at least 94%, at least 95%, at least 96%, at least 97%, at least 98%, at least 99% *Rhizostomas pulmo* collagen.

The jellyfish collagen for use in the treatment of a wound may have a concentration of at least 1 mg/mL. It is envisaged that the maximum concentration of jellyfish collagen which may be used is 50 mg/mL. Accordingly, the concentration of jellyfish collagen may be between 1 mg/mL to 50 mg/mL, 2 mg/mL to 50 mg/mL, 3 mg/mL to 50 mg/mL, 4 mg/mL to 50 mg/mL, 5 mg/mL to 50 mg/mL, 6 mg/mL to 50 mg/mL, 7 mg/mL to 50 mg/mL, 8 mg/mL to 50 mg/mL, 9 mg/mL to 50 mg/mL, 10 mg/mL to 50 mg/mL, 11 mg/mL to 50 mg/mL, 12 mg/mL to 50 mg/mL, 13 mg/mL to 50 mg/mL, 14 mg/mL to 50 mg/mL, 15 mg/mL to 50 mg/mL, 16 mg/mL to 50 mg/mL, 17 mg/mL to 50 mg/mL, 18 mg/mL to 50 mg/mL, 19 mg/mL to 50 mg/mL, 20 mg/mL to 50 mg/mL, 25 mg/mL to 50 mg/mL, 30 mg/mL to 50 mg/mL, 35 mg/mL to 50 mg/mL, 40 mg/mL to 50 mg/mL, or 45 mg/mL to 50 mg/mL.

The jellyfish collagen for use in the treatment of a wound may be stable at a temperature at up to at least 37° C. The term 'stable' is intended to refer to the ability of the jellyfish collagen to not substantially denature under the given environmental conditions and to maintain its desirable properties. This is an advantageous property given that the intended use of the present invention involves physical contact of the product with a subject. It is envisaged that the subject is a human, however the present invention may also be utilised in the veterinary industry, for example, for use for wound treatment on dogs, cats, horses, cows, goats, sheep and the like.

The jellyfish collagen for use in the treatment of a wound may be a hydrogel, a paste, a powder, preferably a micronised powder, a membrane, a scaffold, a solution, a sponge matrix, a nano-fibre electrospun matrix, or in a lyophilised form.

A 'hydrogel' is a network of polymer chains that are hydrophilic, resulting in a highly absorbent material. The term 'paste' is intended to refer to a semisolid preparation, usually intended for external application to the skin. Typically, when used in a pharmaceutical setting, they consist of a fatty base (for example, petroleum jelly) and are at least 25% solid substance (for example, zinc oxide). A skilled person will recognise that the chosen form of the jellyfish collagen may depend on the specific wound to be treated. For example, a burn may require a hydrogel or fine collagen mesh formulation.

The compositions for use according to the invention may comprise additional pharmaceutically active ingredients. Additional pharmaceutically active ingredients include growth factors, anti-inflammatory agents, and antimicrobial drugs. Examples of anti-inflammatory agents may include nonsteroidal anti-inflammatory drugs (NSAIDs), such as aspirin salsalate, diflunisal, ibuprofen, ketoprofen, nabumetone, piroxicam, naproxen, diclofenac, indomethacin and sulindac. The concentration of the chosen anti-inflammatory drug is understood to be dependent on the type and severity of the wound to be treated. Examples of antimicrobial agents which may be used include, but are not limited to, nano silver, penicillin, ofloxacin, tetracycline, aminoglycosides and erythromycin. Mixtures of two or more of the aforementioned pharmaceutically active ingredients, with or without the above listed excipients and carriers, are envisaged.

In some embodiments, compositions for use according to the invention, further comprise at least one growth factor. In preferred embodiments, the at least growth factor is Platelet Rich Plasma (PRP), Epithelial Growth Factor 38 (EGF), Transforming Growth Factor-Beta (TGF-B, TGF-B2, TGF-B3), Hepatocyte Growth Factor (HGF), Keratinocyte Growth Factor (KGF), Granulocyte-Monocyte Colony Stimulating Growth Factor, Platelet Derived Growth Factor, Insulin-like Growth Factor 1 (IGF1), basic Fibroblast Growth Factor (bFGF), and/or Vascular 5 Endothelial Growth Factor (VEGF), or any combination thereof.

The compositions for use according to the invention may further comprise at least one antimicrobial compound. Preferably, the at least one antimicrobial compound is nano silver, penicillin, ofloxacin, tetracycline, aminoglycosides and erythromycin, flucloxacillin, clarithromycin, doxycycline, gentamicin, metronidazole, co-amoxiclav, co-trimoxazole (in penicillin), ceftriaxone, piperacillin with tazobactam, clindamycin, ciprofloxacin, vancomycin, teicoplanin, linezolid, and/or the standard of care antimicrobial agent, or any combination thereof.

The compositions for use in the treatment of a wound may be formulated for topical application to a wound. The term 'topical application' in the context of the present invention, is intended to refer to the application of the jellyfish collagen, to the specific site of the wound to be treated. The wounds to be treated may be present on the skin of a subject or on the mucosal membranes of a subject, for example, the interior of the mouth. The compositions for use according to the invention may be formulated for administration by any other route known in the art. For example, the compositions for use according to the invention may be formulated for administration by Negative Pressure Wound Therapy (NPWT) (also known as Vacuum Assisted Closure (VAC)), which involves the controlled application of sub-atmospheric pressure to the local wound environment using a sealed wound dressing connected to a vacuum pump.

In some embodiments, compositions for use according to the invention comprise collagen at a dose from 0.01 g/L to 200 g/L, preferably 1 g/L to 50 g/L per administration.

The compositions for use according to the invention may be formulated as a cream, bi-gel, ointment, mask, serum, milk, lotion, paste, foam, aerosol, stick, shampoo, conditioner, patch, hydroalcoholic or oily aqueous solution, an oil-in-water or water-in-oil or multiple emulsion, an aqueous or oily gel, a liquid, pasty or solid anhydrous product, an electrospun collagen nano-fibre matrix, a membrane and/or an oil dispersion in an aqueous phase using spherules, these spherules being polymeric nanoparticles such as nanospheres and nanocapsules or lipid vesicles of ionic and/or non-ionic type, more preferably an electrospun collagen nano-fibre matrix and/or a membrane.

The composition comprising jellyfish collagen for use according to the invention may further comprise a pharmaceutically acceptable excipient and/or carrier, and/or a pharmaceutically active ingredient. The excipients and carriers may enhance stability and/or improve the biopharmaceutical profile of the pharmaceutically active ingredient or the jellyfish collagen, which may or may not have an active substance conjugated. Examples of suitable pharmaceutically acceptable excipients and carriers may include sterile water, olive oil, ethyl oleate, glycols, monosaccharides such as fructose, glucose and galactose; non-reducing disaccharides such as sucrose, lactose and trehalose; non-reducing oligosaccharides such as raffinose and melezitose; non-reducing starch derived polysaccharide products such as maltodextrins, dextrans and cyclodextrins; and non-reducing alditols such as mannitol and xylitol. Further suitable excipients include cellulose preparations such as maize starch, wheat starch, rice starch, potato starch, gelatin, gum tragacanth, and/or polyvinylpyrrolidone. Mixtures of two or more of any of the above excipients or carriers (or any other suitable equivalent) are also envisaged. It is understood that any other substance with a similar effect would also be suitable.

In a preferred embodiment, the pharmaceutically active ingredient may be 1% lidocaine. Lidocaine, or lidocaine hydrochloride, is an anaesthetic, commonly used as a numbing agent. The lidocaine may be up to 5% lidocaine, for example between 0.1% and 5% lidocaine, 0.5% and 5% lidocaine, 1% and 5% lidocaine, 1.5% and 5% lidocaine, 2% and 5% lidocaine, 2.5% and 5% lidocaine, 3% and 5% lidocaine, 3.5% and 5% lidocaine, 4% and 5% lidocaine and 4.5% and 5% lidocaine. Preferably, the lidocaine is at a concentration of 0.1 to 2%. Examples of further anaesthetics which would be appropriate for the same purpose include, but are not limited to, benzocaine, butamben, dibucaine, lidocaine, oxybuprocaine, pramoxine, proparacaine, proxymetacaine and tetracaine.

The compositions for use according to the invention may be used to treat a wound selected from the list consisting of: a pressure sore, a transplant site, a surgical wound, an ulcer, preferably a diabetic ulcer, a thermal burn, a chemical burn, an electrical burn, a laceration, an abrasion, a puncture, an avulsion, a seroma, and/or a hematoma.

It is envisaged that the present invention may be constitute at least part of a wound dressing, with or without the additional presence of the aforementioned pharmaceutical agents. The wound dressing may contain additional ingredients, such as alginates and cellulose derivatives that can enhance absorbency, flexibility, and comfort, and help maintain an environment conducive to healing.

In one embodiment, compositions for use according to the invention may comprise jellyfish collagen in the form of micronised powder. Preferably, the micronised powder has a particle size of 1 μm to 1000 μm, more preferably, the micronised powder has a particle size of 200 μm to 500 μm.

In a particular embodiment, compositions for use according to the invention may comprise jellyfish collagen in the form of a collagen 3D sponge scaffold.

In some embodiments, compositions for use according to invention promote improved angiogenesis in a treated wound. Preferably, the improved angiogenesis is relative to an untreated wound and/or a wound treated with bovine collagen.

In a second aspect of the present invention, a method of manufacturing the aforementioned jellyfish collagen, comprising at least the steps of:

i) extracting acid soluble collagen from a jellyfish collagen source; and ii) purifying said jellyfish collagen to provide a solution of purified jellyfish collagen.

A 'solution of purified jellyfish collagen' refers to a solution of isolated jellyfish collagen that is substantially monomeric or, alternatively, substantially free from collagen fibrils. In this context, 'substantially free' refers to a solution of collagen with less than 2 wt % of the collagen being composed of fibrils. In order to maintain a collagen solution under these conditions, the isolated collagen can be stored under conditions which disfavour collagen fibril formation. This may mean the collagen is stored under acidic conditions, wherein acidic means any solution with a pH of from pH 1 to pH 6.5, or alternatively under basic conditions, wherein basic means any solution with a pH of from pH 8 to pH 14. By way of non-limiting example, the collagen may be stored in a 0.1 M solution of weak acid. The weak acid may be acetic acid or hydrochloric acid. The concentration of collagen in the collagen solution may be in the range of from 0.1 mg/ml to 30 mg/ml. Preferably, the concentration of the collagen solution is from 1 mg/ml to 10 mg/ml.

There are multiple methods for 'isolating', or 'purifying', jellyfish collagen from the anatomical milieu. Many of these will be well known and routine to the skilled person. For example, collagen can be purified from jellyfish by acid extraction, whereby different anatomical parts of the jellyfish are bathed in an acidic solution. 'Bathing', or 'bathed', refers to the process of incubating the jellyfish in the acid solution for a sufficient amount of time in order to liberate the collagen molecule. An alternative method of collagen purification is enzyme extraction, whereby the jellyfish is incubated with at least one proteolytic enzyme for a sufficient amount of time and under conditions that favour the degradation of the anatomical milieu in order to liberate the collagen molecule. The exact temperature, pH and incubation time of the enzyme extraction method will vary depending on the proteolytic enzyme used. The most suitable conditions will be well known to the skilled artisan. By way of non-limiting example, the enzyme pepsin can be incubated with jellyfish under acidic conditions in order to liberate the collagen molecule. It is envisaged that any enzyme can be used in the enzyme extraction method, and the above examples are intended to be in no way limiting.

The collagen can then be further isolated, or purified, from the undesired contaminants of the acid or enzyme extraction method by a number of different means. For example, insoluble contaminants can be removed by centrifugation. If a more pure source of collagen is required, the isolated collagen can be subjected to gel filtration, or an alternative chromatographic method that would enable the purification of the collagen molecule for other soluble contaminants of the extraction process. The exact method of further purification is not particularly limiting. Any method well known and routinely used by a protein biochemist could be adapted for the purpose of obtaining purified, or isolated, jellyfish collagen. This step can also enable the transfer of the jellyfish collagen into the desired storage buffer in order to obtain the desired solution of purified jellyfish collagen. This can be achieved by first equilibrating the chromatographic apparatus with the desired storage buffer before purification. There exist many alternative, well known methods that could be used for this purpose. Preferably, the collagen solution used in the invention is from 70% to 99% pure, wherein pure refers to the % wt in solution attributable to the collagen molecule. More preferably, the collagen solution is at least 95%, 96%, 97%, 98%, or 99% pure.

In some embodiments, the methods of manufacturing further comprise the step of:

iii). adding a cross-linking agent to form a cross-linked jellyfish collagen.

In some embodiments, the cross-linking agent is EDC, Genipin, or Poly ethenylene glycol (PEG). Preferably, the cross-linking agent is EDC. The EDC may be at a concentration of 0.01% to 5%, 0.05% to 5%, 0.1% to 5%, 0.2% to 5%, 0.3% to 5%, 0.4% to 5%, 0.5% to 5%, 0.6% to 5%, 0.7% to 5%, 0.8% to 5%, 0.9% to 5%, 1% to 5%, 1.5% to 5%, 2% to 5%, 3% to 5%, 3.5% to 5%, 4% to 5%, or 4.5% to 5%. Preferably, the concentration of EDC is 0.5% to 1%.

In some embodiments, the methods of manufacturing the jellyfish collagen further comprise digesting the extracted jellyfish collagen with a peptidase to provide an atelo jellyfish collagen. Preferably, in the step of digesting the collagen with a peptidase, the peptidase is a pepsin. The pepsin may be of mammalian origin, non-mammalian origin (for example, papain), or microbial origin. In some embodiments, the step of digesting the collagen with a peptidase is after the step of extraction and before the purification step The method of manufacturing the jellyfish collagen described above may further comprise the steps: i) providing a jellyfish collagen comprising a S—S bond; and ii) introducing a —SH group in said jellyfish collagen comprising a S—S bond by reduction of the S—S bond to provide a collagen thiol comprising a —SH group.

In order for the jellyfish collagen to comprise a-SH group, the jellyfish collagen must first comprise a S—S bond, or a 'disulphide' group. Naturally occurring collagen does not typically comprise a S—S bond. Disulphide groups may be incorporated into collagen by a number of routes. The jellyfish collagen comprising a S—S bond may be obtainable by the jellyfish collagen having one or both lysine and hydroxylysine residues. Collagen is formed of a triple-helix of polypeptide chains, one or more of which commonly comprise one or both of lysine and hydroxylysine residues. Lysine and hydroxylysine are a-amino acids having a-amino groups. As used herein, the term 'residue' refers to the portion of a chemical compound remaining after incorporation into, for instance by chemical reaction and bond formation, another substance. Thus, amino acid 'residue' refers to the polymerised form of an amino acid monomer present in a polypeptide. Although 4-5 times less plentiful in collagen than lysine residue, hydroxylysine residue is also present in amounts sufficient to be of use in the method disclosed herein. Thus, a collagen comprising a lysine or hydroxylysine residue, prior to treatment as described herein, may comprise a residue of formula (XI):

(XI)

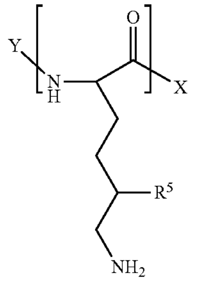

in which $R^5$ is H or OH. When $R^5$ is H a lysine residue is present. When $R^5$ is OH a hydroxylysine residue is present; and X is selected from the group OH and a chemical bond and Y is selected from H and a chemical bond, with the proviso that one or both of X and Y are chemical bonds forming peptide bonds within collagen. The peptide chain forming part of the modified collagen is shown bracketed by "[ ]" in formula (XI). The residue could be in a terminal position of the peptide, for instance if one or other of X and Y is OH and H respectively. If both X and Y are peptide bonds, the lysine residue is non-terminal within the peptide chain forming part of the collagen.

The jellyfish collagen comprising one or both of lysine and hydroxylysine residues is preferably solubilised jellyfish collagen comprising one or both of lysine and hydroxylysine. The solubilisation may be achieved by pepsin digestion or acid digestion to provide pepsin solubilised jellyfish collagen comprising one or both of lysine and hydroxylysine or by acid digestion to provide acid solubilised jellyfish collagen comprising one or both of lysine and hydroxylysine.

The jellyfish collagen, such as a pepsin solubilised or acid solubilised jellyfish collagen, comprising one or both of lysine and hydroxylysine residues, can be reacted with an activated dicarboxylic acid derivative comprising a disulphide (i.e. S—S) group to provide collagen comprising a S—S bond. In this reaction, the carbonyl group of the activated dicarboxylic acid derivative can react with the ε-amino group of the lysine or hydroxylysine residues present in the jellyfish collagen to form an amide bond.

The activated dicarboxylic acid derivative is preferably a compound of the formula:

$$ZN—C(O)—R^3—C(O)—NH—R^1—S—S—R^2—NH—C(O)—R^3—C(O)—NZ \quad (I)$$

wherein $R^1$, $R^2$ and $R^3$ independently represent divalent linking groups, preferably divalent organic linking groups, more preferably divalent hydrocarbon linking groups, such as an alkanediyl group having from 1 to 6 carbon atoms or alkendiyl or alkyndiyl groups having from 2 to 6 carbon atoms. Still more preferably, $R^1$, $R^2$ and $R^3$ independently represent ethanediyl or propanediyl groups, most preferably ethanediyl i.e. —$CH_2CH_2$—. The groups $R^1$, $R^2$ and $R^3$ may independently be optionally substituted by replacing one to four hydrogen atoms with a hydroxyl group or a halogen, such as F or Cl. In a preferred embodiment, $R^1$ and $R^2$ are identical; and ZN together represent a nitrogen containing heterocyclic group, preferably a nitrogen containing heterocyclic group having 5-6 atoms in the heterocyclic ring, in which the N atom is directly bonded to the carbonyl group of the compound of formula (I) such that Z represents a divalent linking group in which the two valences are bonded to the nitrogen. The heterocyclic group may be saturated or unsaturated, such that Z may represent an alkanediyl, alkendiyl or alkyndiyl, particularly having 2 to 4 carbon atoms. Z may optionally comprise 1 or 2 heteroatoms selected from O, S and N.

More preferably, ZN is a nitrogen containing heteroaryl group having 5-6 atoms in the aryl ring of which from 1-3 atoms are heteroatoms selected from O, N and S at least 1 of which is N which is directly bonded to the carbonyl group of the compound of formula (I). Still more preferably the heteroaryl group has 5-6 atoms in the aryl ring of which 2 atoms are N. Alternatively, ZN is a nitrogen containing heterocyclic group having 5-6 atoms in the heterocyclic ring having 1 N atom which is directly bonded to the carbonyl group of the compound of formula (I) and Z is a α, ω-organodionediyl. For example, the α, ω-organodionediyl may be represented as —C(O)$R^4$C(O)— in which $R^4$ is an alkanediyl or alkendiyl having from 2 or 3 carbon atoms.

The group ZN may be optionally substituted by replacing from one to four hydrogen atoms with a hydroxyl group or a halogen, such as F, Br or Cl or by replacing two hydrogen atoms bonded to the same carbon with an oxygen atom to form a carbonyl group, wherein the latter substitution may occur once or twice.

Most preferably, the group ZN is:

1-imidazole i.e.

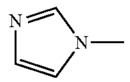

or 1-pyrrolidine-2,5-dione i.e.

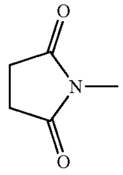

Preferred activated dicarboxylic acid derivatives may be selected from:

(II)

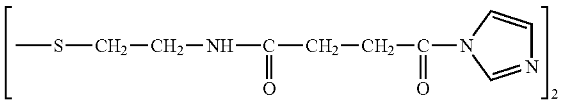

and (III)

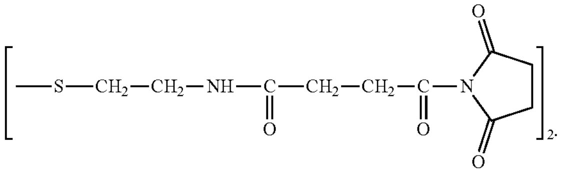

The activated dicarboxylic acid derivative (I) may be synthesised in two steps. Firstly, a diamino disulphide of formula (IV) may be reacted with at least two molar equivalents of a dicarboxylic acid anhydride of formula (V) to provide a dicarboxylic acid diamide of formula (VI):

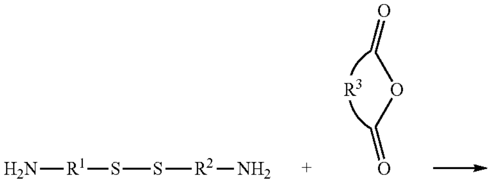

(IV) (V)

$HO-C(O)-R^3-C(O)-NH-R^1-S-S-R^2-NH-C(O)-R^3-C(O)-OH$ (VI)

in which $R^1$, $R^2$ and $R^3$ are as defined above. It will be apparent that when $R^1$ and $R^2$ are identical, the diamino disulphide of formula (IV) is a symmetrical molecule, which will result in a symmetrical activated dicarboxylic acid derivative (I).

The first reaction step may be carried out by dissolving the diamino disulphide of formula (IV) in a solvent, such as water, and adding the dicarboxylic acid anhydride of formula (V). It is preferred that the reaction is carried out under basic conditions, such that prior to the addition of the acid anhydride, a base can be added. For instance, aqueous sodium hydroxide can be added to adjust the pH to 10. After addition of the dicarboxylic acid anhydride, the pH may decrease, and it is preferred to maintain the pH in the range of from 7 to 10 during the reaction by the addition of further base. The reaction may be carried out at room temperature under stirring and may be complete within 30 minutes to 2 hours. The dicarboxylic acid diamide product of formula (VI) may be precipitated by lowering the pH, for instance to a pH of 1, by the addition of acid, such as aqueous hydrochloric acid. The precipitated dicarboxylic acid diamide (VI) can be isolated by filtration, washed with water and then dried under reduced pressure.

In the second step of the synthesis the dicarboxylic acid diamide (VI) is activated by the addition of a nitrogen containing heterocyclic compound to provide the activated dicarboxylic acid derivative (I):

$HO—C(O)—R^3—C(O)—NH—R^1—S—S—R^2—NH—C(O)—R^3—C(O)—OH(VI) \rightarrow ZN—C(O)—R^3—C(O)—NH—R^1—S—S—R^2—NH—C(O)—R^3—C(O)—NZ$ (I)

in which $R^1$, $R^2$, $R^3$ and NZ are as defined above.

In one embodiment, the nitrogen containing heterocyclic compound may be a carbodiimide, such as a compound of formula (VII):

(VII)

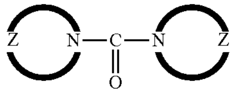

in which Z is as defined above. Preferably, ZN together are a nitrogen containing heteroaryl group having 5-6 atoms in the aryl ring of which from 1-3 atoms are heteroatoms selected from O, N and S at least 1 of which is N. The carbodiimide (VII) is more preferably 1,1'-carbonyl-diimidazole or the like.

At least 2 molar equivalents of the carbodiimide should be used per mole of dicarboxylic acid diamide (VI). Theoretically, the reaction will produce 2 molar equivalents of carbon dioxide and 2 molar equivalents of imidazole, per mole of dicarboxylic acid diamide (VI). The evolution of carbon dioxide gas indicates that the reaction is proceeding. The reaction may be carried out under reduced pressure.

In another embodiment, the nitrogen containing heterocyclic compound may be a N-hydroxy heterocyclic compound of formula (VIII):

(VIII)

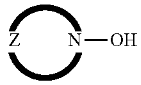

in which ZN together is a nitrogen containing heterocyclic group having 5-6 atoms in the heterocyclic ring of which 1 is N and Z is a α, ω-organodionediyl. For example, the α, ω-organodionediyl may be represented as $—C(O)R^4C(O)—$ in which $R^4$ is an alkanediyl or alkendiyl having from 2 or 3 carbon atoms. The N-hydroxy heterocyclic compound (VIII) is most preferably N-hydroxy succinimide.

The second reaction step may be carried out by dissolving the dicarboxylic acid diamide (VI) in a solvent, such as anhydrous dimethylformamide and then adding the nitrogen containing heterocyclic compound (VII) or (VIII). The activated dicarboxylic acid derivative (I) precipitates from the solution. The product can be collected by filtration, washed with anhydrous ethyl acetate, and dried under reduced pressure.

Returning to the first step of the method of the invention, a source collagen comprising one or both of lysine and hydroxylysine residues can be reacted with an activated dicarboxylic acid derivative comprising a disulphide group, such as the activated dicarboxylic acid derivative of formula (I) to provide collagen comprising a S—S bond, such as collagen of one or more of Type I, II, III, IV, V, VI, IX, X and XI comprising a S—S bond. In this reaction, a carbonyl group of the activated dicarboxylic acid derivative can react with the ε-amino group of the lysine or hydroxylysine residues present in the collagen to form an amide bond, thereby incorporating the disulphide group. The reaction can be represented by:

$ZN—C(O)—R^3—C(O)—NH—R^1—S—S—R^2—NH—C(O)—R^3—C(O)—NZ(I)$+collagen- $NH_2 \rightarrow ZN—C(O)—R^3—C(O)—NH—R^1—S—S—R^2—NH—C(O)—R^3—C(O)—NH\text{-collagen}+HNZ$ This reaction may continue to provide a cross-linked collagen when both activated carboxyl groups of the activated dicarboxylic acid derivative react with collagen, particularly different collagen triple helices or fibrils:

$ZN—C(O)—R^3—C(O)—NH—R^1—S—S—R^2—NH—C(O)—R^3—C(O)—NH\text{-collagen}+\text{collagen-}NH_2 \rightarrow \text{Collagen-}HN—C(O)—R^3—C(O)—NH—R^1—S—S—R^2—NH—C(O)—R^3—C(O)—NH\text{-collagen}+HNZ$ The reaction can be carried out by dissolving the source collagen in a solvent. The dissolution of the source collagen can be carried out in a two-step process. In the first step, the source collagen may be mixed with methanol. In the second step, a polar aprotic solvent is added. For instance, the source collagen can be added to a mixture of methanol and dimethylsulfoxide, and allowed to swell. Additional dimethylsulfoxide can be added with stirring until dissolution of the source collagen is complete. Methanol can then be removed from the solution by evaporating under reduced pressure. This solubilising process can be used with both atelocollagen and telocollagen.

The activated dicarboxylic acid derivative can then be dissolved in a solvent, particularly an anhydrous polar aprotic solvent, such as dimethylsulfoxide. Since the activated dicarboxylic acid derivative of formula (I) is sensitive to water, the reaction with collagen is preferably carried out in anhydrous polar aprotic solvents, such as dimethylsulfoxide. The activated dicarboxylic acid derivative dissolved in a solvent is then added to the source collagen solution. The carbonyl group of the activated dicarboxylic acid derivative can react with the ε-amino group of the lysine or hydroxylysine residues present in the source collagen to form an amide bond.

The mixture can be stirred at room temperature, for instance 22° C., until a gel is formed. The mixture containing the gel can then be left undisturbed e.g. for 12-18 hr. The dimethylsulfoxide can then be extracted from the gel by blending with an excess of acetone, collecting the collagen gel by decantation and then reblending with more acetone. The mixture can then be stirred e.g. for 0.5 to 1 hr and the collagen subsequently isolated by filtration, washed with acetone, then washed with water-ethanol (30:70 v/v) and dehydrated with ethanol. A jellyfish collagen comprising a S—S bond is thereby provided.

In an alternative embodiment, the jellyfish collagen comprising a S—S bond may be provided by modifying a collagen-binding protein to include a photoreactive cross-linker comprising a disulphide group, combining this with jellyfish collagen to provide a complex and irradiating the complex to cross-link the photoreactive cross-linker to incorporate the disulphide group into the collagen.

This route creates protein-binding sites on the jellyfish collagen by using a site-specific photo-cross-linking strategy allowing the creation of thiol groups in collagen. This involves the introduction of a cysteine residue into the collagen-binding protein by site-directed mutagenesis. A photoreactive cross-linker, preferably APDP, can be introduced into cysteine —SH groups on proteins. The complex of APDP-modified protein and collagen can be cross-linked by ultraviolet (uv) irradiation. The disulfide cross-link can then be cleaved by reduction, and an —SH group is generated on the jellyfish collagen.

In a first step, a collagen-binding protein comprising a cysteine residue is provided. A cysteine residue is necessary because this comprises a sulphydryl group necessary for reaction with the cross-linker. The collagen-binding protein may be, for instance, pigment epithelium-derived factor (PEDF). PEDF is a known anti-angiogenic/neurotrophic factor with a collagen binding site identified by Yasui et al as disclosed in *Biochemistry,* 2003, 42, pages 3160-3167.

If necessary, cysteine may be incorporated into the collagen-binding protein if not already present or if the collagen-binding protein does not contain sufficient cysteine. Cysteine substitutions can be made via site-directed mutagenesis, for instance where the collagen binding site is localised (F383) and on the opposite surface of the site (Y211). Methods for carrying out such site-directed mutagenesis are found in J. D. J. Biol. Chem. 2002, 277, 4223-4231 and R. R. Biochemistry 1992, 31, 9526-9532.

The sulphydryl groups introduced as a result of the cysteine substitutions can then be reacted with a photoreactive cross-linker. The photoreactive cross-linker should be bifunctional. In particular, the photoreactive cross-linker should comprise a functional group capable of reacting with a sulphydryl group to produce a disulphide bond. One such suitable functional group is a pyridyl-dithio group i.e. $C_5NH_5—S—S—$, particularly 2-pyridyl dithio. The photoreactive cross-linker should also comprise a functional group capable of cross-linking with collagen under photo-irradiation. One such suitable functional group is an azide group, particularly an aryl azide group, such as a phenyl azide, especially para $—C_6H_4—N_3$.

N-[4-(p-azidosalicylamido)butyl]-3'-(2'pyridyldithio) propionamide (APDP) is one example of a preferred photoreactive cross-linker. The disulphide group of APDP can react with the sulphydryl group of the cysteine to produce a disulphide bond between the cysteine and the photoreactive cross-linker, thereby providing a photoreactive cross-linker modified collagen binding protein comprising a S—S group. 2-pyridyl thione is liberated as part of this reaction as a leaving group.

The photoreactive cross-linker modified collagen-binding protein can then be combined with a jellyfish collagen, to provide a complex of the photoreactive cross-linker modified collagen-binding protein and the jellyfish collagen. In this step, the photoreactive cross-linker modified collagen-binding protein binds to the protein binding site of the jellyfish collagen to form the complex. The complex of the photoreactive cross-linker modified collagen-binding protein and the collagen can then be irradiated, for example with ultraviolet (UV) light. Irradiation causes the functional group capable of cross-linking present on the photoreactive cross-linker to form a covalent bond with the adjacent collagen in the complex. For example, when the functional group capable of cross-linking is a phenyl azide, irradiation at a wavelength in the range of from 250 to 280 nm will generate a nitrene, which can then attack nucleophilic or active hydrogen groups, such as C—H or $C—NH_2$ on the collagen to generate a cross-link by insertion across the C—H or N—H bond. In this way, the photoreactive cross-linker modified collagen binding protein comprising a S—S group is incorporated into the collagen to provide collagen comprising a S—S bond. It will be apparent that the disulphide group will be provided in the vicinity of the collagen protein binding site by this route.

A sulphydryl group can then be introduced into the collagen comprising a S—S bond which can be provided by either of the methods discussed above i.e. using the activated dicarboxylic acid derivate or photoreactive cross-linker methods. The jellyfish collagen comprising a S—S bond can be reacted with a suitable reducing agent. The reducing agent reduces the disulphide bond to two sulphydryl groups, thereby cleaving the activated dicarboxylic acid derivative residue or the photoreactive cross-linker residue, in which the disulphide group is located. Such a reduction proceeds by two sequential thiol-disulfide exchange reactions, resulting in the reduction of the disulphide group to produce jellyfish collagen comprising a sulphydryl (—SH) group.

Suitable reducing agents include, for example, dithiothreitol (DTT), (2S)-2-amino-1,4-dimercaptobutane (DTBA) and tris(2-carboxyethyl) phosphine HCl (TCEP hydrochloride). Dithiothreitol is a preferred reducing agent.

The reduction step can be carried out by adding the jellyfish collagen comprising a S—S bond to a buffer solution, such as a glycine/sodium hydroxide buffer solution at a pH of in the range of from 7.5 to 9.5, more preferably about 8 to 9.5, preferably about 8.0. The jellyfish collagen comprising a S—S bond may be inherently acidic, and if so, neutralisation with a base, such as sodium hydroxide, may be required.

Preferably, at least two molar equivalents of DTT reducing agent can be added per mole of disulphide group in the same buffer and the reaction allowed to proceed at 30° C. for 2-6 hr. After completion of the reaction, the pH of the liquid may be decreased to 2, for instance using HCl. The mixture may then be dialysed with dilute HCl solution, centrifuged and freeze-dried to provide the jellyfish collagen thiol having a —SH group.

The reduction may cause a slight degradation of the collagen chains. Consequently, shorter reaction times, lower pH and lower temperature can all be used to minimise any degradation.

It will be apparent that when the jellyfish collagen comprising a S—S bond is provided using a photoreactive cross-linker modified collagen-binding protein, the modified collagen-binding protein will still be attached to the collagen via the photoreactive cross-linker step d prior to the step of forming the collagen thiol. Reduction of the S—S bond will cleave the S—S bond of the photoreactive cross-linker.

When the jellyfish collagen comprises one or both of lysine and hydroxylysine residues, a jellyfish collagen thiol comprising a lysine or hydroxylysine residue of formula (X) is provided:

(X)

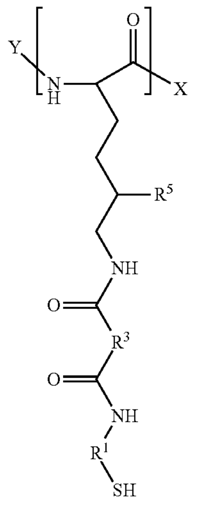

in which $R^1$, $R^3$ and $R^5$ are as defined above. For instance, $R^1$ and $R^3$ are independently selected from divalent linking groups, preferably divalent organic linking groups, more preferably divalent hydrocarbon linking groups, such as an alkanediyl group having from 1 to 6 carbon atoms or alkendiyl or alkyndiyl groups having from 2 to 6 carbon atoms. Still more preferably, $R^1$ and $R^3$ independently represent ethanediyl or propanediyl groups, most preferably ethanediyl (i.e. $—CH_2CH_2—$). $R^5$ is H when the amino acid residue is a lysine residue. $R^5$ is OH when the amino acid residue is a hydroxylysine residue; X is selected from the group OH and a chemical bond and Y is selected from H and a chemical bond, with the proviso that one or both of X and Y are chemical bonds forming peptide bonds within collagen. The peptide chain forming part of the modified collagen is shown bracketed by "[ ]" in formula (X). The residue could be in a terminal position of the peptide, for instance if one or other of X and Y is OH and H respectively. If both X and Y are peptide bonds, the lysine residue is non-terminal within the peptide chain forming part of the collagen.

The present invention further provides for a method of manufacturing the jellyfish collagen disclosed herein, which may or may not be thiolated, which further comprises the steps: i) mixing the solution of purified jellyfish collagen, or the collagen thiol, with an aqueous neutralisation buffer; and ii) incubating the mixture for a sufficient amount of time to enable collagen fibrils to form, wherein a cross-linking agent is added in either step i) or ii) to provide a cross-linked collagen.

The term 'neutralisation buffer' refers to any buffer within which a solution of purified jellyfish collagen can be diluted in order to increase or decrease the pH to a pH of from pH 4 to pH 9. The composition of the neutralisation buffer is not particularly limiting, only insofar that it must increase or decrease the pH of the solution of purified jellyfish collagen in order that collagen fibril formation can proceed. Furthermore, the buffer must be substantially free from ions, compounds, or molecules which may interfere with any cross-linking process. Thus, a buffer substantially free from unreacted amines is particularly desirable. By way of non-limiting example only, the neutralisation buffer may be of from 1× to 10× phosphate buffered saline (PBS), where 1× or 10× refer to the concentration of PBS. The composition of 1×PBS will be well known to the skilled person. The exact concentration of PBS (i.e. 1× or, e.g. 10×) will depend entirely on the dilution factor required when mixing with the solution of purified jellyfish collagen, in order that the solution of purified jellyfish collagen is substantially neutralised so that collagen fibril formation can proceed. In some embodiments, the neutralisation buffer is sodium hydroxide.

The term 'fibril formation', or 'fibrillogenesis', refers to the process by which collagen molecules undergo controlled aggregation to form higher order, well-structured macromolecular assemblies. Collagen in vivo is a predominantly extracellular protein whose aggregation into fibrillar structures provides architectural support for surrounding tissues and/or components of the extracellular matrix. The aggregation of collagens, in particular mammalian collagens, is a well-known phenomenon. Different isoforms of mammalian and marine collagens preferentially aggregate into different macromolecular structures. The unique macromolecular structures formed from each collagen isoform is governed by the physicochemical properties of the collagen polypeptide and the conditions under which fibrillogenesis is promoted. Higher-order collagen structures, i.e. collagen fibrils obtained from mammals or fish, have been exploited in vitro in order to generate mammalian and/or fish collagen hydrogels. Thus, in order to form hydrogels from jellyfish collagens, jellyfish collagens are preferred to assemble into higher order structures. Preferably, the higher order structure is a fibril.

It is envisaged that any cross-linking agent known to cross-link under the conditions within which collagen fibrils are formed would be a suitable cross-linking agent for use in the invention. In certain applications, it may be desirable to use a cross-linking agent that is non-toxic to cells. In certain embodiments, the crosslinking agent may be selected from genipin, 1,4-BDDGE, or mucochloric acid. Preferably, the cross-linking agent is either genipin or 1,4-BDDGE.

The present invention is now further described with reference to the below examples and studies.

EXAMPLES

Example 1—a Study to Determine the Effect of Jellyfish Collagen Sponge, Cross-Linked Jellyfish Collagen Sponge and Chemically-Modified (Thiolated) Jellyfish Collagen Paste in a Murine Model of Cutaneous Wound Healing Aim To compare the performance of jellyfish collagen sponge; cross-linked jellyfish collagen sponge; chemically-modified (thiolated) jellyfish collagen paste—to a commercially-available wound product, Puracol®, in a model of excisional, cutaneous wound healing in C57BL/6J mice.

Procedure

Eighty (80) male C57BL/6J mice, aged 5-6 weeks of age, were provided by Epistem in two cohorts of 40 mice each. Each cohort of mice was acclimatized for two weeks and eight mice per cohort were randomized into one of five treatment groups. On day 0 (day of wounding) all animals were anaesthetised, shaved and two 6 mm diameter excisional wounds made at the same relative position, either side of the dorsal mid-line, on each mouse. According to the assigned treatment group one of the following dressings was applied to the wound cavities of each mouse: pre-formed jellyfish collagen sponges, either standard or cross-linked; chemically-modified (thiolated) collagen gel; pre-cut Puracol® dressing; no treatment. Following application of wound treatments, a Tegaderm film dressing was applied to cover each wound. Mice were placed into a warming cabinet after the procedure and allowed to recover from anaesthesia before returning them to their holding room. All mice were housed individually from the time of wounding. Wounds were monitored at least once per day for any sign of infection and detachment of Tegaderm film dressings. Visual assessment of wound condition and measurement of wound width was not possible to perform accurately during the in-life phase of the study, due to the folding of the Tegaderm, caused by normal mouse activity.

From each cohort, four mice per treatment group were euthanised at 3 days post-wounding and four mice at 7 days post-wounding. Mice were humanely killed by cervical dislocation and the strip of dorsal skin containing both wounds was excised. Wound width was determined using digital callipers; wounds were also assigned a subjective visual score (1-5) according to the degree of macroscopic healing. Individual wounds were bisected with half snap-frozen in liquid nitrogen and half fixed in 10% neutral-buffered formalin for histological processing and preparation of Haematoxylin and Eosin (H&E)-stained transverse wound sections. For each wound section, wound width, and degree of re-epithelialisation were determined using computer-assisted morphometry (Zeiss Axiohome system). In addition, a subjective score for granulation tissue maturity was assigned to each wound, and the area of granulation tissue determined.

Results

Each treatment group demonstrated healing of excisional wounds from day 3 to day 7, as evidenced by reduced wound width (FIGS. 1 and 2), increased percentage of re-epithelialisation (FIG. 3) and increased granulation (FIG. 4) (both granulation tissue maturity and area of granulation). For the Tegaderm only control group, mean wound width decreased from (4.57±0.93) mm on day 3 to (3.71±0.92) mm on day 7 (figures quoted are mean±standard deviation).

Figure 2:
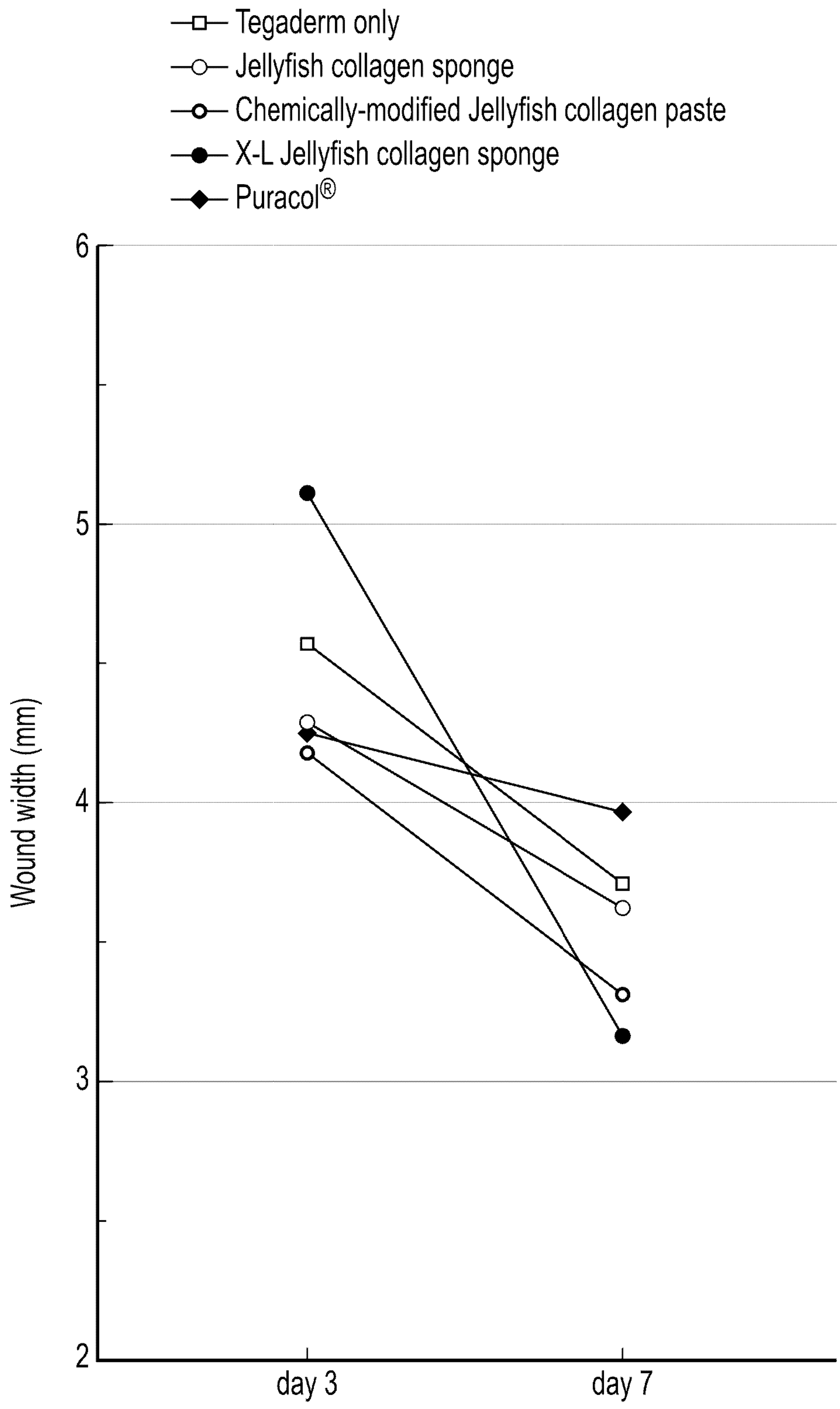
FIG. 2 shows the change in group mean width (mm) from day 3 to day 7, determined by morphometry.

The cross-linked jellyfish collagen sponge group demonstrated the greatest amount of wound closure, with a day 3 mean wound width of (5.11±1.46) mm and a day 7 value of (3.16±0.80) mm (FIG. 2). The least wound closure was observed in the Puracol® group, with a mean wound width of (3.96±1.03) mm on day 7.

Figure 3:
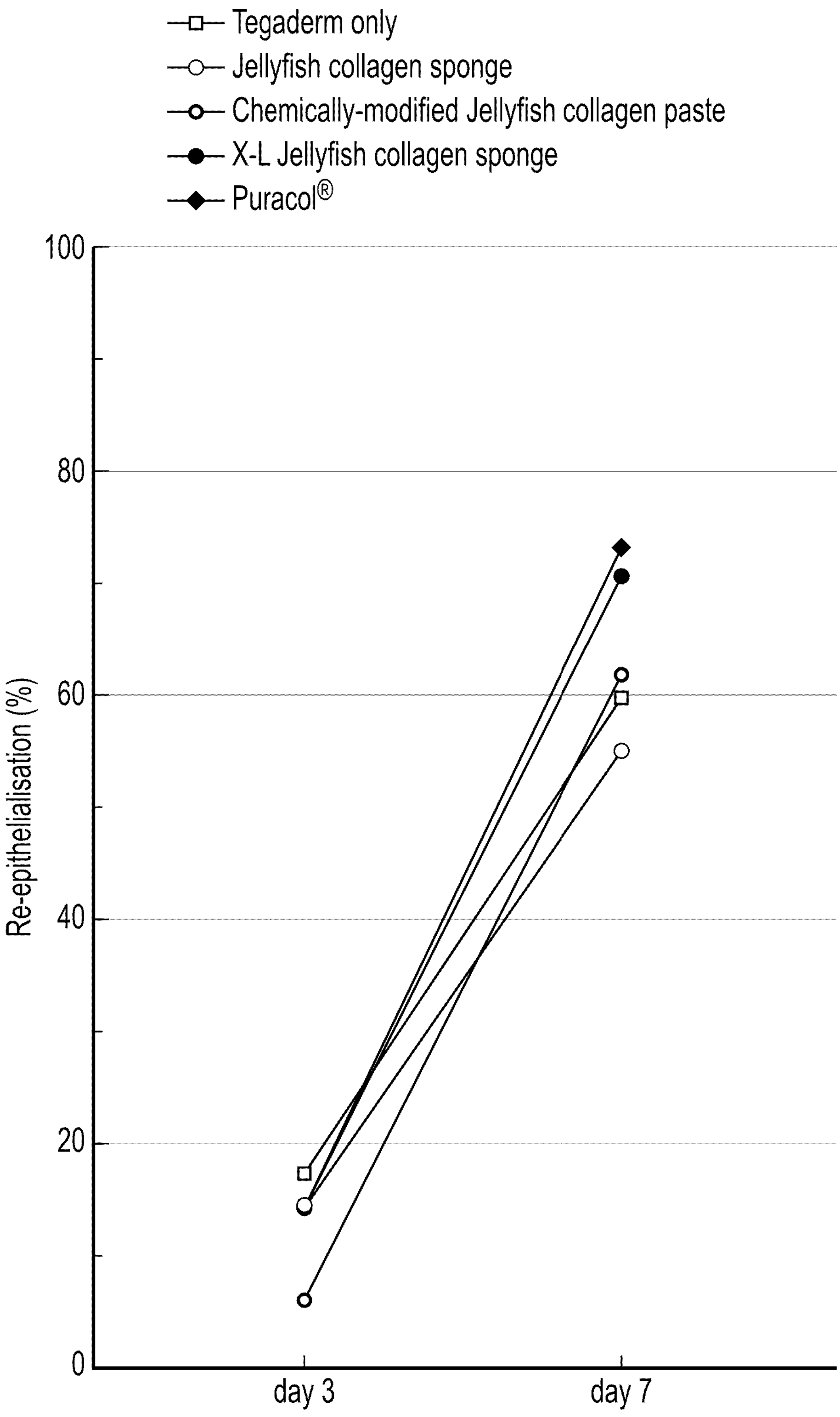
FIG. 3 shows the change in group mean re-epithelialisation (%) from day 3 to day 7.

Re-epithelialisation in the Tegaderm only group progressed from (17.2±10.5) % on day 3 to (59.7±37.9) % on day 7. The Puracol® group demonstrated the most re-epithelialisation on day 7, at (73.2±27.1) %, with the cross-linked jellyfish collagen sponge group showing a similar level of re-epithelialisation at (70.7 t 30.3) % (FIG. 3).

Figure 4:
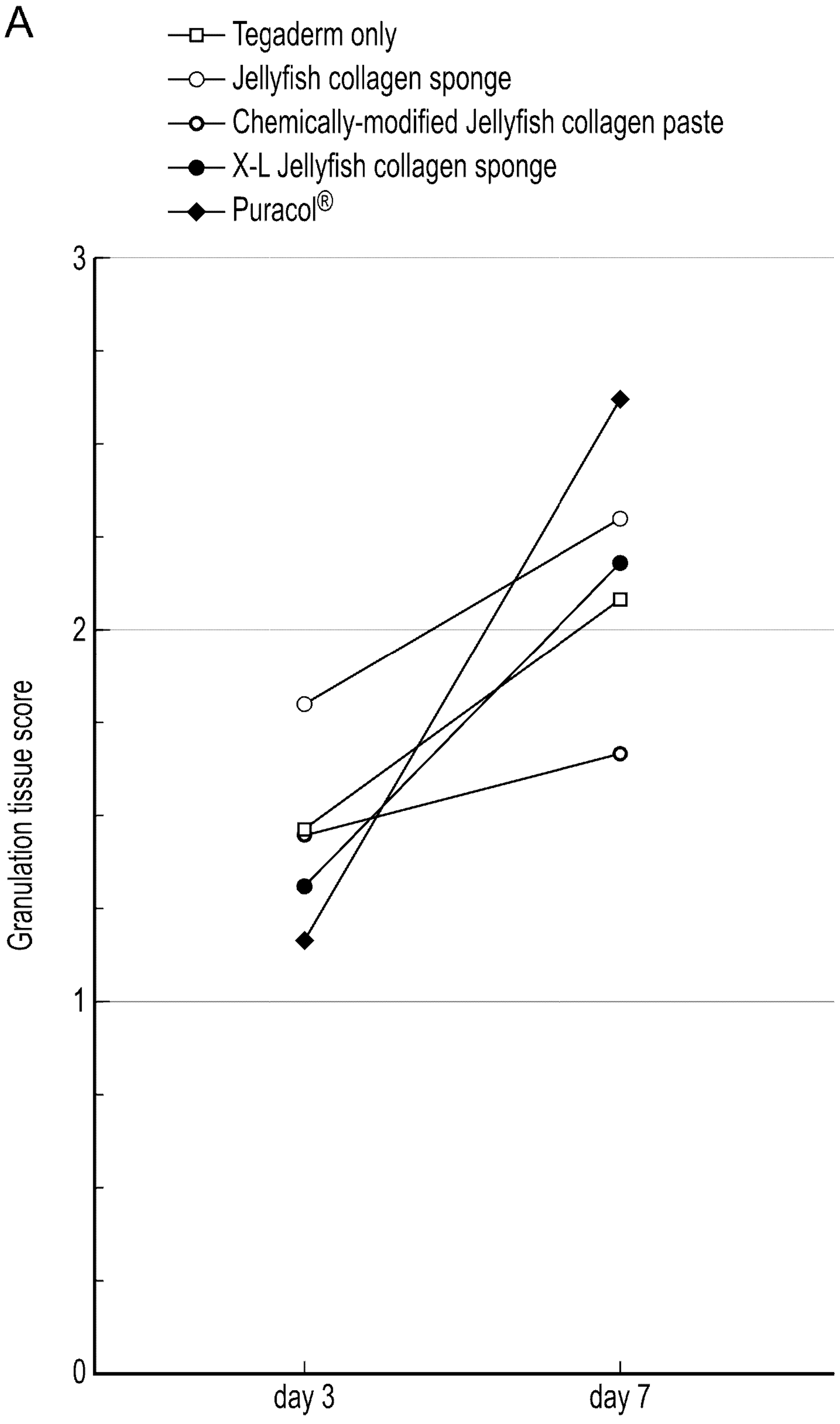
FIG. 4 shows the change in group mean tissue granulation scores (4A) and mean percentage of wound area granulation (%) (4B) from day 3 to day 7.
Figure 4:
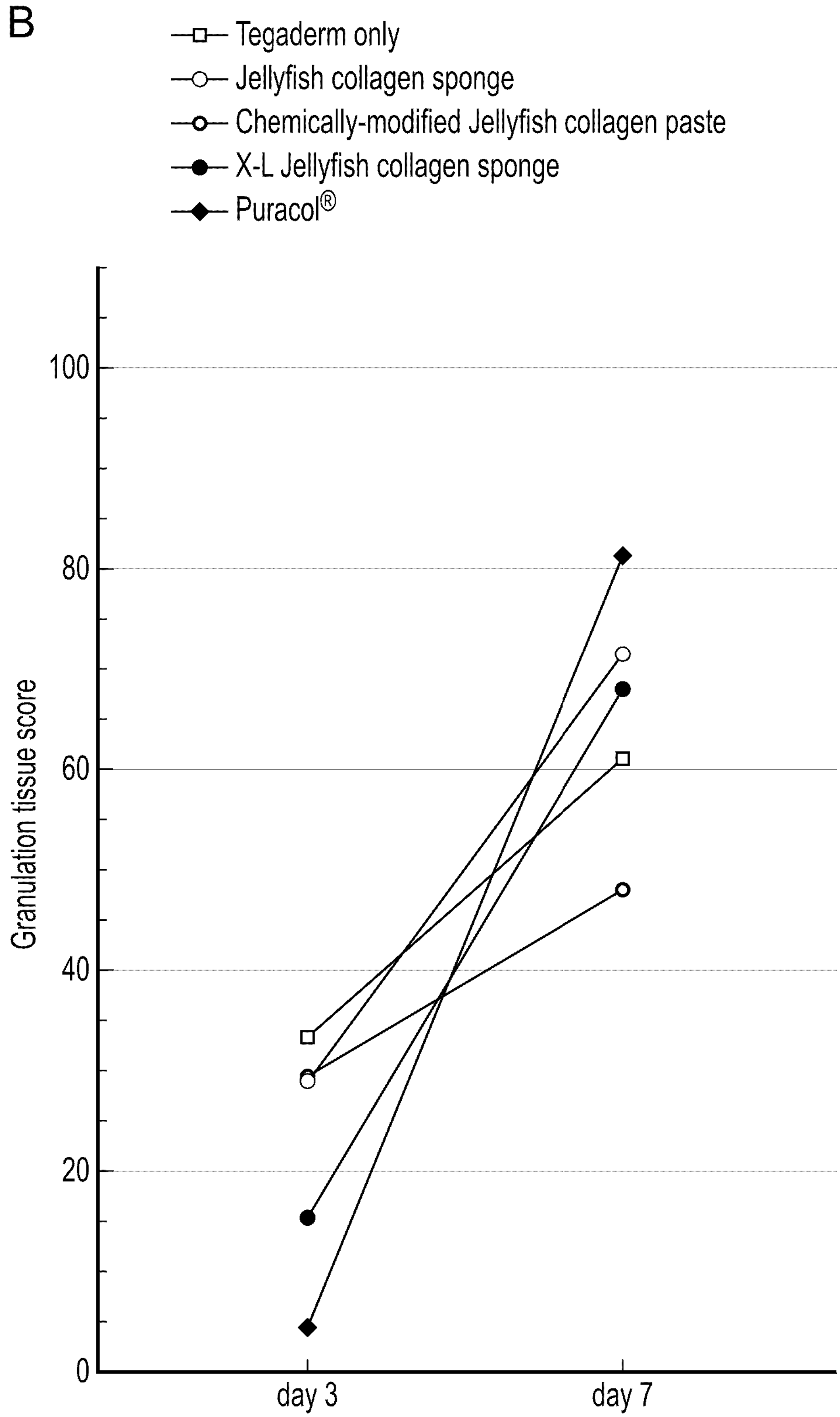

Granulation score and the area of granulation (as a percentage of total wound area) increased from day 3 to day 7 for all groups (FIG. 4). For the Tegaderm only group, the mean granulation score on day 3 was (1.46±0.52), with granulation tissue occupying (33±24) % of the wound space. By day 7, the mean granulation score for this group had increased to (2.08±0.51), with (61 t 31) % of the wound space being granulation tissue. The Puracol® group had the lowest granulation score on day 3, of (1.17±0.39), with just (5±6) % granulation tissue within the wound space; however, by day 7, this group had the highest granulation tissue score of (2.63±0.52), with (81±20) % of the wound space being granulation tissue. The jellyfish collagen sponge group and the chemically-modified (thiolated) collagen paste group showed similar amounts of granulation on day 3 to the Tegaderm only group, whereas treatment with the cross-linked jellyfish collagen sponge was associated with approximately half the amount of granulated tissue in the wound space on day 3, at only (15±21) %. The lowest mean granulation tissue score on day 7, of (1.67±0.50), was observed for the chemically-modified (thiolated) collagen paste group, with just (48±41) % of the wound space being granulation tissue. Despite differences in the proportion of the wound space showing granulation on day 3, both types of jellyfish collagen sponge were associated with similar levels of granulation on day 7, with scores of (2.30±0.82) and (2.18±0.75) for the standard and cross-linked sponges, respectively.

Figure 5:
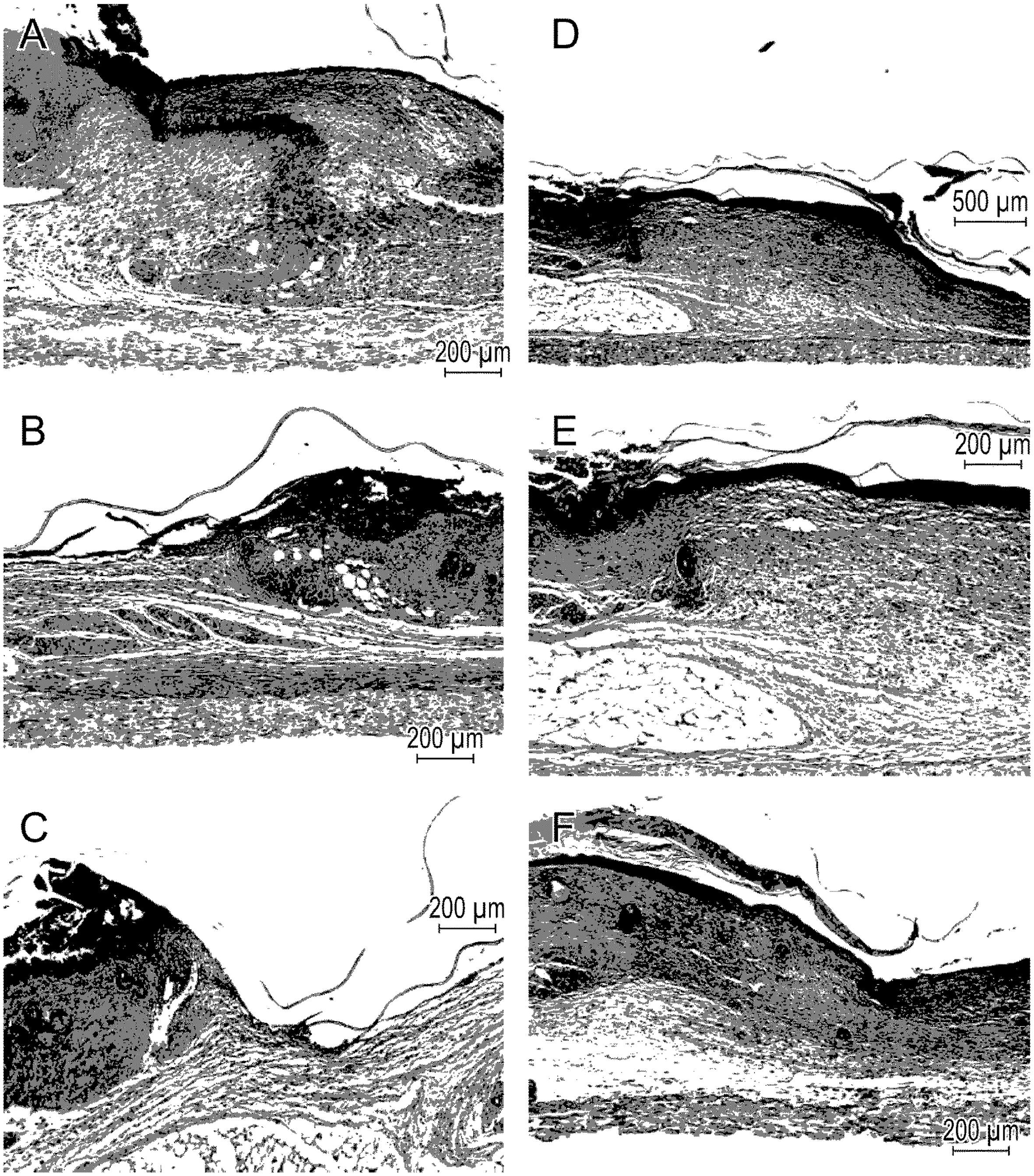
FIG. 5 shows representative images of H&E-stained wound sections from the Tegaderm only group. Panels A), B) and C) represent images from wound sections collected on day 3 and panels D), E) and f) represent images from wound section collected on day 7.
Figure 6:
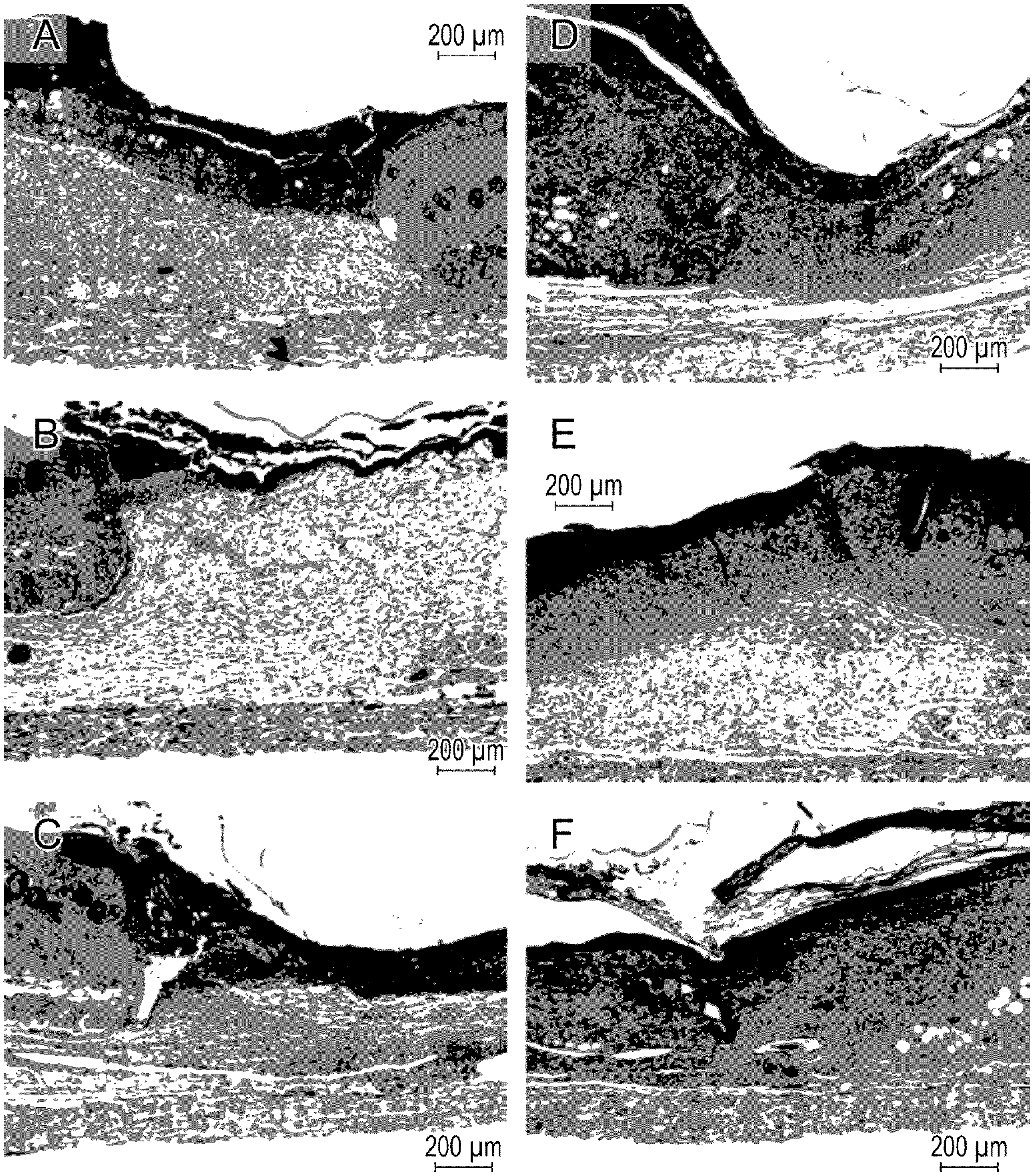
FIG. 6 shows representative images of H&E-stained wound sections from the jellyfish collagen sponge group. Panels A), B) and C) represent images from wound sections collected on day 3 and panels D), E) and f) represent images from wound section collected on day 7.
Figure 7:
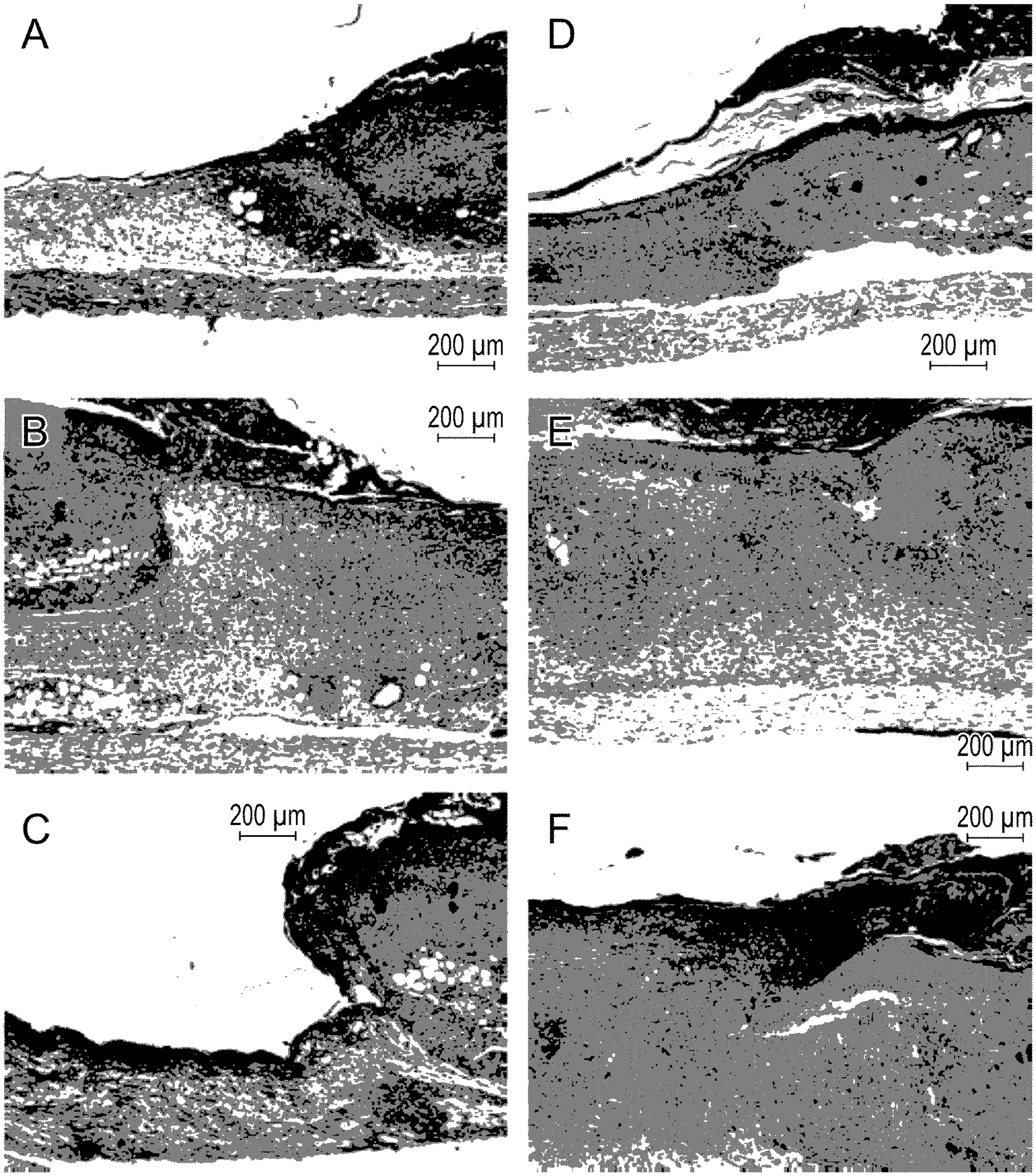
FIG. 7 shows representative images of H&E-stained wound sections from the chemically-modified (thiolated) jellyfish collagen paste group. Panels A), B) and C) represent images from wound sections collected on day 3 and panels D), E) and f) represent images from wound section collected on day 7.
Figure 8:
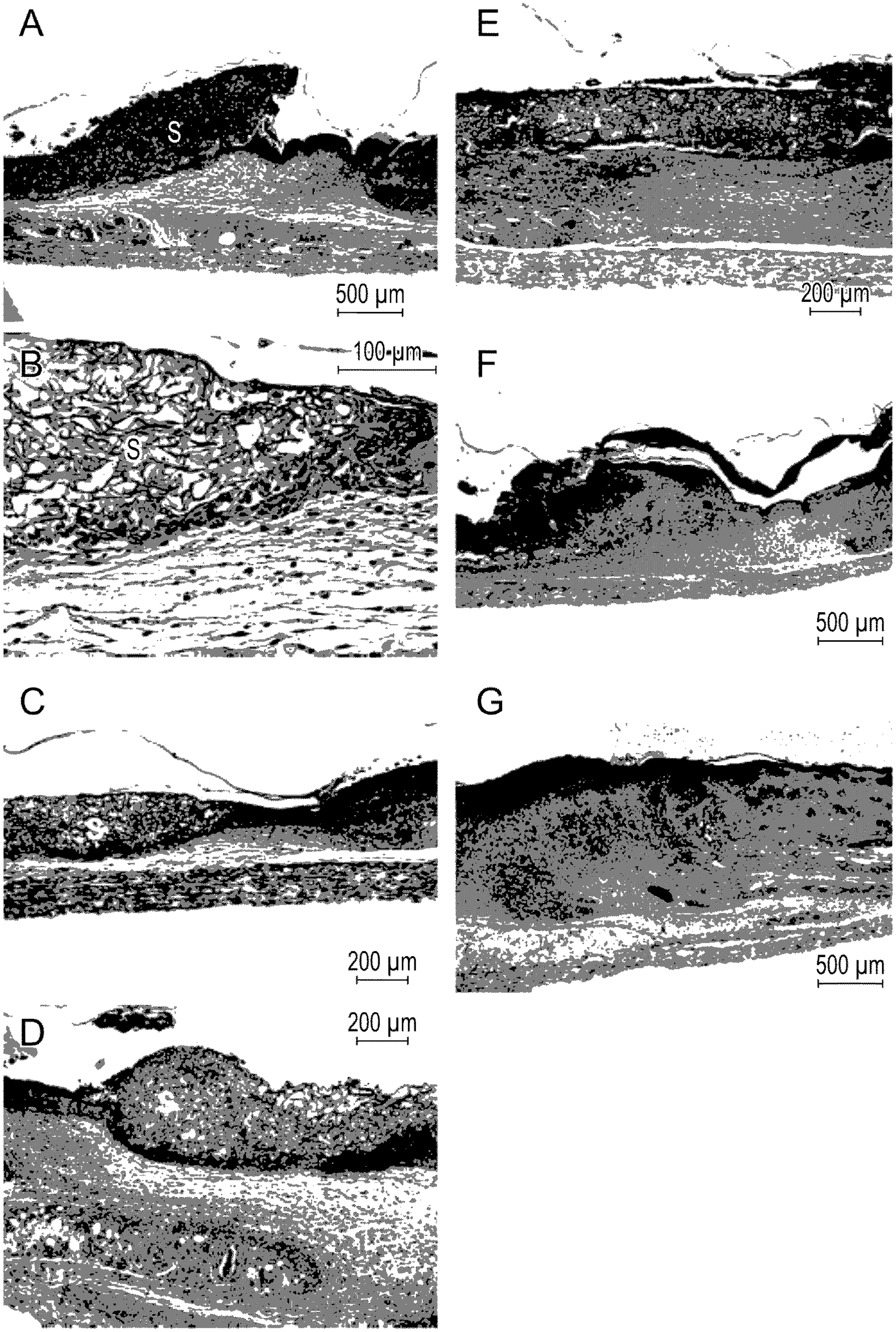
FIG. 8 shows representative images of H&E-stained wound sections from the cross-linked jellyfish collagen sponge group. Panels A), B) and C) represent images from wound sections collected on day 3 and panels D), E) and f) represent images from wound section collected on day 7.
Figure 9:
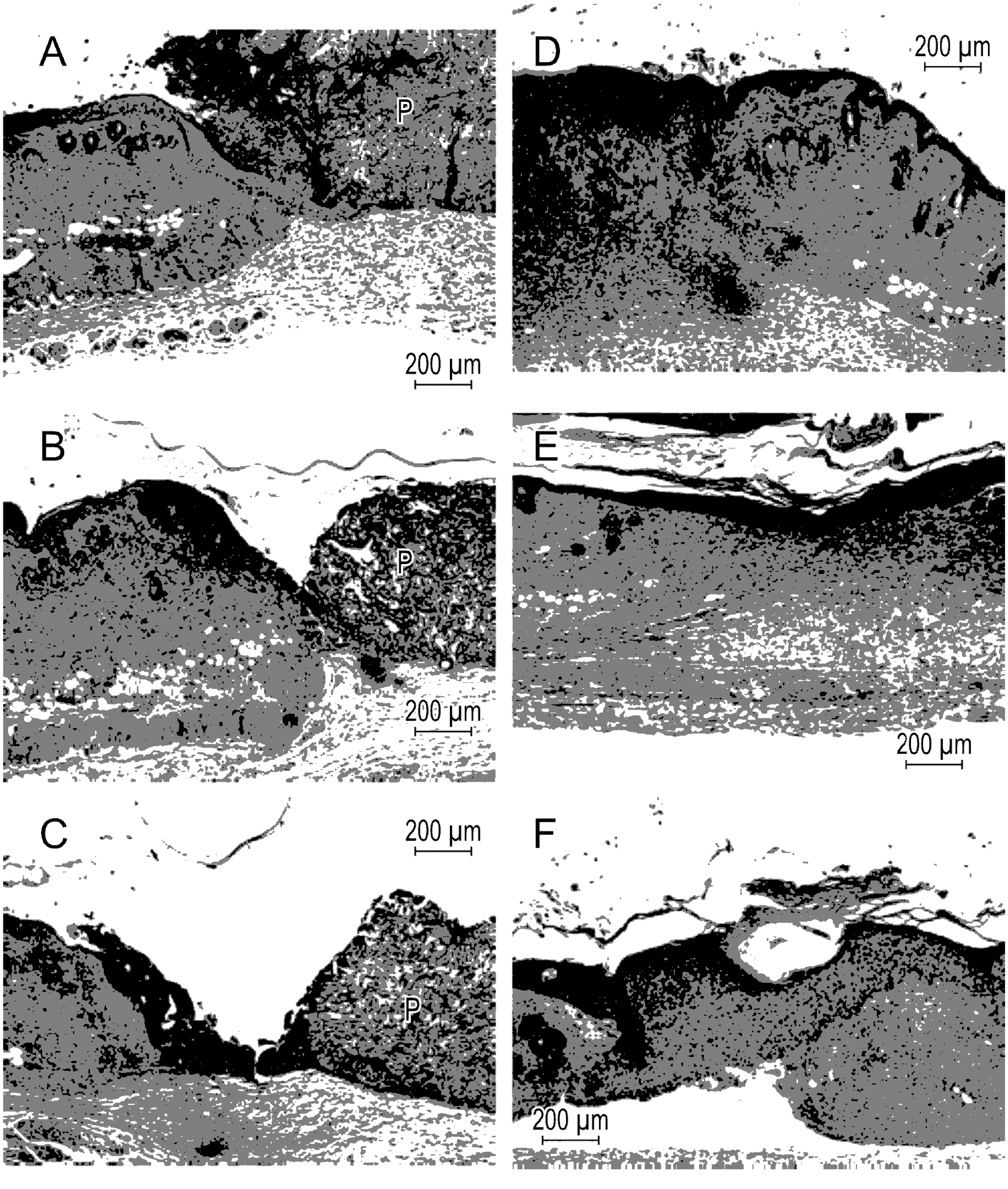
FIG. 9 shows representative images of H&E-stained wound sections from the Purocol® group. Panels A), B) and C) represent images from wound sections collected on day 3 and panels D), E) and f) represent images from wound section collected on day 7.

Observation of H&E-stained wound cross-sections demonstrated that the obvious structures of both the Puracol® and the cross-linked jellyfish collagen sponges were visible overlaying the wound on day 3. With the cross-linked jellyfish collagen sponges, the migration of the healing epithelium underneath the sponge was readily apparent. Representative images of wounds from each group are shown in FIG. 5 (Tegaderm only), FIG. 6 (jellyfish collagen sponge), FIG. 7 (chemically-modified (thiolated) jellyfish collagen paste), FIG. 8 (cross-linked jellyfish collagen sponge) and FIG. 9 (Puracol®). These show the wound edge, with unwounded skin (often with a hyperplastic epithelial layer) adjacent to the wound. The Tegaderm dressing can be seen as a wavy line above the surface of the skin in the images.

Figure 10:
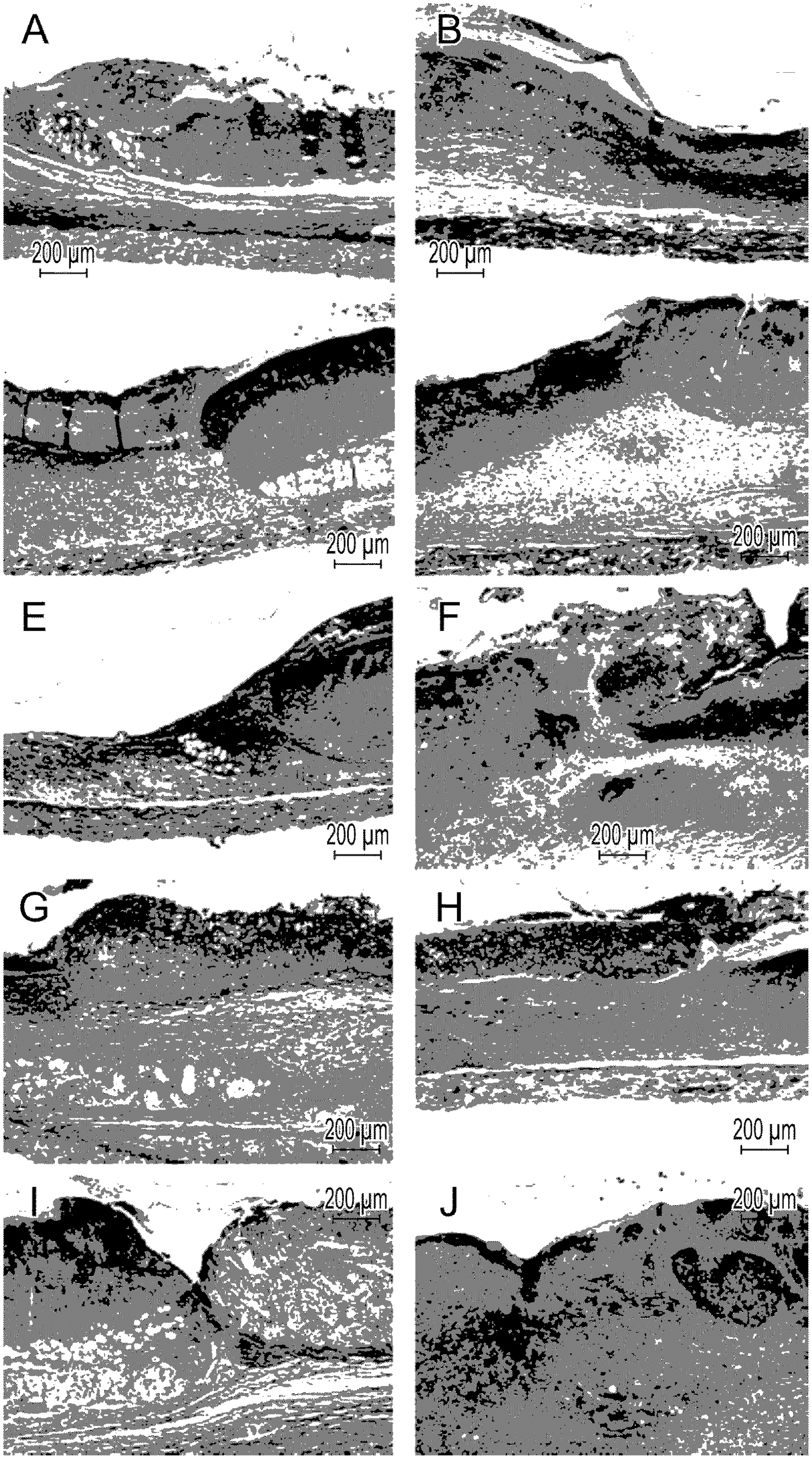
FIG. 10 shows representative images of Collagen I stained wound sections from the different treatment groups at day 3 and day 7. Panel A) shows a wound section from the Tegaderm group at day 3, panel B) shows a wound section from the Tegaderm group at day 7, panel C) shows a wound section from the jellyfish collagen sponge group at day 3, panel D) shows a wound section from the jellyfish collagen sponge group at day 7, E) shows a wound section from the chemically modified (thiolated) jellyfish collagen paste group at day 3, panel F) shows a wound section from the chemically modified (thiolated) collagen paste group at day 7, panel G) shows a wound section from the cross-linked jellyfish collagen sponge group at day 3, panel H) shows a wound section from the cross-linked jellyfish collagen sponge group at day 7, panel I) shows a wound section from the Puracol® group at day 3 and panel L) shows a wound section from the Puracol® group at day 7.
Figure 11:
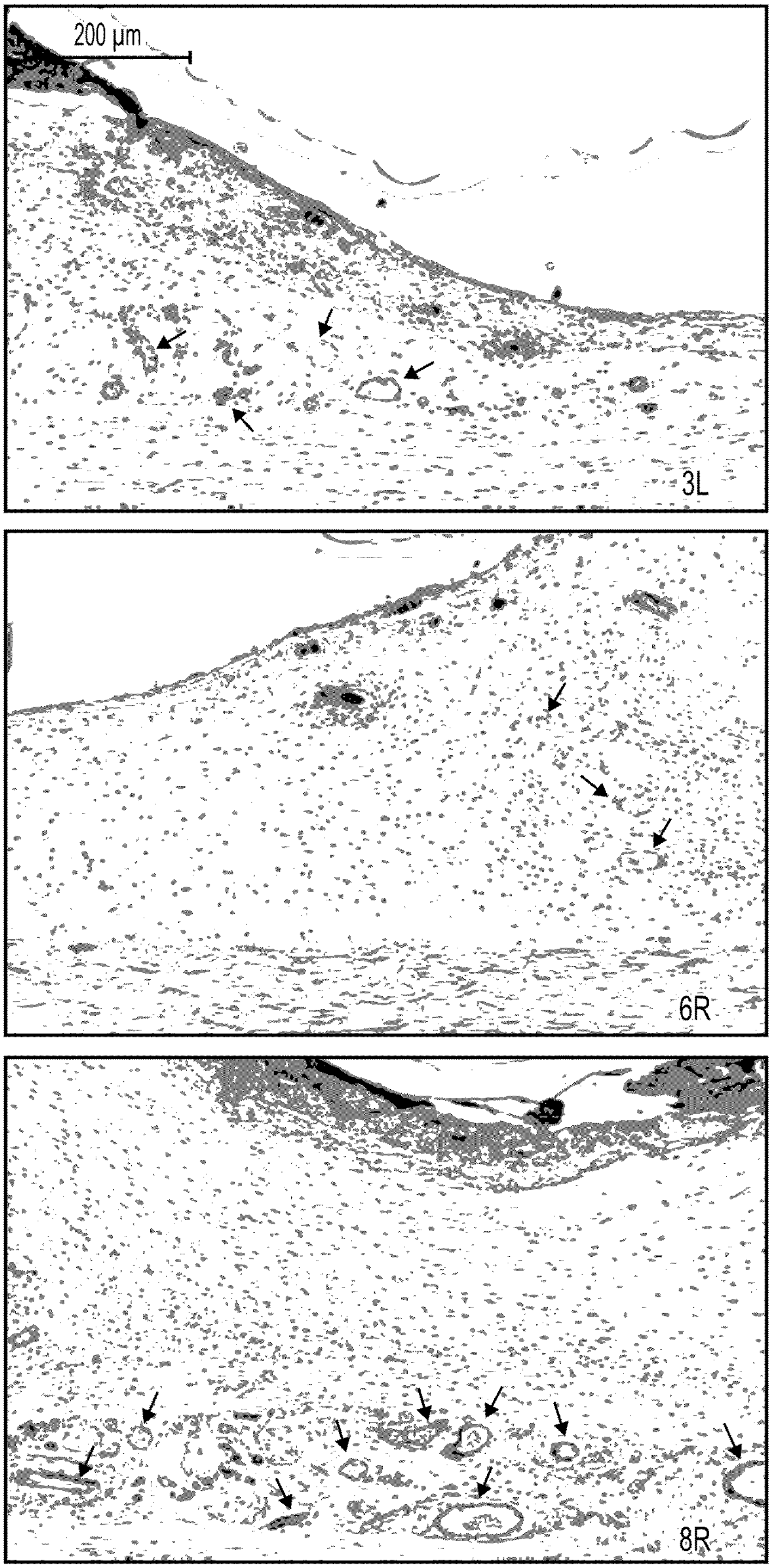
FIG. 11 shows representative images of wound sections from the Tegaderm only group (day 3) labelled with the specific endothelial cell marker, CD31.
Figure 12:
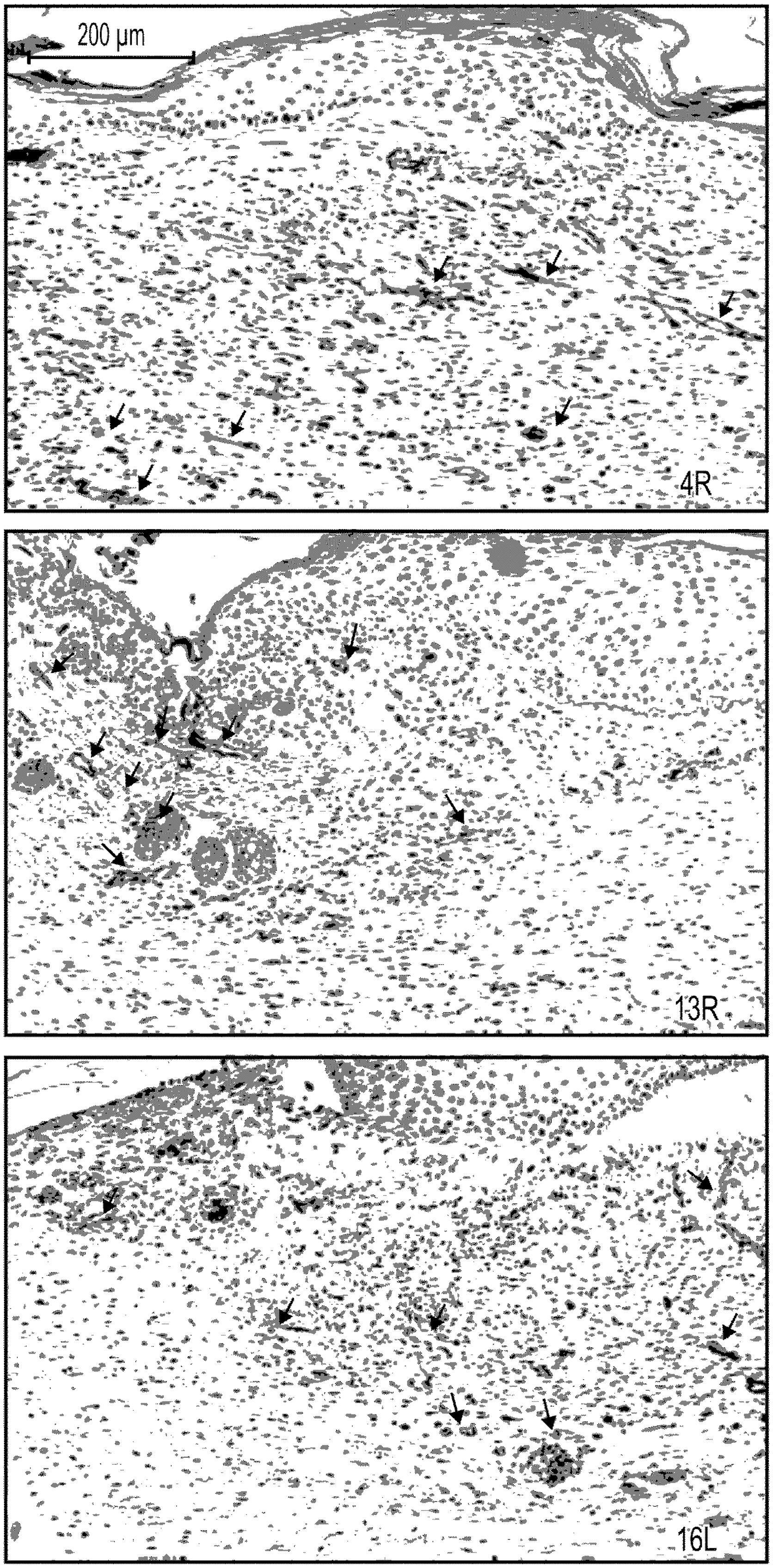
FIG. 12 shows representative images of wound sections from the Tegaderm only group (day 7) labelled with the specific endothelial cell marker, CD31.
Figure 13:
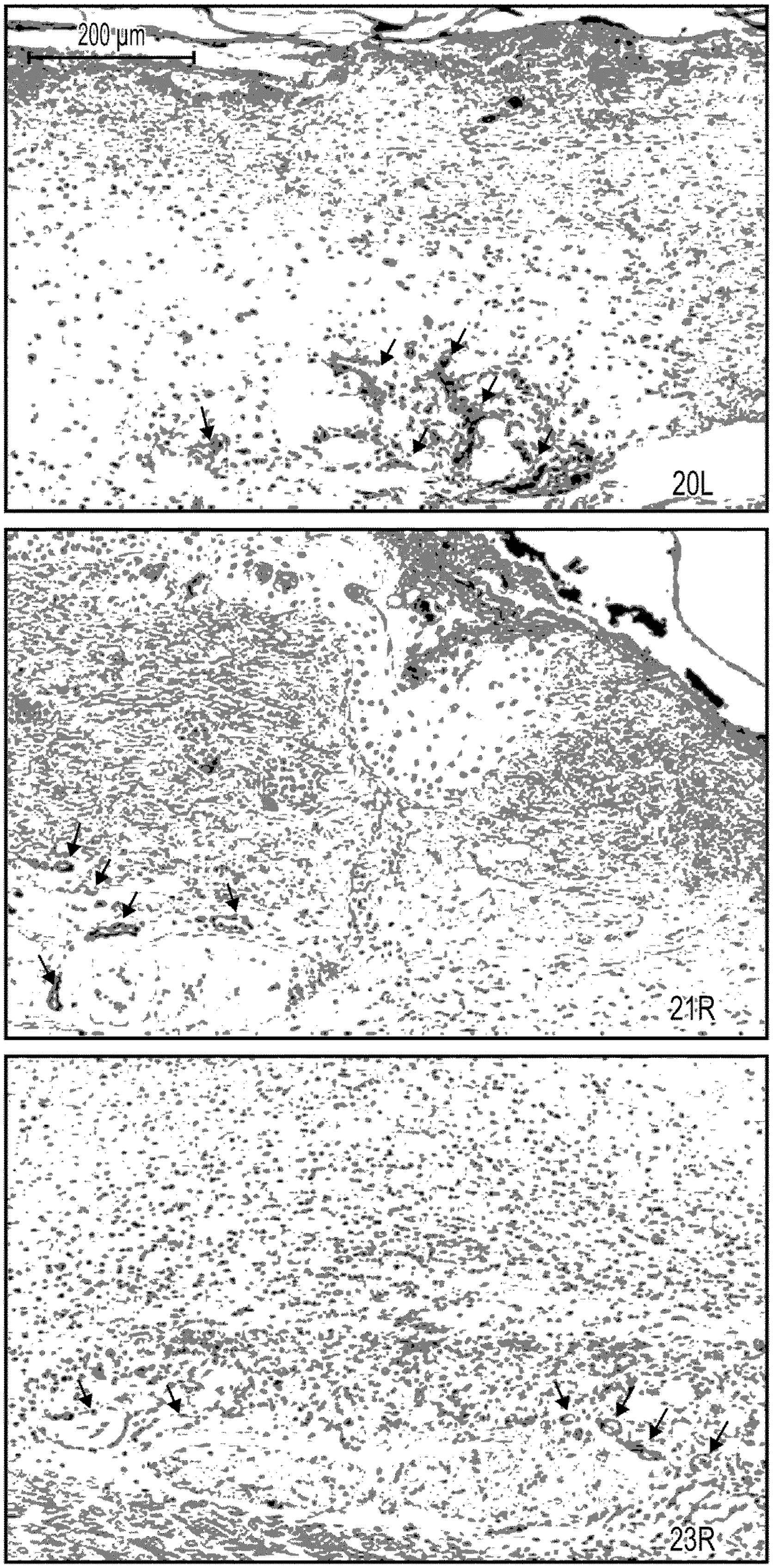
FIG. 13 shows representative images of wound sections from the jellyfish collagen sponge group (day 3) labelled with the specific endothelial cell marker, CD31.
Figure 14:
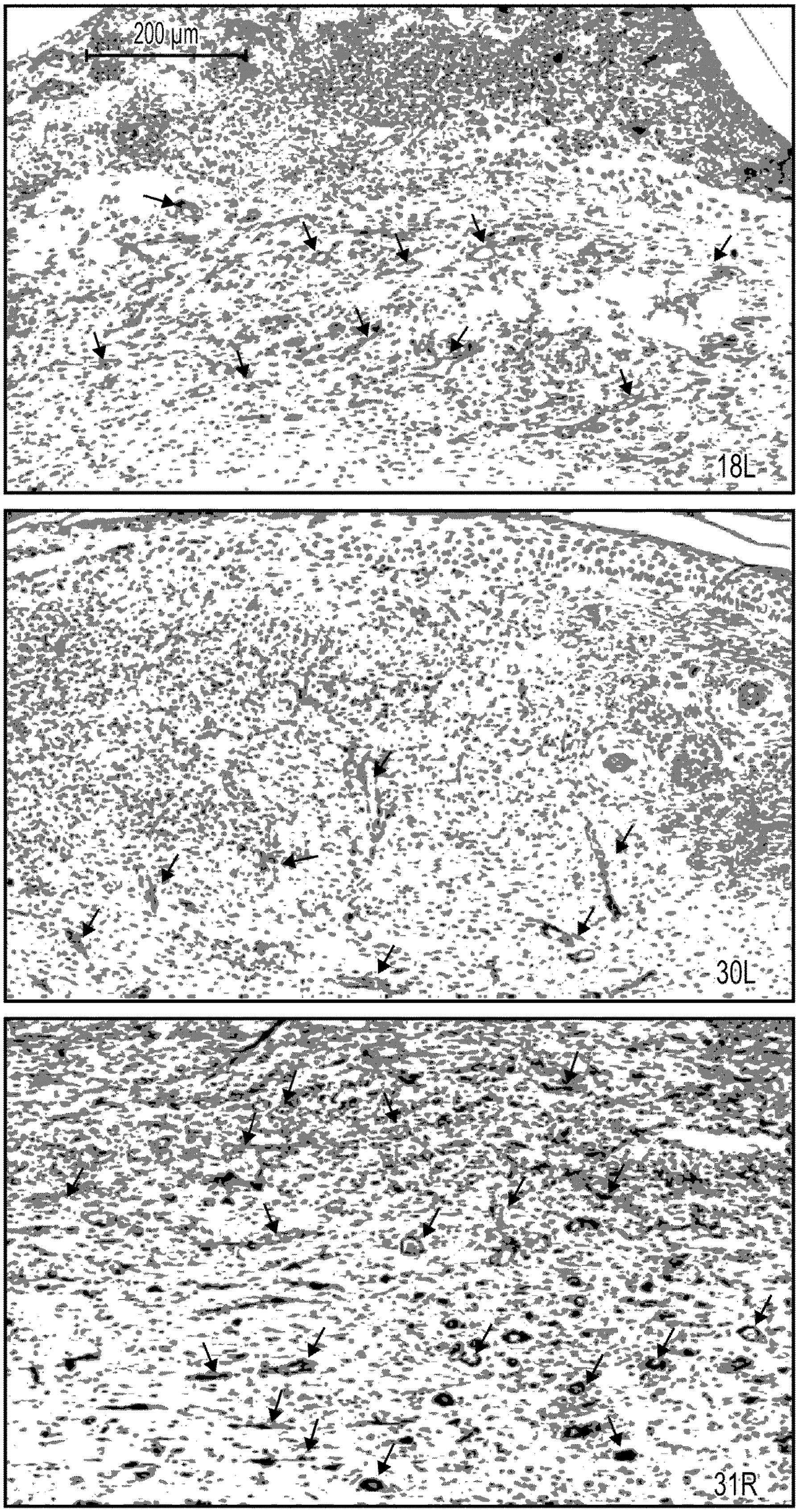
FIG. 14 shows representative images of wound sections from the jellyfish collagen sponge group (day 7) labelled with the specific endothelial cell marker, CD31.
Figure 15:
FIG. 15 shows representative images of wound sections from the chemically-modified (thiolated) jellyfish collagen paste group (day 3) labelled with the specific endothelial cell marker, CD31.
Figure 16:
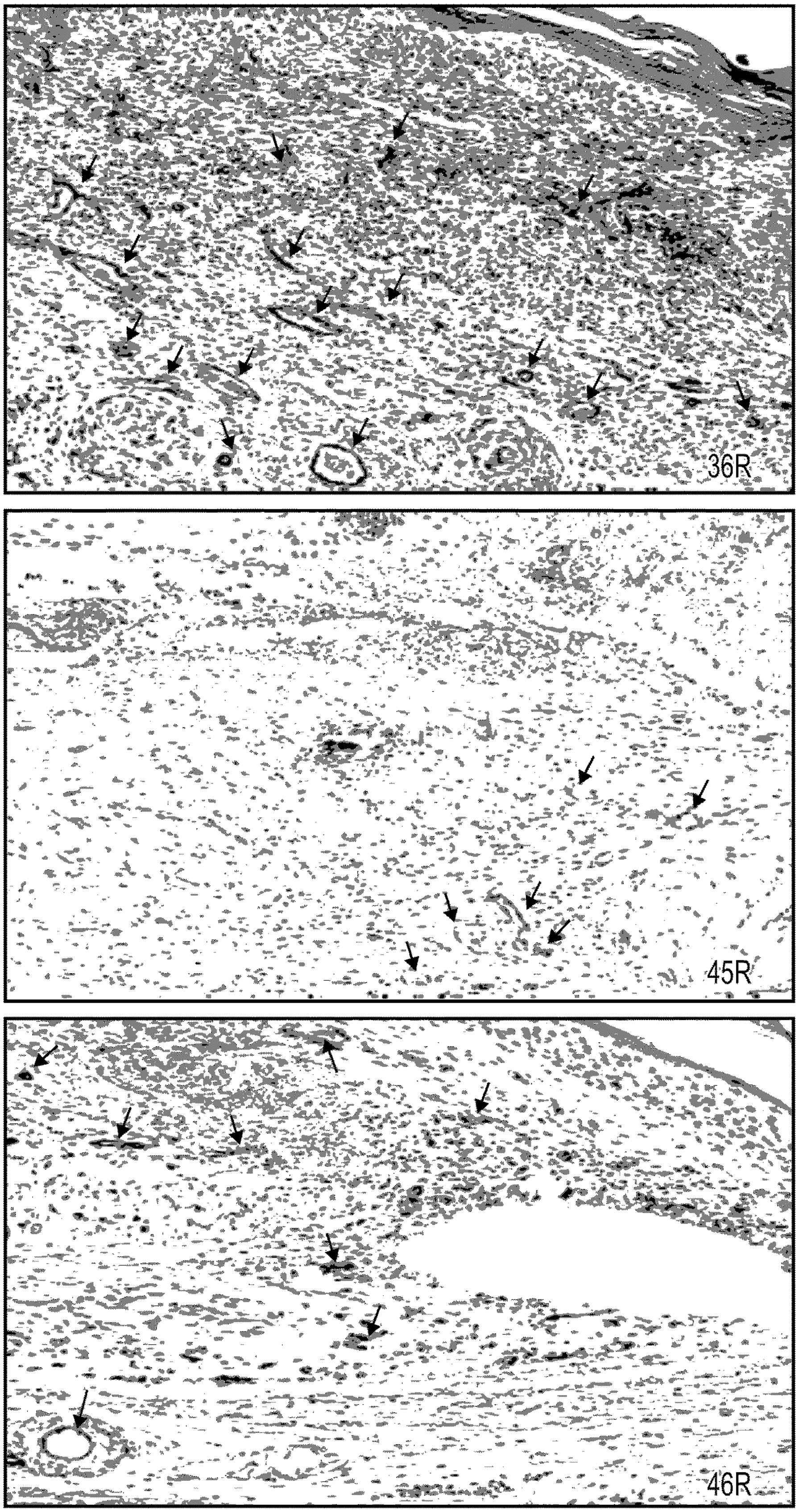
FIG. 16 shows representative images of wound sections from the chemically-modified (thiolated) jellyfish collagen paste group (day 7) labelled with the specific endothelial cell marker, CD31.
Figure 17:
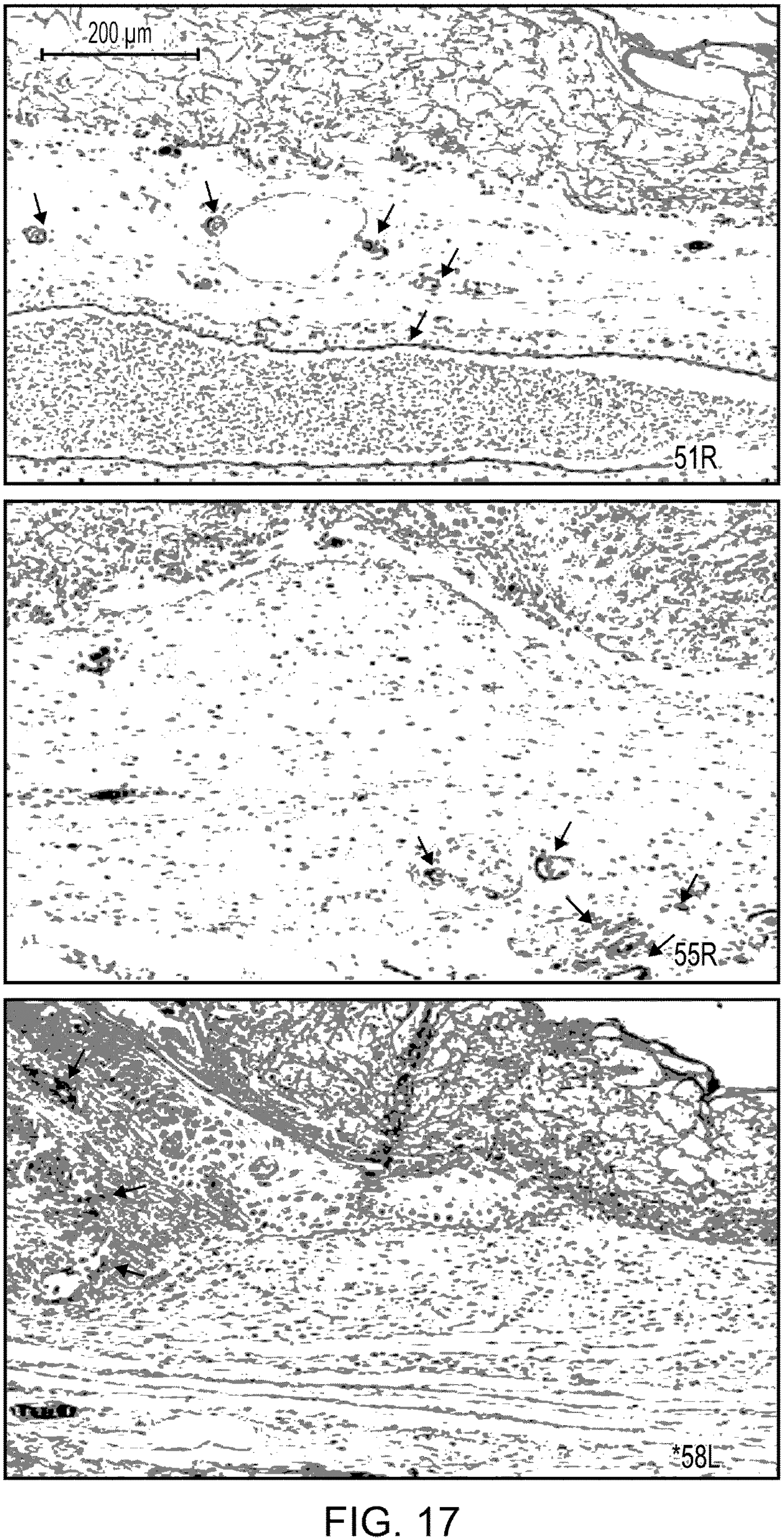
FIG. 17 shows representative images of wound sections from the cross-linked jellyfish collagen sponge group (day 3) labelled with the specific endothelial cell marker, CD31.
Figure 18:
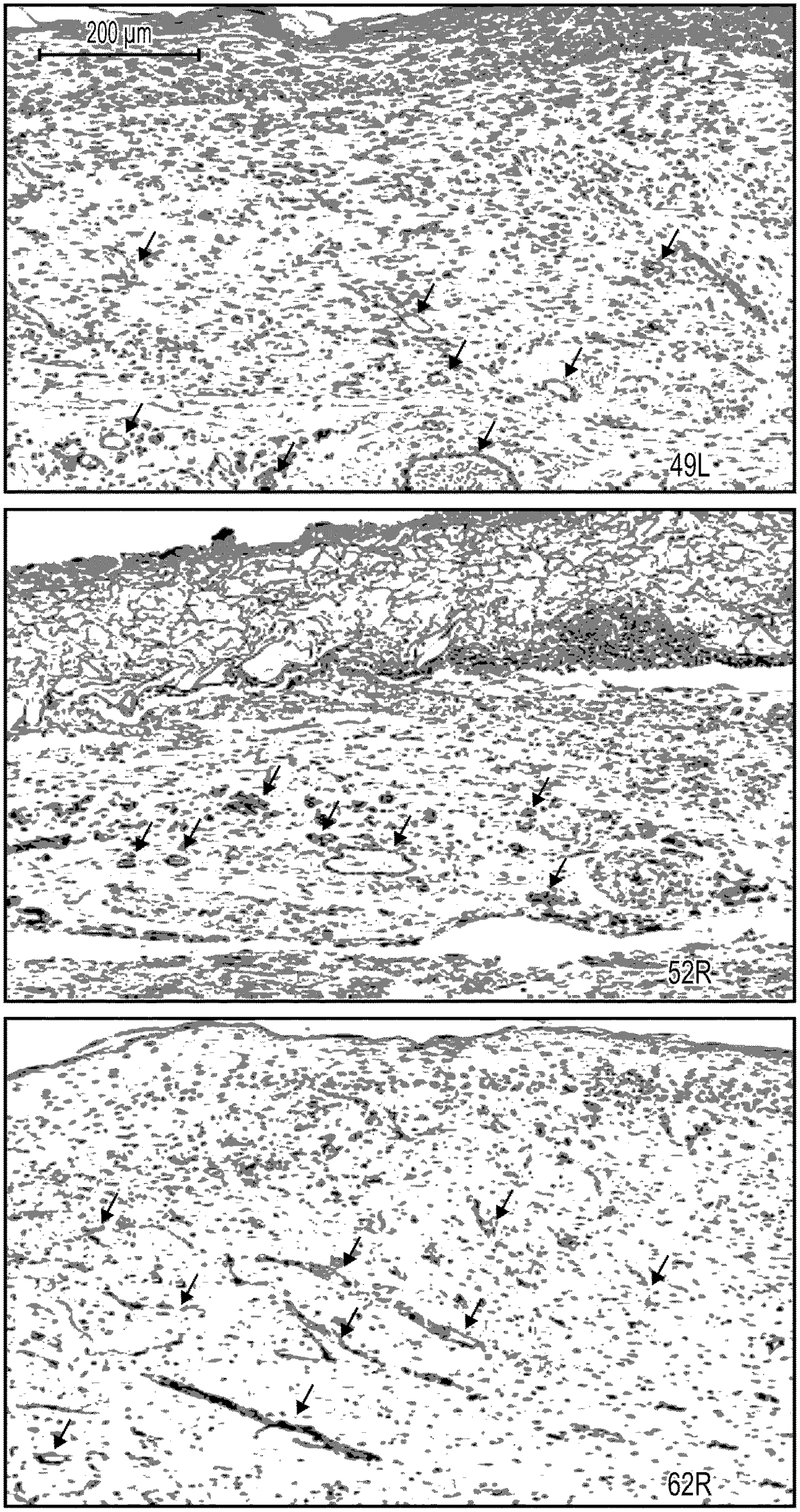
FIG. 18 shows representative images of wound sections from the cross-linked jellyfish collagen sponge group (day 7) labelled with the specific endothelial cell marker, CD31.
Figure 19:
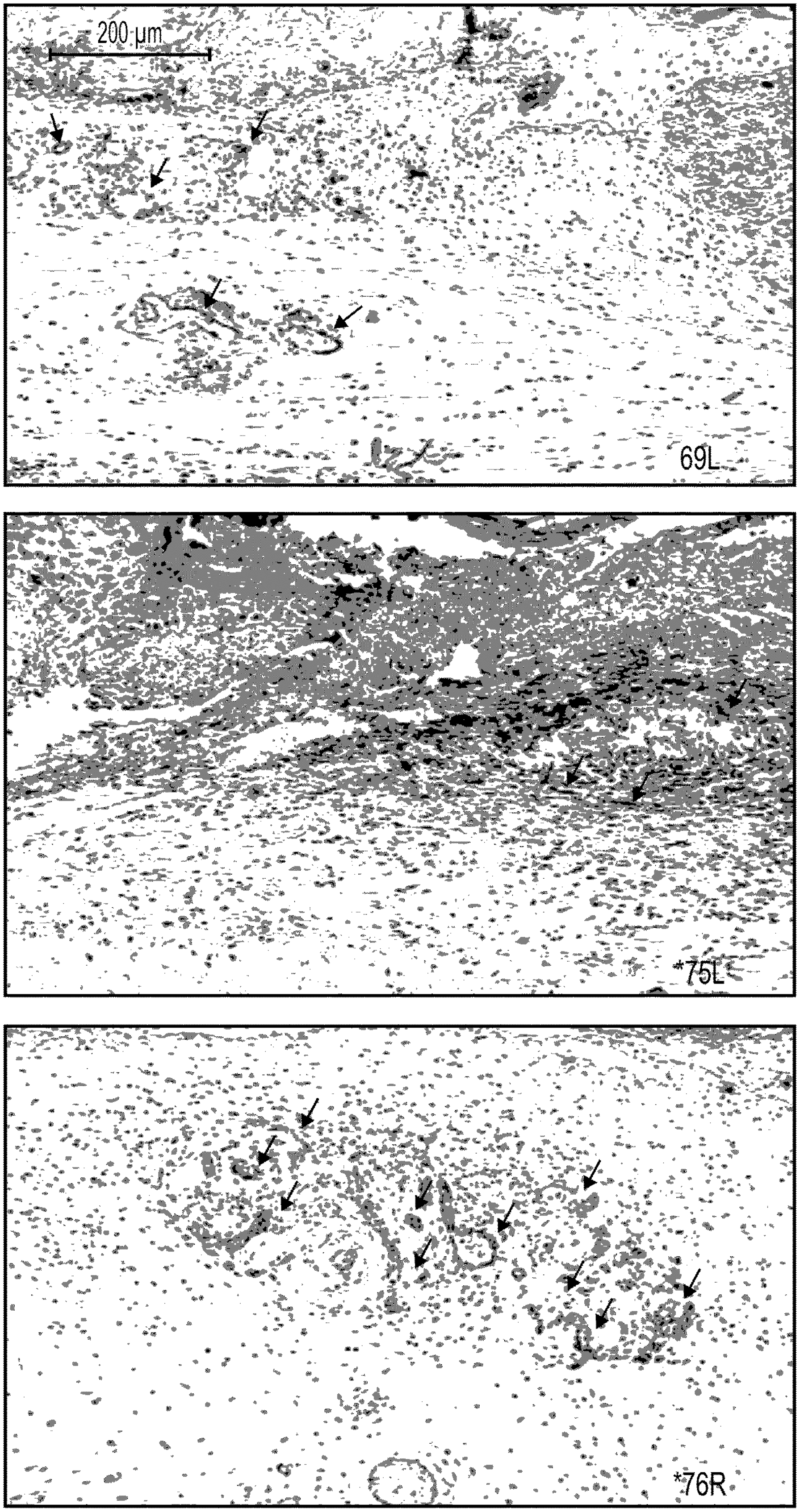
FIG. 19 shows representative images of wound sections from the Puracol® group (day 3) labelled with the specific endothelial cell marker, CD31.
Figure 20:
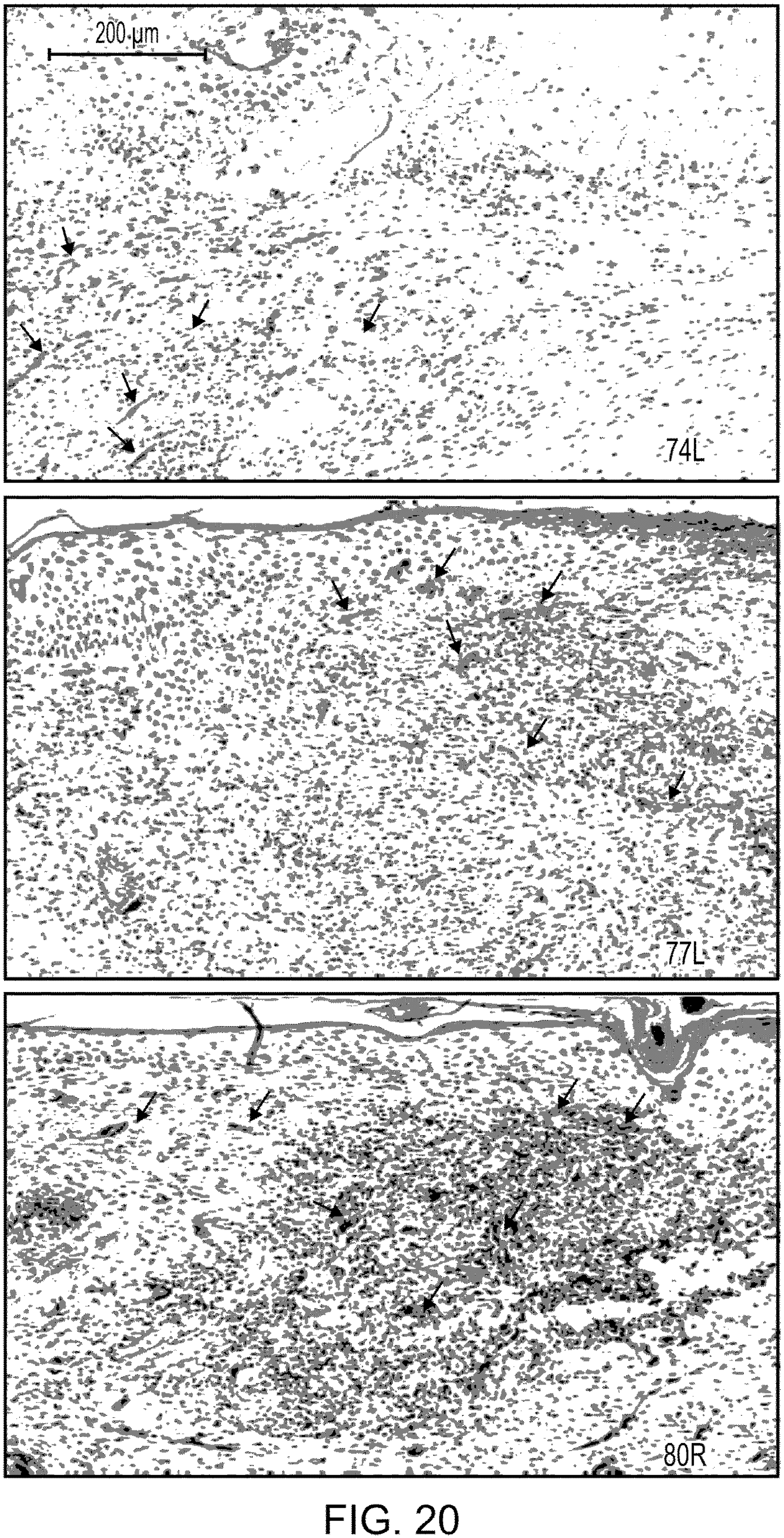
FIG. 20 shows representative images of wound sections from the Puracol® group (day 7) labelled with the specific endothelial cell marker, CD31.

Collagen I immunoreactivity was observed in all wound sections; representative images are shown in FIG. 10, which are from wounds also represented in the H&E images. Prominent collagen 1 immunoreactivity can be observed at the wound edge, and in day 7 wounds across the wound space.

CONCLUSION

Animals tolerated the different test items well, with no adverse effects. During the seven days after wounding, wounds healed well with evidence of re-epithelialisation in most animals, and both the amount and maturity of granulation tissue increasing over time. Both types of jellyfish collagen sponge were superior to Tegaderm dressing alone, with respect to the extent of tissue granulation in the wound space by day 7, with the cross-linked jellyfish collagen sponge also demonstrating more re-epithelialisation. In contrast, the performance of the jellyfish sponge and the reference product Puracol® dressing was similar.

This study demonstrates that jellyfish collagen is a suitable alternative, with at least an equivalent efficacy, to already known products on the market for treating wounds. These known products are typically of mammalian origin and as such are associated with a number of disadvantages. The provision of an alternative source of collagen suitable for the treatment of wounds is thus extremely advantageous.

Example 2—Immunohistochemical Labelling Using an Anti-Mouse CD31 Antibody on Mouse Wound Healing Formalin-Fixed Paraffin-Embedded (FFPE) Sample Aim The aim of this study was to section and to immunohistochemically label with anti-mouse CD31, 152 FFPE mouse wounds obtained by study 18/099, a study to determine the effects of test items in a cutaneous wounding healing murine model. CD31 is an endothelial cell marker which is commonly used to determine and measure angiogenesis.

Procedure

152 FFPE mouse wounds obtained during study 18/099—a study to determine the effects of test items in a cutaneous wounding healing murine model at day 3 and day 7 time points, were sectioned at 3 μm thickness to provide one slide with two non-serial sections per slide. Sections were mounted on charged slides and dried overnight at 37° C.

The 152 FFPE sections were dewaxed and rehydrated before antigen retrieval was performed using proteolytic digestion with Proteinase K (Dako S3020) for 5 minutes at room temperature. Endogenous peroxidase was blocked for 15 minutes with 0.3% $H_2O_2$ in TBST before non-specific binding was blocked with 2.5% goat serum for 30 minutes. The sections were incubated with an anti-mouse CD31, rat monoclonal antibody, clone MEC13.3 (BD Pharmingen 550274) at 0.3125 μg/ml for 1 hour at room temperature. A corresponding rat monoclonal IgG2a isotype control was included at a matched concentration to the primary antibody on one sample. A sample of untreated mouse skin was included as a positive tissue control. Sections were washed in TBST and then incubated with anti-rat, mouse adsorbed polymer (Vector ImmPress MP-7444). All labelling was visualized using DAB (Vector ImmPact SK-4105) and sections were counterstained with haematoxylin before being permanently mounted. Each labelled slide was checked against its corresponding block to confirm a match and examined microscopically as part of the quality control procedure.

Thirty representative images were taken using an AxioVision Imaging System which consists of a Zeiss Axioscope A1 microscope, AxioCam MRc Camera and AxioVision software installed on a computer workstation to capture images. Images were taken using a ×10 objective.

Representative images from each of the treatment wound dressing groups (Tegaderm only, Jellyfish collagen sponge, chemically-modified (thiolated) jellyfish collagen paste, cross-linked Jellyfish collagen sponge and Puracol) were taken at day 3 (FIGS. 11, 13, 15, 17, and 19) and day 7 (FIGS. 12, 14, 16, 18, and 20). For orientation, each wound was imaged with the epidermis uppermost i.e. at the top of the image.

Results and Conclusion

The wound samples taken from study 18/099 were successfully labelled for a mouse-specific endothelial cell marker, CD31, which is indicative of angiogenesis occurring in these samples treated with jellyfish collagen.

As with the in vivo data, the above in vitro data show that jellyfish collagen is an appropriate alternative to bovine collagen for use in the treatment of wounds, one which lacks the disadvantages associated with using a mammalian collagen, such as enhanced risk of disease/prion transmission, increased risk of contamination and the significant cost associated with obtaining collagen from mammalian sources. This finding is a surprising one given the vastly different physicochemical and amino acid properties of jellyfish collagens to mammalian collagen.

Example 3—Investigation into the Impact of Jellyfish Derived Collagen Formulations on Healing of Full Thickness Excision Wounds in the db/db (BKS.CG-m Dock $7^{m}$+/_+$Lepr^{db}$/J) Diabetic Mouse Aim To investigate the impact of three Jellyfish-derived collagen formulations on wound healing in the BKS.Cg-m Dock7m+/+Leprdb/J (db/db) diabetic mouse—a model of delayed cutaneous wound healing.

Procedure

Materials under test:

- 96-well plate formed (~6 mm diameter) Jellagen non-crosslinked sponges—CHCl3 sterilized.
- Micronised 0.5% EDC* crosslinked Jellagen Powder—CHCl3 sterile (4 g).
- Micronised 1% EDC (N-(3-Dimethylaminopropyl)-N'-ethylcarbodiimide hydrochloride) crosslinked Jellagen Powder—CHCl3 sterile (4 g).
- Promogran™ (Protease Modulating Matrix, Acelity, USA). Lot 1912V001; Expiry 28 Feb. 2021.

BKS.Cg-m Dock7m+/+Leprdb/J Diabetic Mouse Model

The methods followed are briefly outlined below. The live phase of this study was undertaken between 19 Sep. 2019 and 9 Oct. 2019.

Diabetic mice (BKS.Cg-m Dock7m+/+Leprdb/J, Jackson Labs, Bar Harbour, ME, USA) were brought into the UK aged approximately 9-10 weeks and were allowed to acclimate for one week prior to the start of the study. Animals were maintained according to UK Home Office regulations and the specific requirements of diabetic animals. Animals were randomly allocated to 5 treatment groups (Table 1).

TABLE 1

Experimental Groups

| Tx Group | Treatment (FD = Film Dressing) | Application of treatment (days) | Animal Codes | "n" |
|---|---|---|---|---|
| 1 | Film Dressing Only (Negative Control) | 0, 4, 8, 12, and 16 | JELL-01.01 to 01.10 | 10 |
| 2 | Non-crosslinked sponge (~6 mm diameter disc) + FD | 0, 8, 12, and 16 | JELL-01.11 to 01.20 | 10 |
| 3 | 5 mg Micronised 0.5% EDC crosslinked Jellagen Powder + FD | Day 0 only | JELL-01.21 to 01.30 | 10 |
| 4 | 5 mg Micronised 1.0% EDC crosslinked Jellagen Powder + FD | Day 0 only | JELL-01.31 to 01.40 | 10 |
| 5 | Promogran ™ (~6 mm diameter disc) + FD | 0, 8, 12, and 16 | JELL-01.41 to 01.50 | 10 |

Briefly, mice were anaesthetised using isofluorane and air, and their dorsal flank skin was clipped and cleansed according to protocol. A single standardised full-thickness wound (10 mm×10 mm) was created on the left dorsal flank approximately 5 mm from the spine. Wounds were cleaned with sterile saline-soaked gauze swabs and dried with sterile gauze. 15 μL of sterile physiological saline was then applied to the surface of each wound. The materials under test were then applied directly to the surface of saline-moistened wounds.

Wounds in group 2 received one ~6 mm diameter (96-well formed) non-crosslinked Jellagen sponge; those in group 5 received a 6 mm disk of the commercial comparator Promogran™ (Acelity, USA), and those in groups 3 and 4 received 5 mg of EDC-crosslinked Jellagen powder (0.5% and 1.0% EDC crosslinked, respectively). Immediately after product application, all wounds were dressed with the semi-occlusive film dressing Tegaderm™ Film, (3M Deutschland GmbH, Germany). The condition of this film dressing was examined daily throughout the study and was replaced if it became detached.

On post-wounding days 4, 8, 12, and 16 all animals were re-anaesthetised, their film dressings and any free debris removed, and their wounds (and marginal skin) were gently cleaned using sterile saline-soaked gauze (without disturbing any existing products within the wound). Wounds were then photographed not shown), moistened with 15 μl of sterile physiological saline, and products re-applied to wounds in selected groups on selected days.

It was originally intended that wounds in groups 2 (non-crosslinked Jellagen sponge) and 5 (Promogran™, Acelity, USA) would receive a second application of product on post-wounding day 4. In view of the observation that neither of these products had experienced significant degradation, it was decided (and agreed with the sponsor) that re-application would not be undertaken at this time point. Product re-application—without prior removal of existing undegraded product—was, however, undertaken on post-wounding days 8, 12, and 16.

After product re-application (where indicated), wounds were re-dressed (as above) with Tegaderm™ Film dressing—and animals were allowed to recover in a warmed environment (~35° C.). Immediately after wounding, and subsequently after cleaning on days 4, 8, 12, 16, and 20, all wounds were digitally photographed together with a calibration/identity plate.

All animals were culled on post-wounding day 20. One hour prior to termination all animals received an i.p. injection (30 μg/g) of 5-bromo-2'-deoxyuridine (Sigma B5002) in normal saline to facilitate the possibility of detection of cellular proliferation in histological sections. Wound and surrounding marginal tissue was then harvested from all wounds. Tissues were fixed (Neutral Buffered Formalin, Sigma) and embedded in paraffin wax to facilitate histological investigation.

Overview

This study examined the effect of three Jellyfish-derived formulations (non-crosslinked Jellagen sponge, 0.5% EDC crosslinked Jellagen Powder and 1.0% EDC crosslinked Jellagen Powder), applied topically, on the repair of full-thickness excisional skin wounds in the healing-impaired db/db diabetic mouse.

The healing of wounds in receipt of these formulations/products was compared with each other, with that of wounds in receipt of a commercial comparator (Promogran™ Protease Modulating Matrix, Acelity, USA) and, with that of control (film dressing only) treated wounds.

Wound healing was assessed over a 20-day period in terms of (i) initiation of neo-dermal repair responses, and (ii) wound closure. Initiation of neo-dermal tissue formation was expressed as the number of wounds responding in each group at each time point. Wound closure was considered in both overall terms and in terms of its components wound contraction and wound re-epithelialisation. Wound closure (contraction and re-epithelialisation) was determined from digital photographs taken on post-wounding days 0, 4, 8, 12, 16, and 20 post-wounding. At the histological level, H&E-stained sections of wound tissues (harvested on day 20) were briefly considered and compared in terms of granulation tissue formation and re-epithelialisation, and (in the case of the two EDC crosslinked powder formulations) in terms of their potential use as structural scaffolds to support tissue regeneration.

Summary of Results—Wound Closure

Figure 21:
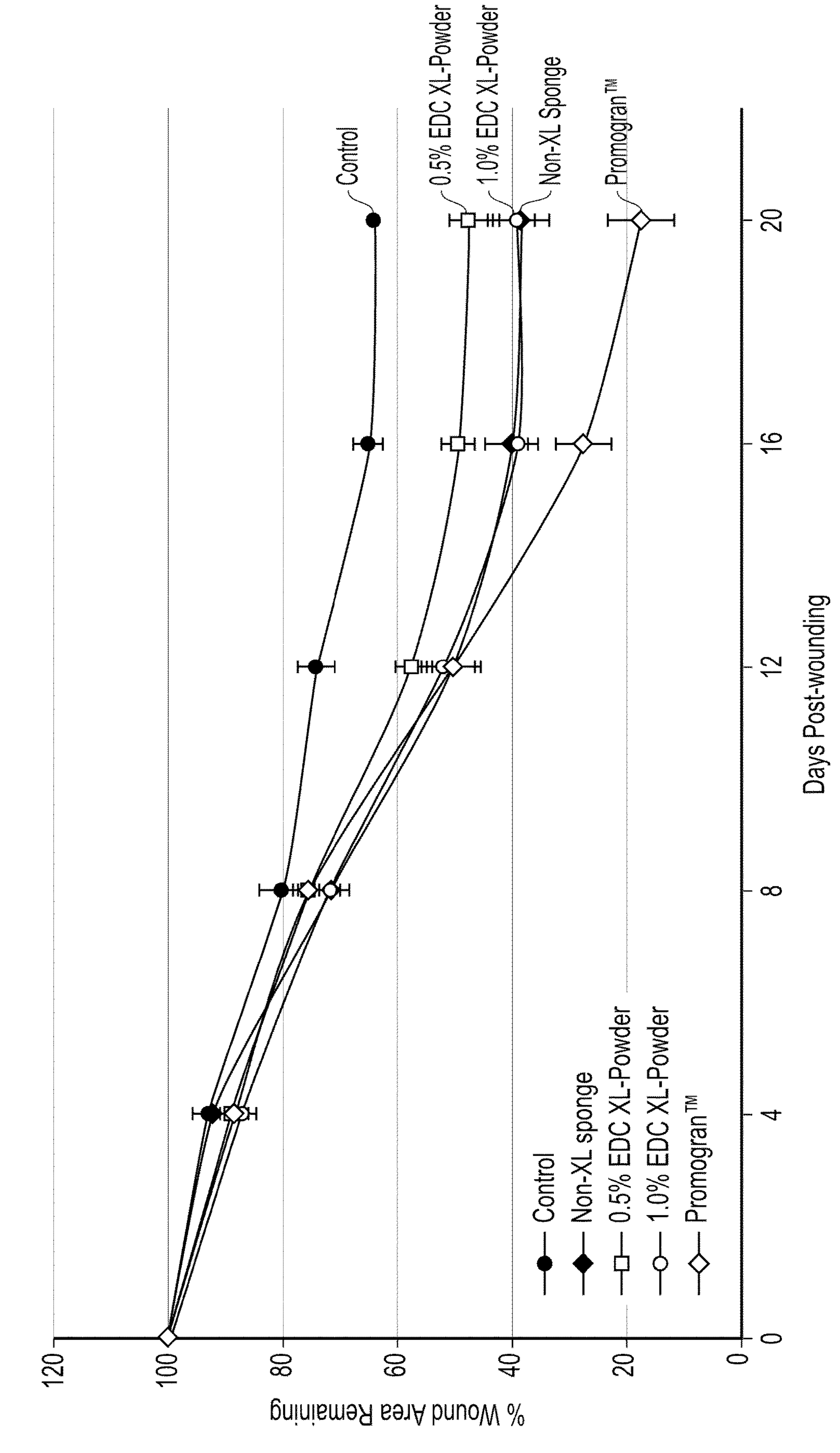
FIG. 21 shows wound closure profiles of the treatment groups as "% wound area remaining with time" data in a db/db (BKS.CG-m Dock 7m+/_+Leprdb/J) diabetic mouse model. The experiments were carried out as described in Example 3 and the test groups were: Control (film dressing only); Non-crosslinked sponge; 0.5% EDC XL-powder; 1.0% EDC XL-powder; Promogran™).

Each wound was digitally photographed, along with an identification/calibration plate, immediately after injury and subsequently on days 4, 8, 12, 16, and 20. For a given wound at a given time point, wound closure was expressed as the percentage wound area remaining relative to the initial wound area immediately after injury (i.e. day 0). Mean percentage wound area remaining data for all treatment groups are described in Table 2 below and shown in FIG. 21.

TABLE 2

Percentage "Wound Area Remaining" data for all study groups.

| | | % wound area remaining with time - open wound area (mean +/− standard error) | | | | | |
|---|---|---|---|---|---|---|---|
| | Group | Days post-wounding | 4 | 8 | 12 | 16 | 20 |
| Treatment | 1 | Control | 93.38 ± 2.35 | 80.49 ± 3.82 | 74.35 ± 3.14 | 65.15 ± 2.52 | 64.17 ± 2.42 |
| | 2 | Non-XL sponge | 92.41 ± 3.44 | 71.86 ± 3.34 | 50.93 ± 5.11 | 40.35 ± 4.55 | 38.72 ± 4.88 |
| | 3 | 0.5% EDC XL-Powder | 89.33 ± 1.97 | 75.45 ± 2.86 | 58.00 ± 2.37 | 49.55 ± 2.79 | 47.71 ± 3.38 |
| | 4 | 1.0% EDC XL-Powder | 87.40 ± 2.66 | 72.10 ± 1.91 | 52.21 ± 1.87 | 39.11 ± 1.76 | 39.41 ± 3.03 |
| | 5 | Promogran ™ | 88.75 ± 2.56 | 75.63 ± 2.03 | 50.80 ± 4.25 | 27.80 ± 4.82 | 17.75 ± 5.68 |

When wound closure (in terms of change in '% open wound area' with time) was considered, the following was observed:

- All of the three Jellagen products evaluated were found to significantly promote closure compared to 'film dressing only' Control treatment from day 12 onwards.
- When the three Jellagen products were compared, application of the non-crosslinked sponge gave rise to similar levels of closure as 1.0% EDC crosslinked powder, both of which were found to be marginally greater than that in response to 1.0% EDC crosslinked powder. No statistically significant differences in closure were observed between the three Jellagen product treatment groups.

Figure 22:
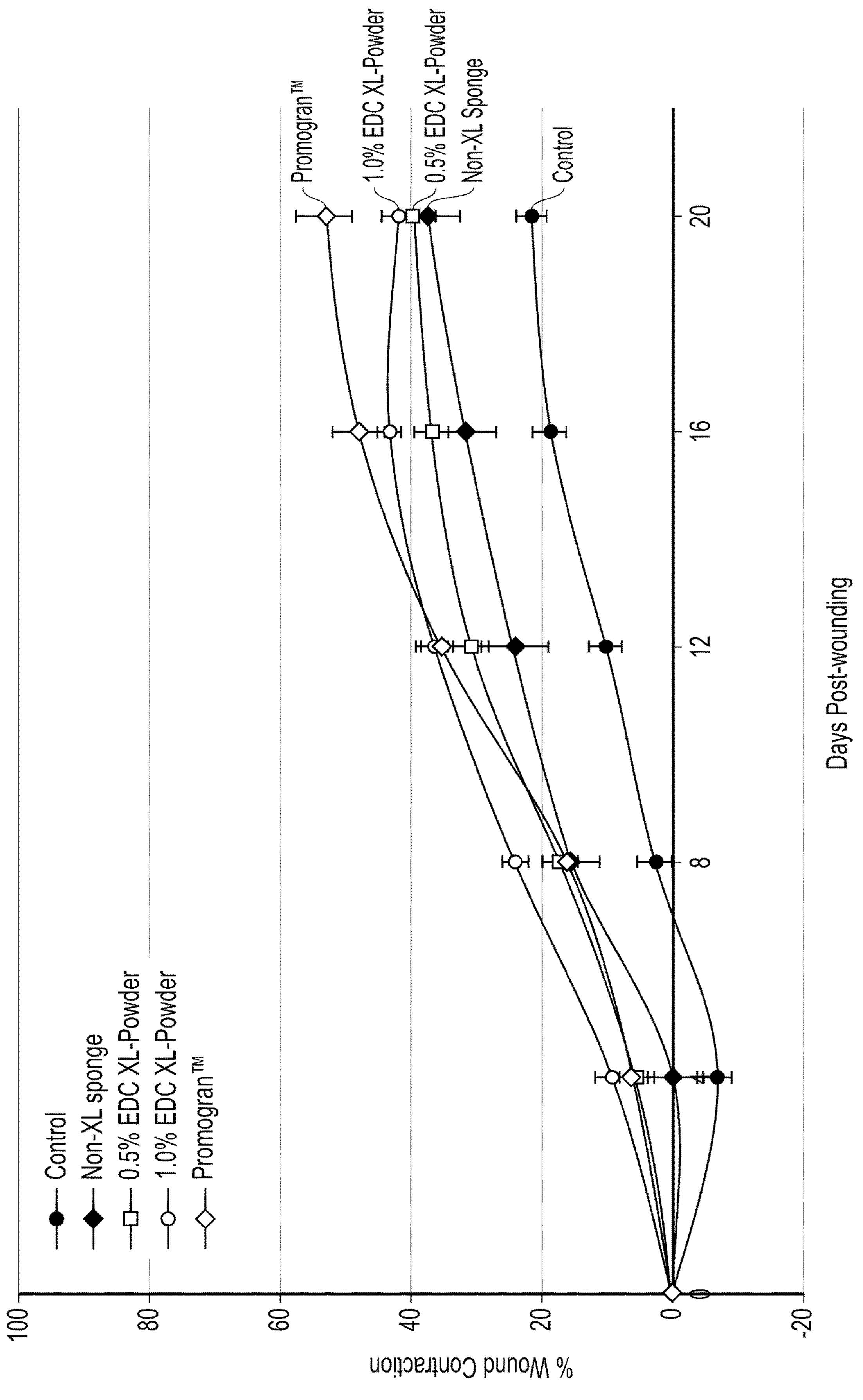
FIG. 22 shows wound contraction profiles of the treatment groups as "% wound contraction" data in a db/db (BKS.CG-m Dock 7m+/_+Leprdb/J) diabetic mouse model. The experiments were carried out as described in Example 3 and the test groups were: Control (film dressing only); Non-crosslinked sponge; 0.5% EDC XL-powder; 1.0% EDC XL-powder; Promogran™).

Wounds on non-diabetic mice close predominantly by contraction, while those on diabetic mice (such as those used in this study) have a significantly reduced ability to contract (possibly due to impoverished granulation tissue formation). As a result, untreated wounds on diabetic animals tend to close by re-epithelialisation to a greater extent than those on non-diabetic animals. An observation of enhanced contraction suggests improvement in granulation tissue function, which may in turn be explained by an increase in the amount of granulation tissue formed, an increase in the speed at which it is formed, or increased contractile capacity of the tissue. Mean percentage wound contraction data for all treatment groups are described in Table 3 (below) and shown in FIG. 22.

TABLE 3

Summary of "percentage wound contraction" data.

| | | % wound contraction with time (mean +/− standard error) | | | | | |
|---|---|---|---|---|---|---|---|
| | Group | Days post-wounding | 4 | 8 | 12 | 16 | 20 |
| Treatment | 1 | Control | −6.83 ± 2.13 | 2.78 ± 2.57 | 10.21 ± 2.49 | 18.86 ± 2.55 | 21.63 ± 2.32 |
| | 2 | Non-XL sponge | −0.05 ± 3.69 | 15.61 ± 4.44 | 24.22 ± 5.03 | 31.85 ± 4.84 | 37.42 ± 5.05 |
| | 3 | 0.5% EDC XL-Powder | 5.46 ± 2.52 | 17.36 ± 2.6 | 30.93 ± 2.71 | 36.99 ± 2.61 | 39.38 ± 3.14 |
| | 4 | 1.0% EDC XL-Powder | 9.12 ± 2.81 | 24.14 ± 2.09 | 36.53 ± 1.97 | 43.35 ± 1.92 | 41.96 ± 2.58 |
| | 5 | Promogran ™ | 6.23 ± 2.21 | 15.97 ± 1.54 | 35.49 ± 3.89 | 48.00 ± 4.03 | 53.26 ± 4.32 |

Summary of Results—Wound Contraction

Contraction is the centripetal movement of the wound margins, due to the compaction of granulation tissue within the "body" of the wound. The "compactional" forces that drive this process, are thought to reside in cells of the fibroblast lineage. In this study, percentage contraction was calculated as:

$$\%\ \text{contraction} = \frac{\text{The area defined by the boundary of normal dermis and the}}{\text{The original wound area (day 0)}} \times 100$$

When the impact of treatment on wound contraction was considered, the following was observed:

- All of the treatments considered were found to significantly accelerate wound contraction compared to 'film dressing only' Control treatment from day 8 onwards.
- When the three Jellagen products were compared, contraction tended to be more extensive in response to 1.0% EDC crosslinked powder, which tended to be more extensive than that observed in response to 0.5%, which in turn tended to be more extensive than that observed in response to non-crosslinked sponge. On statistical analysis, application of 1.0% EDC crosslinked powder was found to significantly promote contraction compared to treatment with non-cross-linked sponges.

Summary of Results—Wound Re-Epithelialisation

Figure 23:
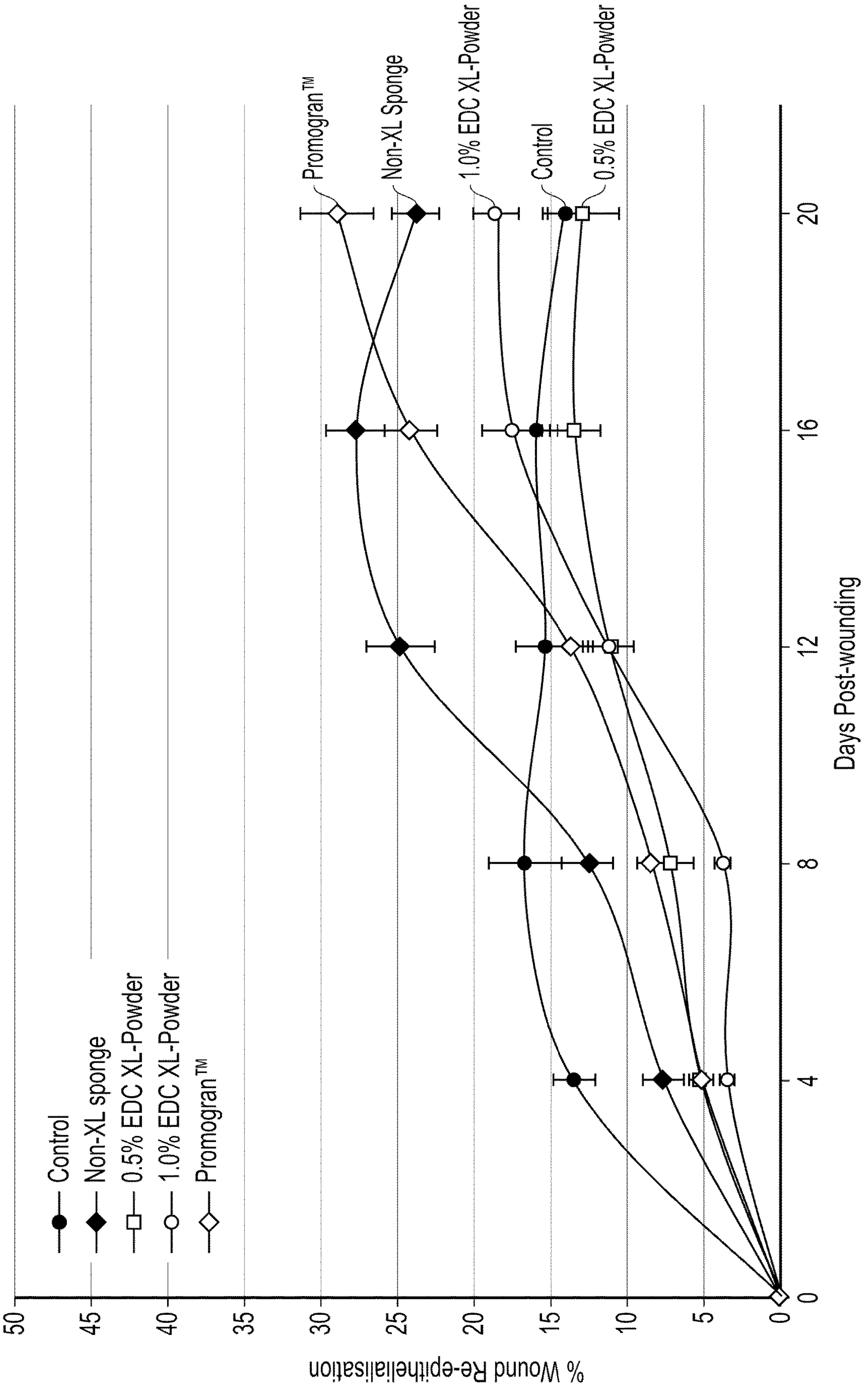
FIG. 23 shows profiles for re-epithelialisation of the wound as "% wound re-epithelialisation" that was first measurable on day 4 post-wounding between the different treatment groups in a db/db (BKS.CG-m Dock 7m+/_+Leprdb/J) diabetic mouse model. The experiments were carried out as described in Example 3 and the test groups were: Control (film dressing only); Non-crosslinked sponge; 0.5% EDC XL-powder; 1.0% EDC XL-powder; Promogran™).

For a given wound, at a given time point, the area of re-epithelialisation was expressed as a percentage of the original area of that wound immediately after injury. Mean percentage wound re-epithelialisation data for all treatment groups are described in Table 4 (below) and shown in FIG. 23.

TABLE 4

Summary of "percentage wound re-epithelialisation" data

| | | % wound re-epithelialisation with time (mean +/− standard error) | | | | | |
|---|---|---|---|---|---|---|---|
| | Group | Days post-wounding | 4 | 8 | 12 | 16 | 20 |
| Treatment | 1 | Control | 13.45 ± 1.41 | 16.74 ± 2.32 | 15.44 ± 1.80 | 15.99 ± 1.45 | 14.19 ± 1.36 |
| | 2 | Non-XL sponge | 7.63 ± 1.35 | 12.53 ± 1.64 | 24.85 ± 2.25 | 27.80 ± 1.98 | 23.86 ± 1.53 |
| | 3 | 0.5% EDC XL-Powder | 5.21 ± 0.77 | 7.18 ± 1.55 | 11.07 ± 1.46 | 13.46 ± 1.65 | 12.91 ± 2.36 |
| | 4 | 1.0% EDC XL-Powder | 3.48 ± 0.44 | 3.77 ± 0.48 | 11.26 ± 1.71 | 17.55 ± 1.93 | 18.63 ± 1.50 |
| | 5 | Promogran ™ | 5.02 ± 0.00 | 8.40 ± 0.93 | 13.71 ± 1.43 | 24.20 ± 1.83 | 28.99 ± 2.42 |

When the impact of treatment on wound re-epithelialisation was considered, the following was observed:

When the Jellagen treatment groups were considered, application of non-crosslinked sponges was found to be more effective than application of the EDC crosslinked powders.

Re-epithelialisation in response to non-crosslinked sponges was found to be greater than that observed in the Promogran™ treatment group on days 8, 12, and 16; and less on day 20.

Re-epithelialisation in response to the EDC crosslinked powders tended to be lower than that in response to 'film dressing only' control treatment for the majority of the study—though similar levels of re-epithelialisation had been achieved at the time of study conclusion on day 20.

Summary of Results—Initiation of Neo-Dermal Tissue Generation

All wounds in the study were visually assessed on a daily basis until day 8, and subsequently on days 10, 12, 14, 16, and 20 to establish their "healing" status. Each wound was scored as to whether it was displaying "neo-dermal tissue generation activity" within the central wound area. Scoring was undertaken independently by two independent observers and the average % of wounds displaying "neo-dermal tissue generation activity" was compared between treatment groups at each assessment point. The number of wounds responding in each treatment group on each day is displayed in Table 5. The mean time to respond for each group is displayed in Table 6. It should be noted that since 10 out of the 10 wounds in the 'film dressing only' treatment group did not respond during the study period, the mean value for 'time to respond' for this group is an unknown value greater than 20.

TABLE 5

Number of wounds displaying "Initiation of neo-dermal tissue formation' (underline indicates 100% initiation achieved)

| | | Day of Study | | | | | | | | | | | | | |
|---|---|---|---|---|---|---|---|---|---|---|---|---|---|---|---|
| Treatment Group | n | 1 | 2 | 3 | 4 | 5 | 6 | 7 | 8 | 10 | 12 | 14 | 16 | 18 | 20 |
| Control | 10 | 0 | 0 | 0 | 0 | 0 | 0 | 0 | 0 | 0 | 0 | 0 | 0 | 0 | 0 |
| Non-XL sponge | 10 | 0 | 0 | 0 | 0 | 0 | 0 | 1 | 1 | 1 | 4 | 8 | 10 | 10 | 10 |
| 0.5% EDC XL-Powder | 10 | 0 | 0 | 0 | 0 | 0 | 0 | 0 | 1 | 6 | 10 | 10 | 10 | 10 | 10 |
| 1.0% EDC XL-Powder | 10 | 0 | 0 | 0 | 0 | 0 | 3 | 5 | 5 | 9 | 10 | 10 | 10 | 10 | 10 |
| Promogran ™ | 10 | 0 | 0 | 0 | 0 | 1 | 1 | 1 | 1 | 6 | 8 | 8 | 8 | 8 | 9 |

TABLE 6

Time to respond in days

| | Day 'initiation of healing' first evident | | | | |
|---|---|---|---|---|---|
| Replicate | Control | Non-XL sponge | 0.5% EDC XL-Powder | 1.0% EDC XL-Powder | Promogran ™ |
| 1 | n/a | 12 | 12 | 6 | 5 |
| 2 | n/a | 12 | 10 | 7 | 10 |

TABLE 6-continued

| Time to respond in days | | | | | |
|---|---|---|---|---|---|
| | Day 'initiation of healing' first evident | | | | |
| Replicate | Control | Non-XL sponge | 0.5% EDC XL-Powder | 1.0% EDC XL-Powder | Promogran ™ |
| 3 | n/a | 7 | 12 | 6 | 12 |
| 4 | n/a | 14 | 10 | 12 | 10 |
| 5 | n/a | 12 | 10 | 6 | 10 |
| 6 | n/a | 14 | 12 | 10 | 10 |
| 7 | n/a | 14 | 8 | 10 | 20 |
| 8 | n/a | 16 | 10 | 10 | 12 |
| 9 | n/a | 16 | 10 | 10 | n/a |
| 10 | n/a | 14 | 12 | 7 | 10 |
| Number responding | 0 | 10 | 10 | 10 | 9 |
| n | 10 | 10 | 10 | 10 | 10 |
| % responding | 0 | 100 | 100 | 100 | 70 |
| Mean time to respond | >20 | 13.1 | 10.6 | 8.4 | 12.0 |

Application of all three Jellagen products encouraged initiation of 'neo-dermal tissue formation' within the central wound region when compared to 'film dressing only' Control treatment. Of the three Jellagen treatments investigated, 1.0% EDC crosslinked powder resulted in the most rapid 'initiation', followed by 0.5% EDC crosslinked powder—and finally non-crosslinked sponge. All three products were as effective—if not more effective—than Promogran™.

Summary of Results—Wound Histology

Figure 24:
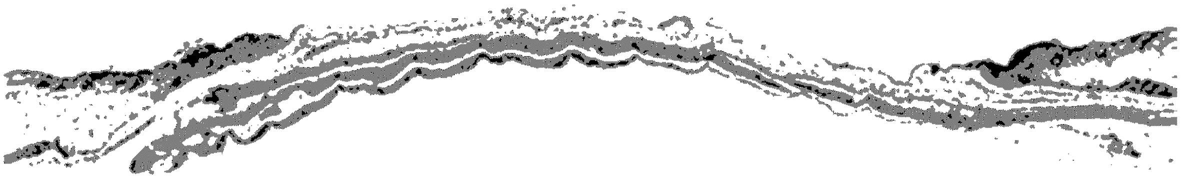
FIG. 24 shows representative examples of the histological appearance of wounds in each experimental group in a db/db (BKS.CG-m Dock 7m+/_+Leprdb/J) diabetic mouse model (approximately equally scaled). Higher magnification views of the central area of each wound can be found in FIG. 25.
Figure 24:
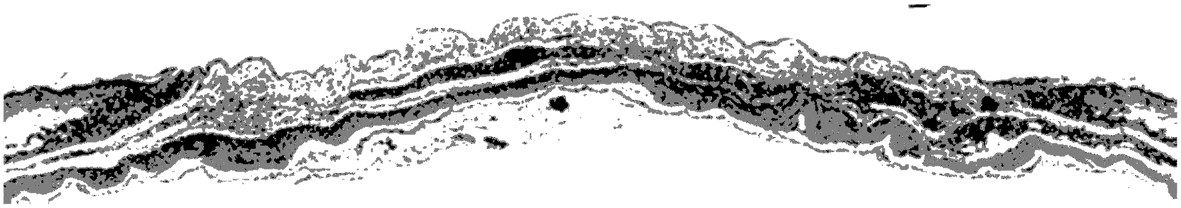
Figure 24:
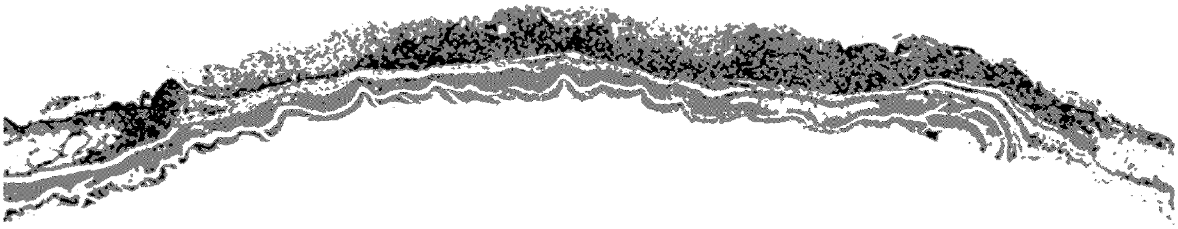
Figure 24:
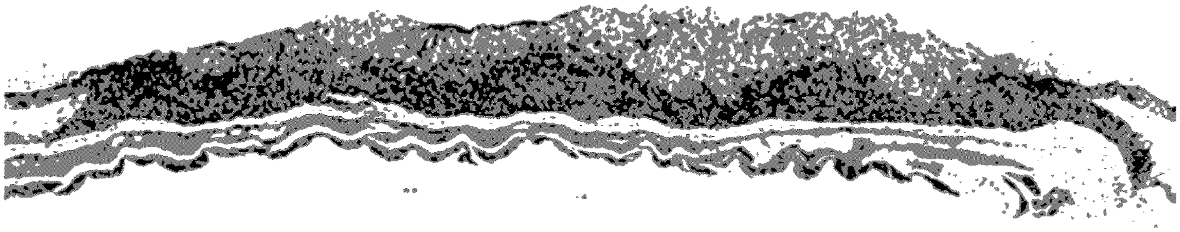
Figure 24:
Figure 25:
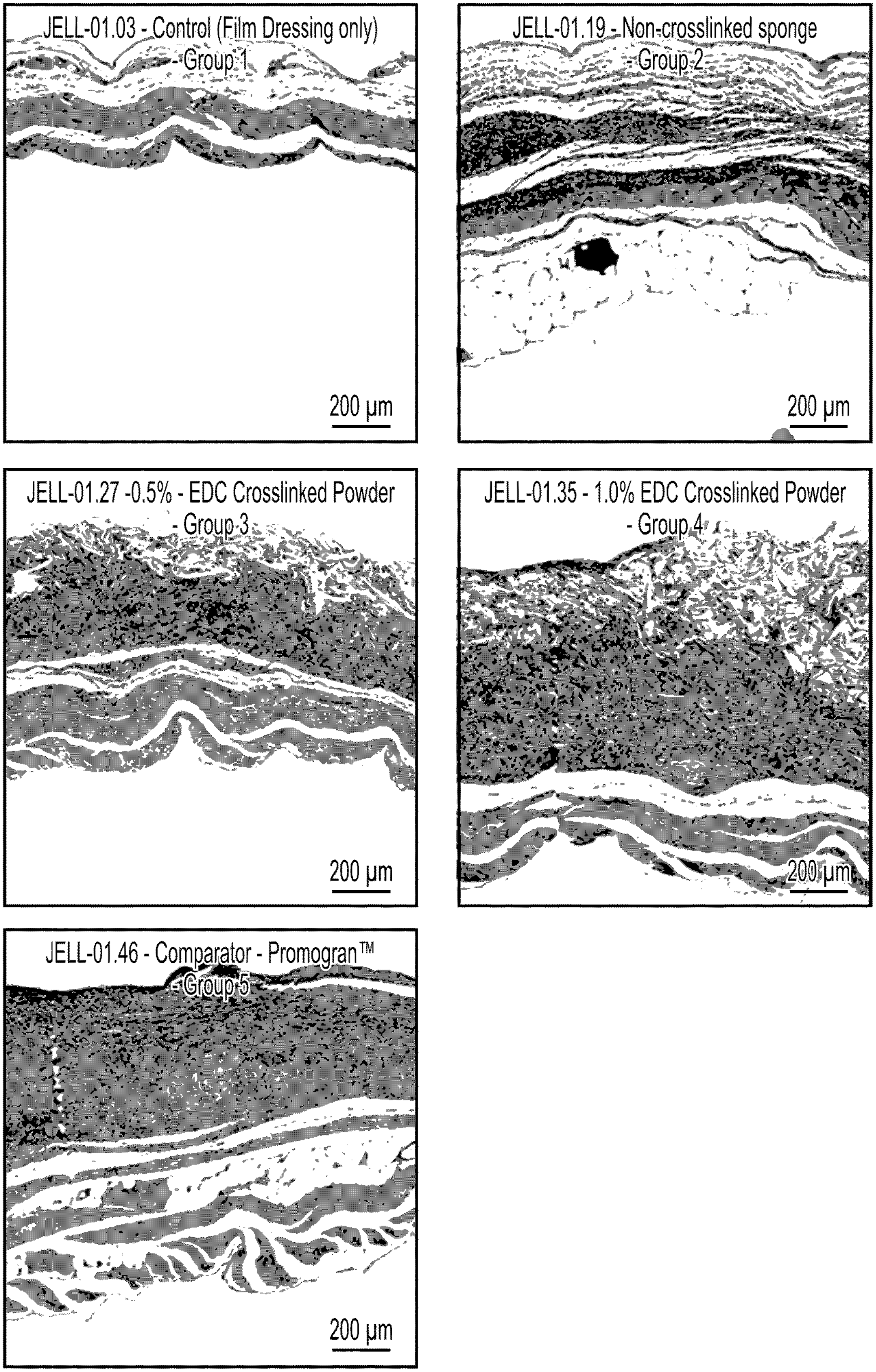
FIG. 25 shows higher magnification images of the central regions of the representative examples of the histological appearance of wounds displayed in FIG. 24.

Wound tissue, together with surrounding per-wound skin, was harvested from each animal on conclusion of the study on post-wounding day 20. Tissue samples were fixed, processed and embedded in paraffin wax. Sections (~6 μm) were taken from the centre of each wound in a cranio-caudal direction. These sections were stained with Haematoxylin and Eosin (H&E), and were digitally scanned. Representative examples of the appearance of wounds in each experimental group are displayed in FIGS. 24 and 25. The typical level of granulation tissue deposition and extent of wound re-epithelialisation for wounds in each group are described below.

Control-treated wounds displayed limited granulation tissue formation and limited re-epithelialisation (both restricted to the edges of wounds).

Application of non-crosslinked sponge resulted in in elevated granulation tissue formation and re-epithelialisation relative to Control. Granulation tissue was formed throughout the wound base, although 'quality' was found to be variable. No obvious product residue in the majority of wounds.

Application of both EDC crosslinked powders resulted in elevated granulation tissue formation with minimal re-epithelialisation in the majority of wounds. These products appeared to act as a scaffold for granulation tissue deposition—and when fully cellularised—may support re-epithelialisation. Based on gross wound images and histological appearance, these products appear not to have experienced significant degradation over the 20-day study period.

Figure 26:
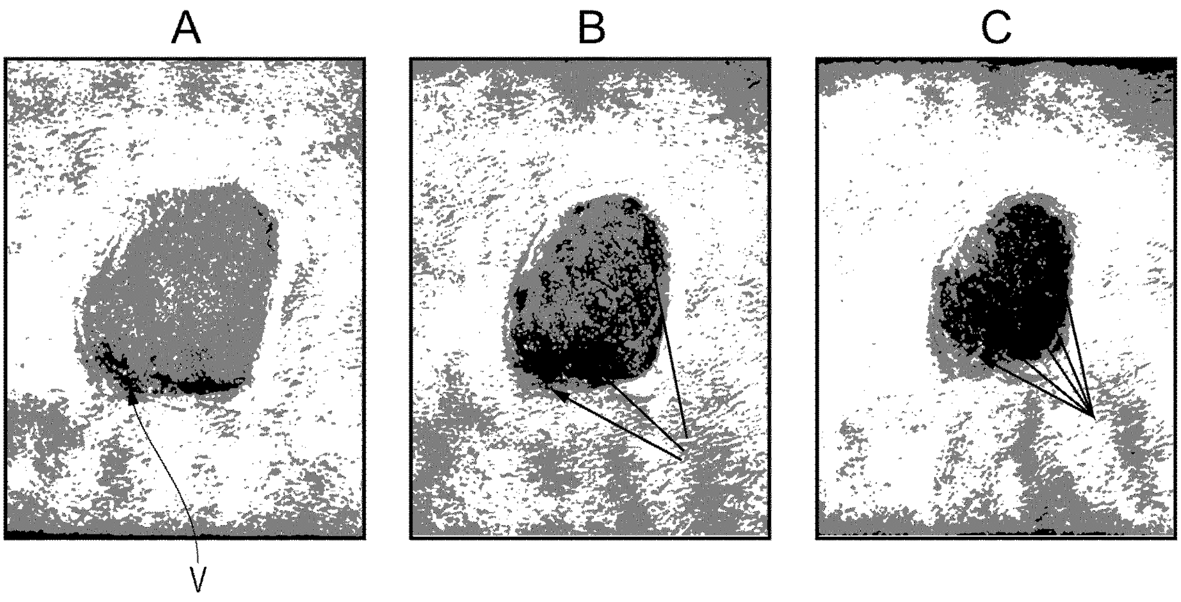
FIG. 26 shows the effect of 1% EDC crosslinked jellyfish collagen powder on: (A) day 8, (B) day 12, and (C) day 16 showing progressive vascularisation (V) of the hydrated mass.

The EDC crosslinked jellyfish collagen powders appeared to encourage the growth of new blood vessels into it from the wound edges. This was most evident with the 1.0% powder—visible macroscopically as progressive redness from the outer edges of the hydrated mass on the wound surface—and was also apparent on the histological sections (FIG. 26).

Study Outcome

All three of the Jellagen products evaluated in this study were found to have a positive impact on the healing of wounds in the db/db diabetic mouse impaired healing model.

The non-crosslinked collagen sponge promoted wound closure by promoting both contraction and re-epithelialisation, and was found to promote granulation tissue formation. The sponge material experienced extensive compaction, limited degradation and appeared not become incorporated into wound tissues.

The crosslinked powders promoted wound closure primarily by promoting the process of wound contraction—which may be explained by the ability of these products to act as a scaffold for granulation tissue formation.

Example 4—Investigation of the Impact of Jellyfish-Derived Collagen Formulations on the Healing of Full-Thickness Excisional Wounds in the db/db (BKS.Cg-m Dock7$^{m}$+/+Lepr$^{db}$/J) Diabetic Mouse Aim To investigate the impact of three Jellyfish-derived collagen formulations on wound healing in the BKS.Cg-m Dock7m+/+Leprdb/J (db/db) diabetic mouse—a model of delayed cutaneous wound healing.

Procedure

Materials under test:

Cross-linked jellyfish collagen sponge (Jellagen). Made in 24-well plates using 500 μL AMY2 (4.5 mg/mL). 1% EDC cross-linked $CHCl_3$ sterile. DOM October 2020. Sponges to be cut to wound size.

Micronised 1% EDC* cross-linked jellyfish collagen powder (Jellagen)—$CHCl_3$ sterile (individual wound aliquots of ~2.5 mg).

Micronised thiolated jellyfish collagen powder (Jellagen)—$CHCl_3$ sterile (individual wound aliquots of ~2.5 mg).

Comparator: Integra® Flowable Wound Matrix (Integra Lifesciences Inc. Princeton, USA). Product Code: FDR 301, Lot: 4679547, Expiry 30/09/2021.

BKS.Cg-m Dock7m+/+Leprdb/J Diabetic Mouse Model

The methods followed are briefly outlined below.

Diabetic mice (BKS.Cg-m Dock7m+/+Leprdb/J, Jackson Labs, Bar Harbour, ME, USA) were brought into the UK aged approximately 9-10 weeks and were allowed to acclimate for one week prior to the start of the study. Animals were maintained according to UK Home Office regulations and the specific requirements of diabetic animals. Animals were randomly allocated to 5 treatment groups (Table 7).

TABLE 7

Experimental Groups

| Tx Group | Treatment (FD = Film Dressing) | Application (days) | Animal Codes Day 35 Harvest | Day 63 | "n" |
|---|---|---|---|---|---|
| 1 | Film Dressing Only (Negative Control) | 0, 4, 8, 12 & 16 | JELL-02.01 to 02.08 | JELL-02.09 to 02.12 | 12 |
| 2 | Crosslinked collagen sponge (Jellagen) | 0, 4, 8, 12 & 16 | JELL-02.13 to 02.20 | JELL-02.21 to 02.24 | 12 |
| 3 | Micronized 1.0% EDC cross-linked collagen powder (Jellagen) + FD | Day 0 only | JELL-02.25 to 02.32 | JELL-02.33 to 02.36 | 12 |
| 4 | Micronized thiolated collagen powder + FD | Day 0 only | JELL-02.37 to 02.44 | JELL-02.44 to 02.48 | 12 |
| 5 | Integra ® Flowable Wound Matrix + FD | Day 0 only | JELL-02.49 to 02.56 | JELL-02.57 to 02.60 | 12 |

Briefly, mice were anaesthetised using isofluorane and air, and their dorsal flank skin was clipped and cleansed according to protocol. A single standardised full-thickness wound (10 mm×10 mm) was created on the left dorsal flank approximately 5 mm from the spine. Wounds were cleaned with sterile saline-soaked gauze swabs and dried with sterile gauze. 15 μL of sterile physiological saline was then applied to the surface of each wound. The materials under test were then applied directly to the surface of saline-moistened wounds.

On days of reapplication (see Table 7 above), animals were re-anaesthetised, their film dressings and any free debris removed, and their wounds (and marginal skin) were gently cleaned using sterile saline-soaked gauze (without disturbing any existing products within the wound). Wounds were then photographed not shown), moistened with 15 μl of sterile physiological saline, and products re-applied to wounds in selected groups on selected days. After product re-application (where indicated), wounds were re-dressed with Tegaderm™ Film dressing, and animals were allowed to recover in a warmed environment (~35° C.). Wounds were digitally photographed together with a calibration/identity plate on immediately after wounding and post-wounding days 4, 8, 12, 16, 20, 24, 28, 35, 42, 49, 56, and 63.

At post wounding day 35, 8 animals from each group were sacrificed. All remaining animals were culled on post-wounding day 63.

Summary of Results—Wound Closure

Figure 27:
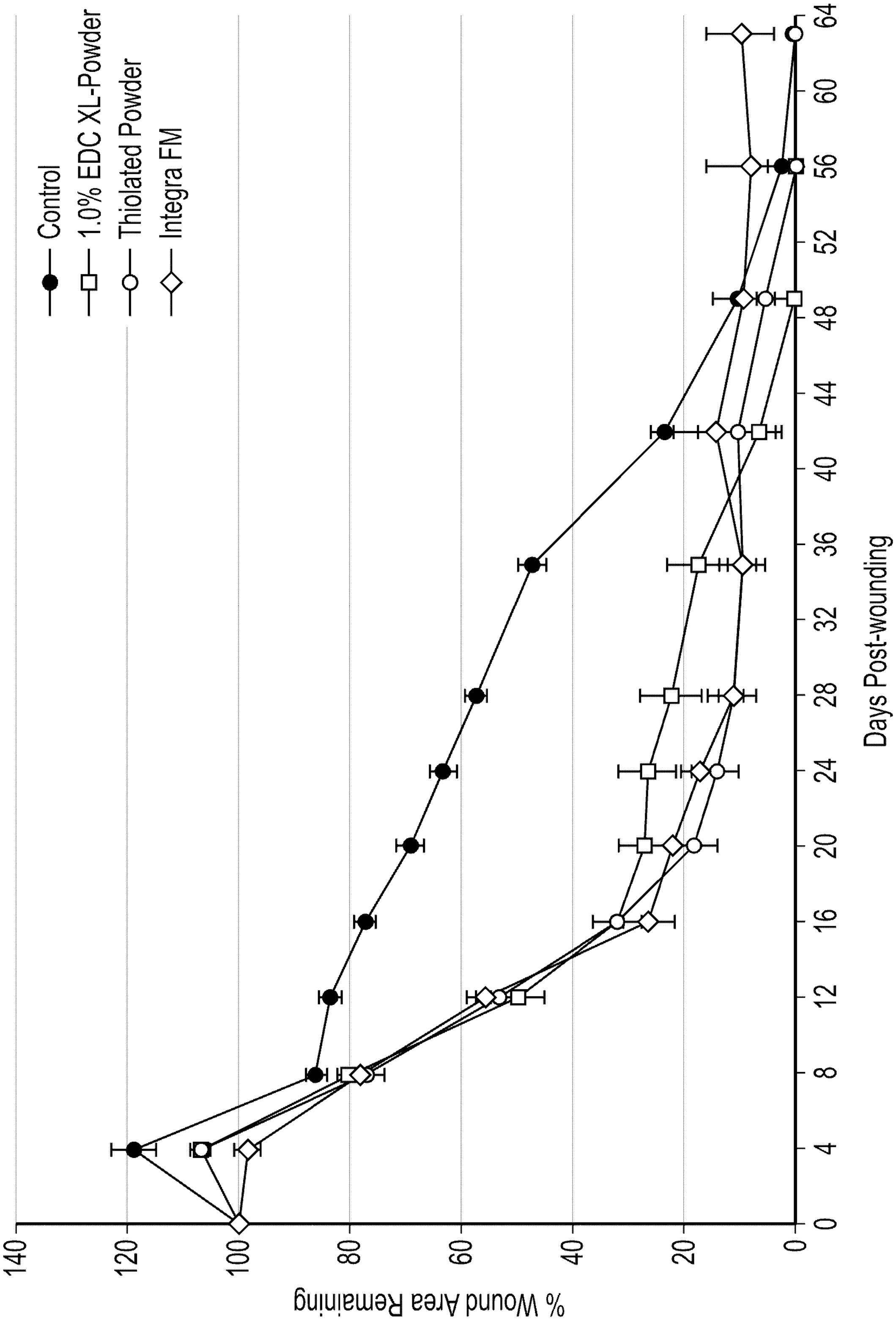
FIG. 27 shows wound closure profiles of all the treatment groups as "% wound area remaining with time" data in a db/db (BKS.CG-m Dock 7m+/_+Leprdb/J) diabetic mouse model. The experiments were carried out as described in Example 4 and the test groups were: Control (film dressing only); 1.0% EDC XL-powder; Thiolated powder; Integra® Flowable Matrix. Results are shown for all animals in the test groups—mean±s.e.m. (n=12 to day 35, n=4 days 42 to 63).

Each wound was digitally photographed, along with an identification/calibration plate, immediately after injury and subsequently on days 4, 8, 12, 16, 20, 24, 28, 35, 42, 49, 56, and 63. For a given wound at a given time point, wound closure was expressed as the percentage wound area remaining relative to the initial wound area immediately after injury (i.e. day 0). Mean percentage wound area remaining data for all treatment groups are shown in FIG. 27. It was not always possible to obtain clear visualisation of the wound edges in the XL-sponge treatment group due to the presence of the sponge and so the values for that test group are not included in FIG. 27.

Figure 28:
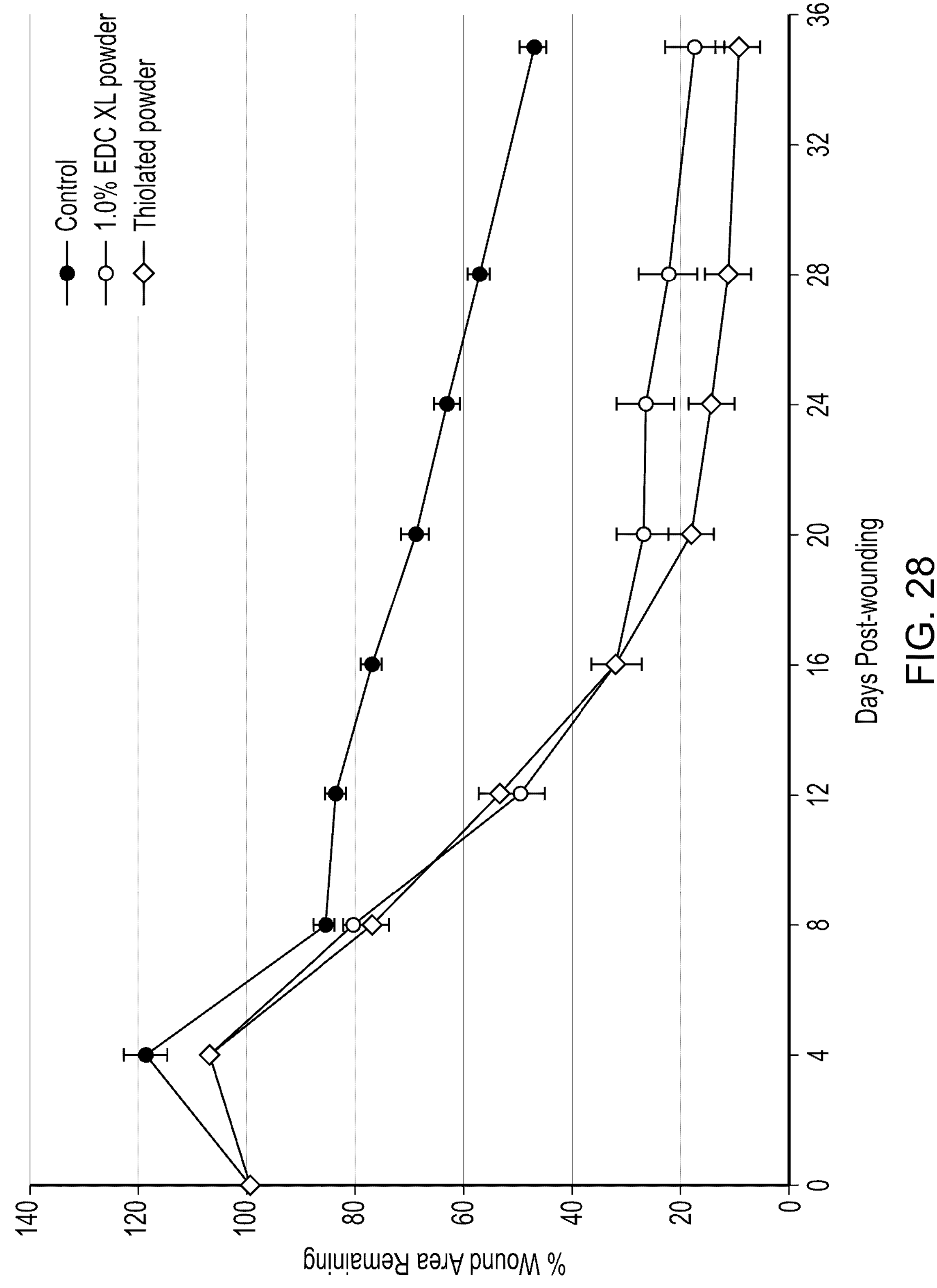
FIG. 28 shows wound closure profiles for all jellyfish collagen treatment groups tested as "% wound area remaining with time" data in a db/db (BKS.CG-m Dock 7m+/_+Leprdb/J) diabetic mouse model. The experiments were carried out as described in Example 4. Results are shown for all animals in the test groups—mean±s.e.m. (n=12 to day 35).
Figure 29:
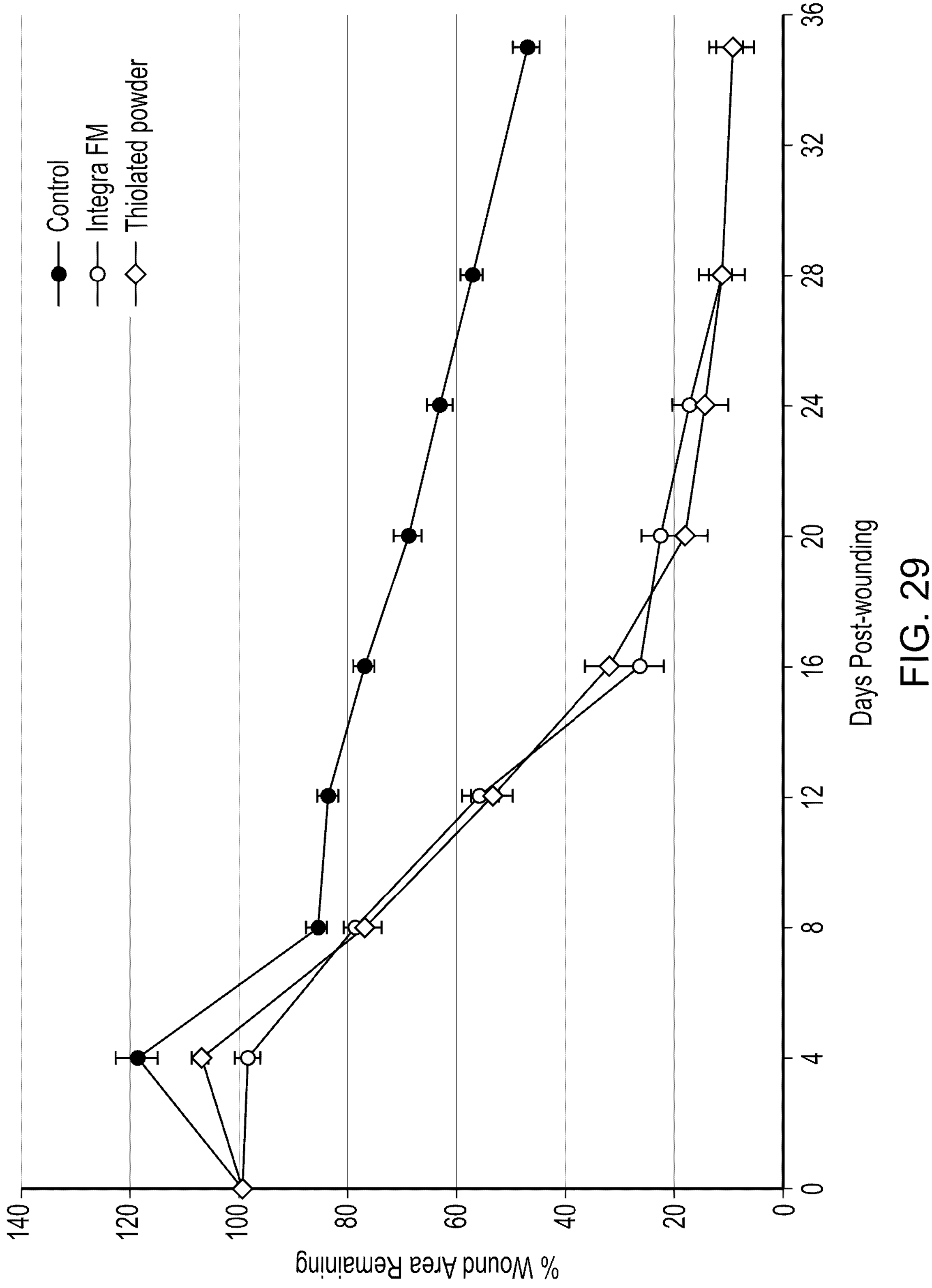
FIG. 29 shows wound closure profiles for the thiolated powder and Integra FM treatment groups as "% wound area remaining with time" data in a db/db (BKS.CG-m Dock 7m+/_+Leprdb/J) diabetic mouse model. The experiments were carried out as described in Example 4. Results are shown for all animals in the test groups—mean±s.e.m. (n=12 to day 35).

When wound closure (in terms of change in '% open wound area' with time) was considered, the following was observed:

- All of the treatments considered were found to increase closure compared to 'film dressing only' Control treatment up to at least day 35 post-wounding. Some regression of wound healing was noted in all groups between days 35 and 63 with the exception of the Thiolated Powder and control treatment groups.
- Each of the Jellagen products evaluated were found to significantly promote wound closure compared 'film dressing only' Control treatment from at least day 12 onwards (day 4 for 1.0% EDC XL-powder and thiolated powder) (FIG. 27).
- When the two Jellagen products were compared, wounds in receipt of the thiolated powder demonstrated the greatest response up to day 35 (where n=12), followed by 1% EDC XL-powder (FIG. 28). No significant differences were noted at the later time points (after day 35) (where n=4).
- When the thiolated powder was compared to the Integra product, very similar closure profiles were observed to day 35 (n=12) (FIG. 29) and marginally increased closure was observed for the thiolated powder from day 42 to 63 (n=4) (FIG. 27).

Summary of Results—Wound Contraction

Contraction is the centripetal movement of the wound margins, due to the compaction of granulation tissue within the "body" of the wound. The "compactional" forces that drive this process, are thought to reside in cells of the fibroblast lineage. In this study, percentage contraction was calculated as:

$$\%\ \text{contraction} = \frac{\text{The area defined by the boundary of normal dermis and the}}{\text{The original wound area (day 0)}} \times 100$$

Wounds on non-diabetic mice close predominantly by contraction, while those on diabetic mice (such as those used in this study) have a significantly reduced ability to contract (possibly due to impoverished granulation tissue formation). As a result, untreated wounds on diabetic animals tend to close by re-epithelialisation to a greater extent than those on non-diabetic animals. An observation of enhanced contraction suggests improvement in granulation tissue function, which may in turn be explained by an increase in the amount of granulation tissue formed, an increase in the speed at which it is formed, or increased contractile capacity of the tissue. Mean percentage wound contraction data for all treatment groups are shown in FIG. 30.

When the impact of treatment on wound contraction was considered, the following was observed:

- All of the treatments considered were found to significantly increase wound contraction compared to 'film dressing only' Control treatment up to at least day 35 post-wounding.

Figure 30:
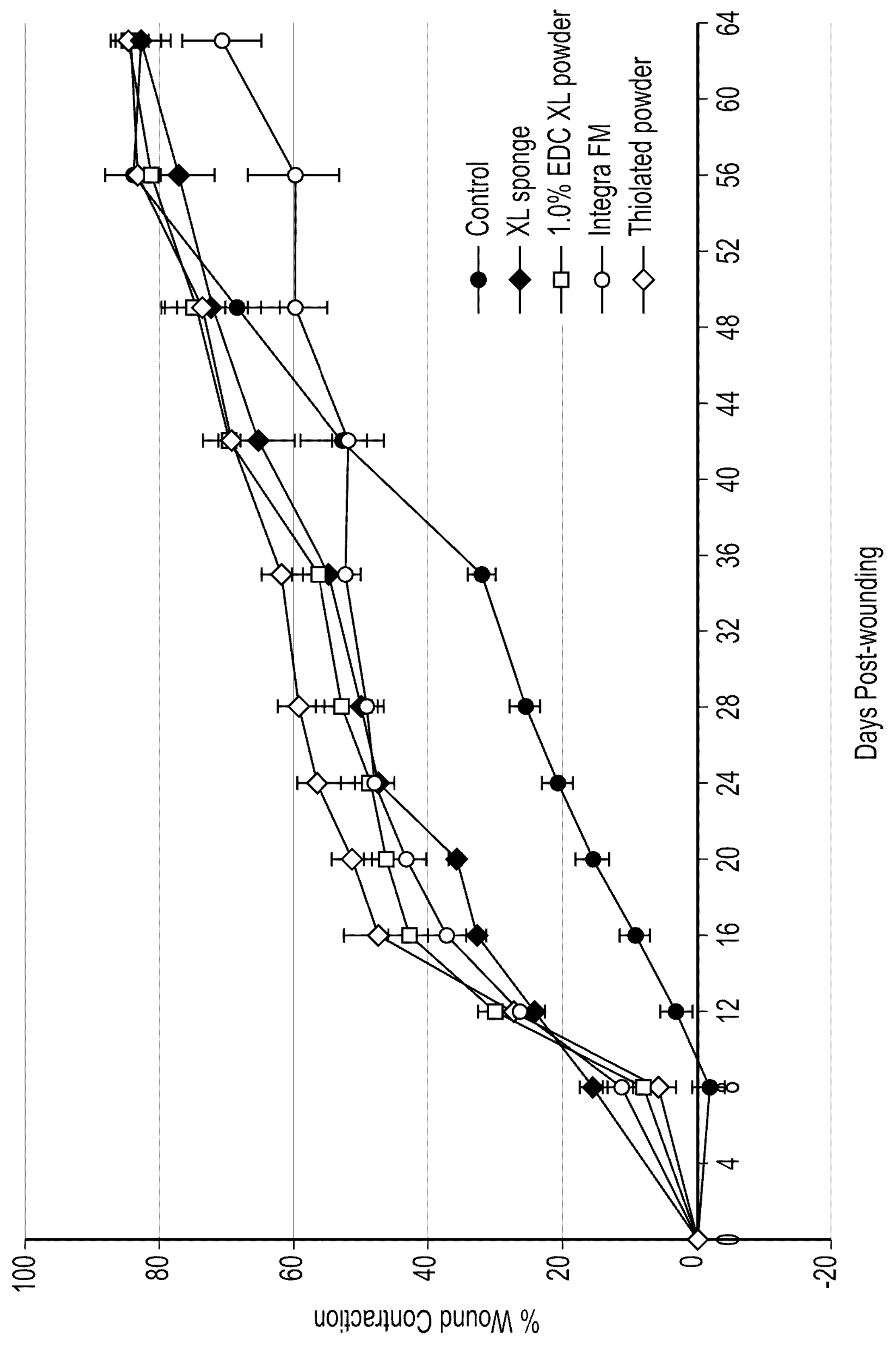
FIG. 30 shows wound contraction profiles of the treatment groups as "% wound contraction" data in a db/db (BKS.CG-m Dock 7m+/_+Leprdb/J) diabetic mouse model. The experiments were carried out as described in Example 4 and the test groups were: Control (film dressing only); XL-sponge; 1.0% EDC XL-powder; Thiolated powder; Integra® Flowable Matrix. Results are shown for all animals in the test groups—mean±s.e.m. (n=12 to day 35, n=4 days 42 to 63).

Each of the three Jellagen products evaluated were found to significantly promote wound contraction compared 'film dressing only' Control treatment from at least day 12 onwards (day 4 for XL-sponge, day 8 for 1% EDC XL-powder, and near-significance at day 8 for thiolated powder) (FIG. 30).

Figure 31:
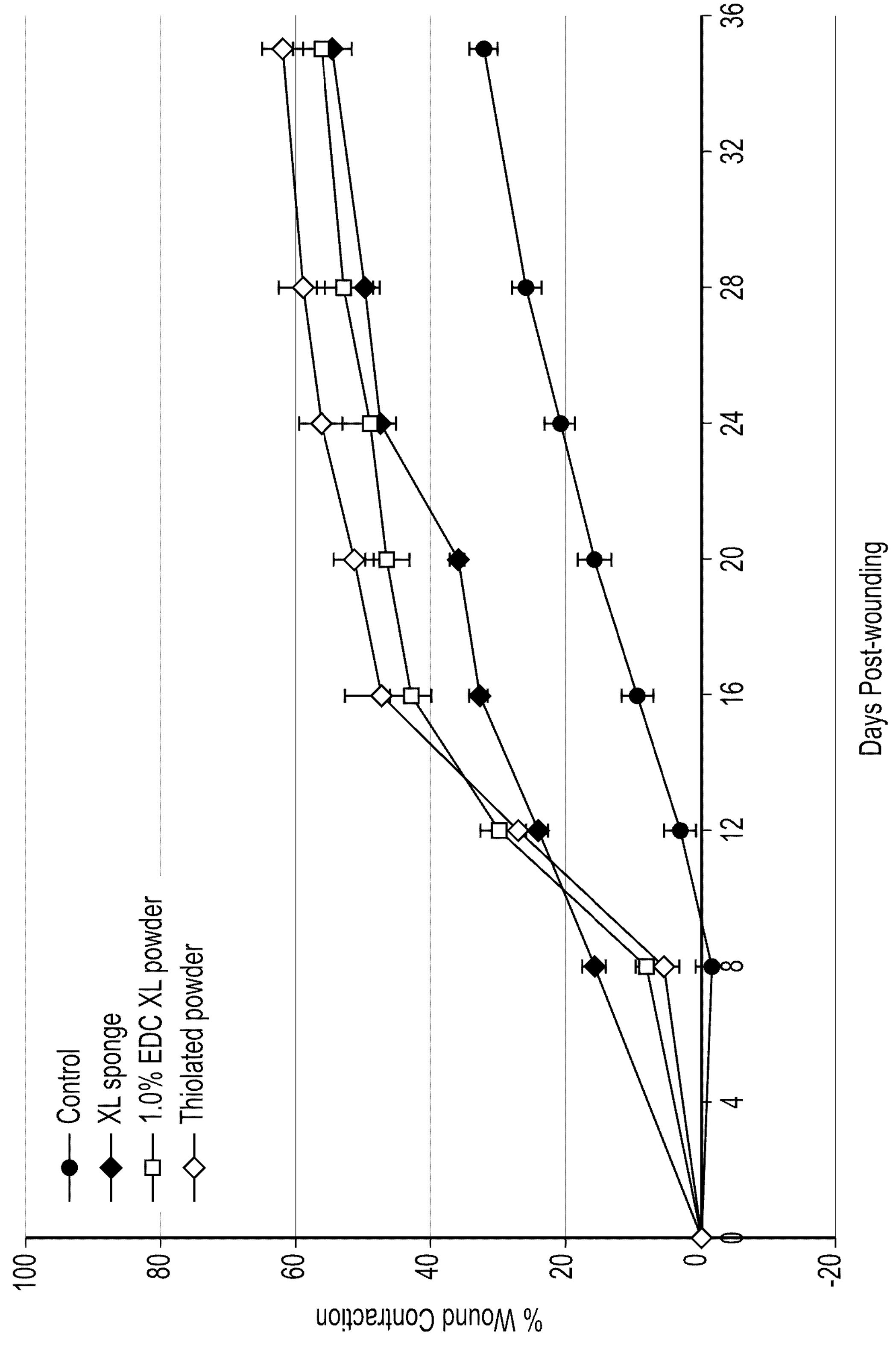
FIG. 31 shows wound contraction profiles for all jellyfish collagen treatment groups tested as "% wound contraction" data in a db/db (BKS.CG-m Dock 7m+/_+Leprdb/J) diabetic mouse model. The experiments were carried out as described in Example 4. Results are shown for all animals in the test groups—mean±s.e.m. (n=12 to day 35).

When the three Jellagen products were compared (FIG. 31), wounds in receipt of the thiolated powder demonstrated the greatest contraction to day 35 (where n=12), with XL-sponge and 1% EDC XL-powder promoting slightly lower contraction that was comparable to the Integra product (FIG. 30).

Figure 32:
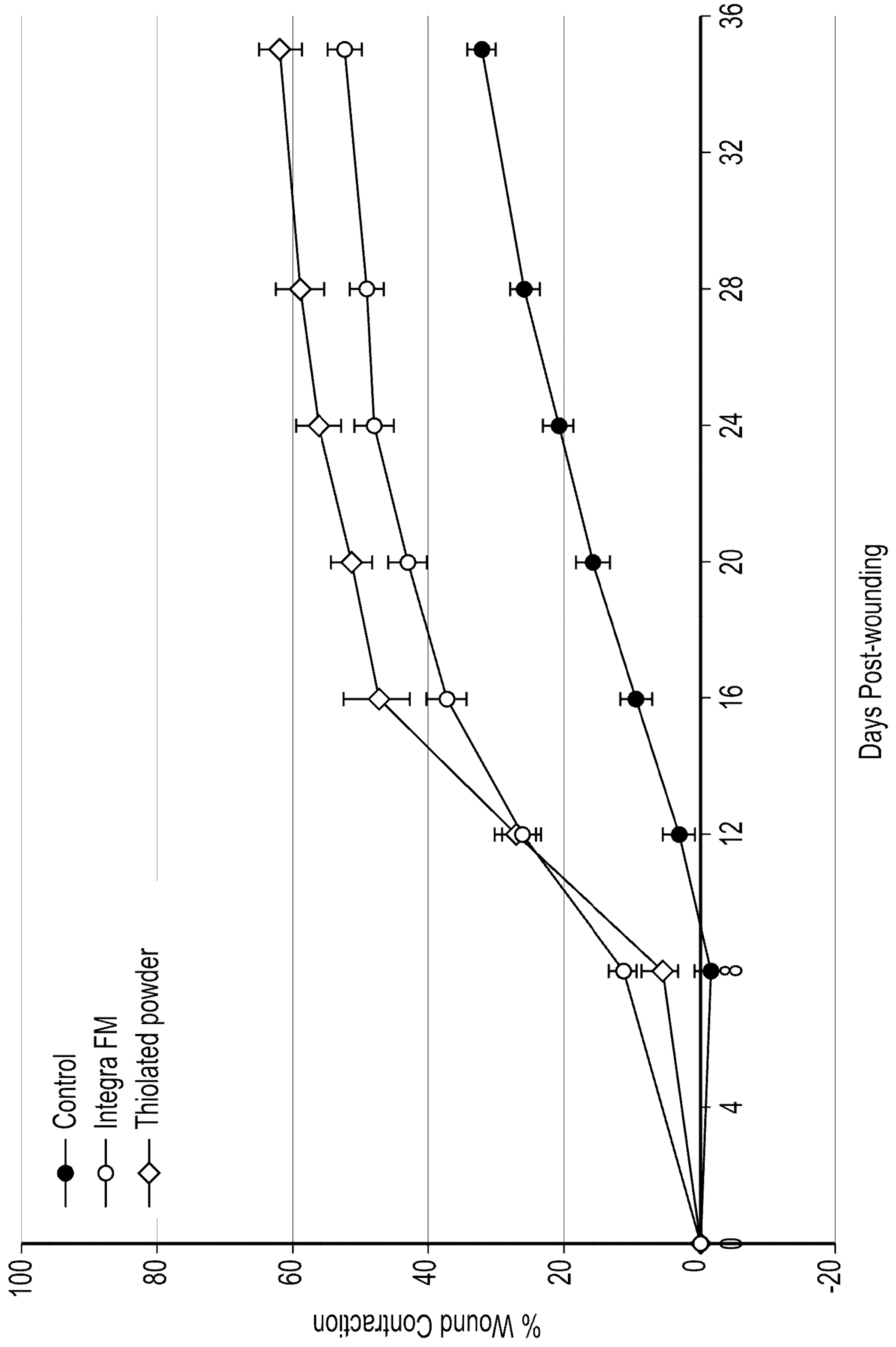
FIG. 32 shows wound contraction profiles for the thiolated powder and Integra FM treatment groups as "% wound contraction" data in a db/db (BKS.CG-m Dock 7m+/_+ Leprdb/J) diabetic mouse model. The experiments were carried out as described in Example 4. Results are shown for all animals in the test groups—mean±s.e.m. (n=12 to day 35).

When the thiolated powder was compared to the Integra product (FIG. 32), increased contraction was observed for the thiolated powder, reaching statistical significance on days 20, and 28 to 42 ($p \leq 0.029$), with near significance on days 16 and 24 ($p=0.060$ and 0.068 respectively).

Summary of Results—Wound Re-Epithelialisation

Figure 33:
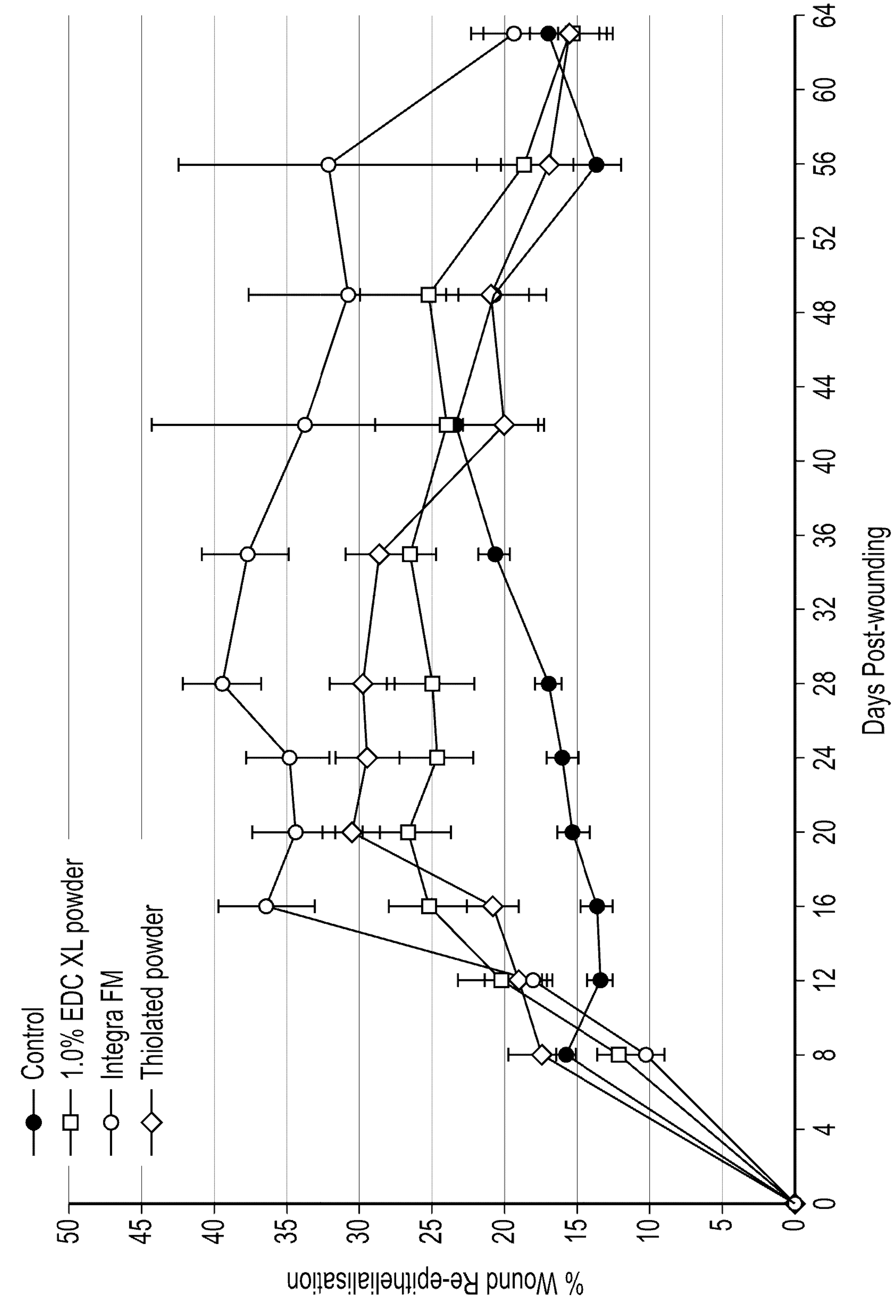
FIG. 33 shows profiles for re-epithelialisation of the wound as "% wound re-epithelialisation" that was first measurable on day 4 post-wounding between the different treatment groups in a db/db (BKS.CG-m Dock 7m+/_+ Leprdb/J) diabetic mouse model. The experiments were carried out as described in Example 4 and the test groups were: Control (film dressing only); 1.0% EDC XL-powder; Thiolated powder; Integra® Flowable Matrix. Results are shown for all animals in the test groups—mean±s.e.m. (n=12 to day 35, n=4 days 42 to 63).

For a given wound, at a given time point, the area of re-epithelialisation was expressed as a percentage of the original area of that wound immediately after injury. Mean percentage wound re-epithelialisation data for all treatment groups are described in Table 4 (below) and shown in FIG. 33. It was not possible to accurately measure re-epithelialisation on wounds in receipt of the XL-sponge whilst the sponge remained in place and so the results from that treatment are not included in FIG. 33.

When the impact of treatment on wound re-epithelialisation was considered, the following was observed:

All of the treatments considered were found to increase wound re-epithelialisation compared to 'film dressing only' Control treatment up to at least day 35 post-wounding.

Both the Jellagen 1% EDC XL-powder and Jellagen thiolated powder products were found to significantly promote wound contraction compared 'film dressing only' Control from at least day 16 onwards. Specifically, the wounds in receipt of the thiolated powder demonstrated significantly increased wound re-epithelialisation compared to control wounds from day 12 to day 35 ($p \leq 0.007$) and wounds in receipt of the 1% EDC XL-powder product demonstrated significantly increased wound re-epithelialisation compared to control wounds from day 16 to day 35 ($p \leq 0.028$), with near significance on day 12 ($p=0.052$).

Figure 34:
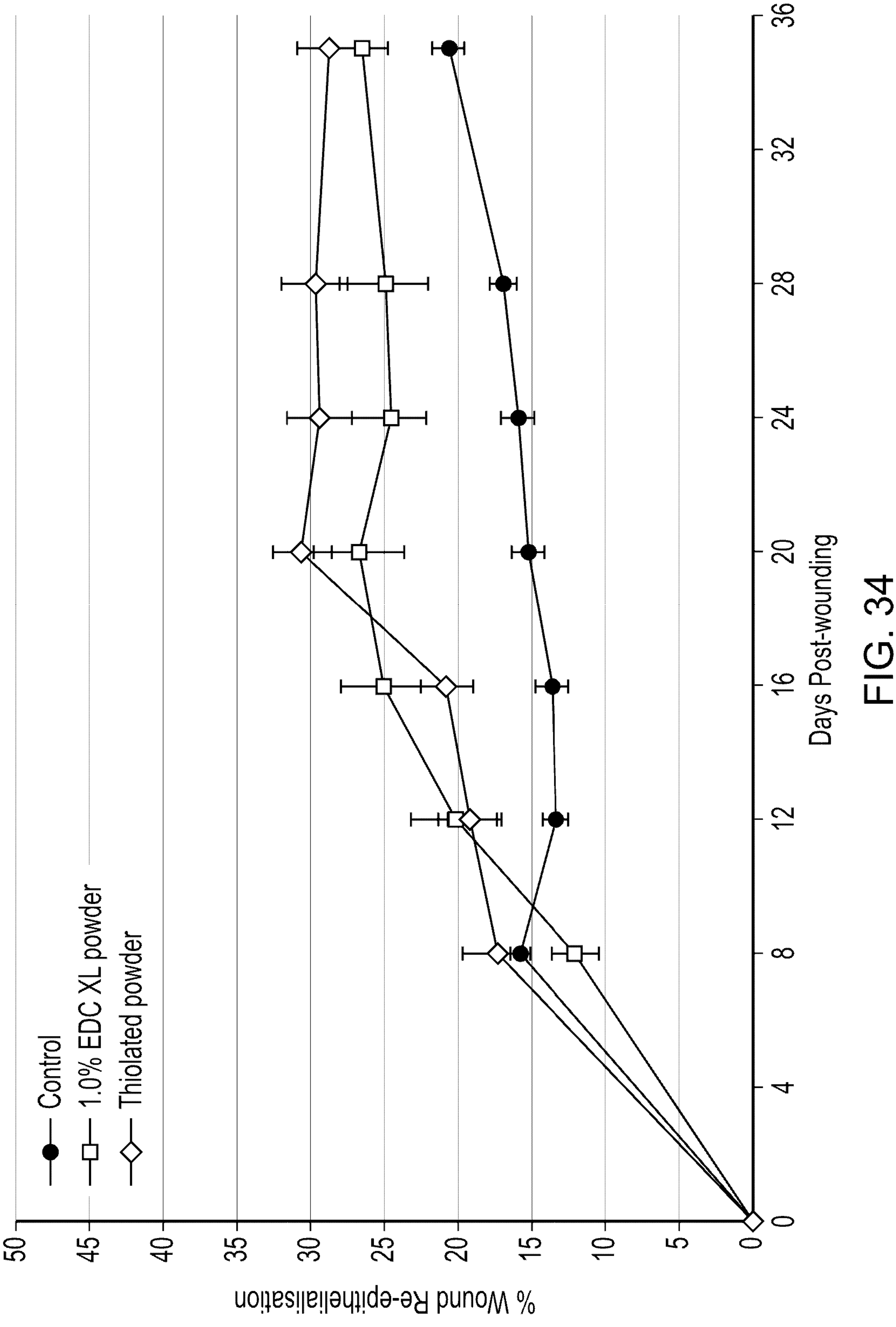
FIG. 34 shows profiles for re-epithelialisation of the wound for all jellyfish collagen treatment groups tested as "% wound re-epithelialisation" that was first measurable on day 4 post-wounding between the different treatment groups in a db/db (BKS.CG-m Dock 7m+/_+Leprdb/J) diabetic mouse model. The experiments were carried out as described in Example 4. Results are shown for all animals in the test groups—mean±s.e.m. (n=12 to day 35).
Figure 35:
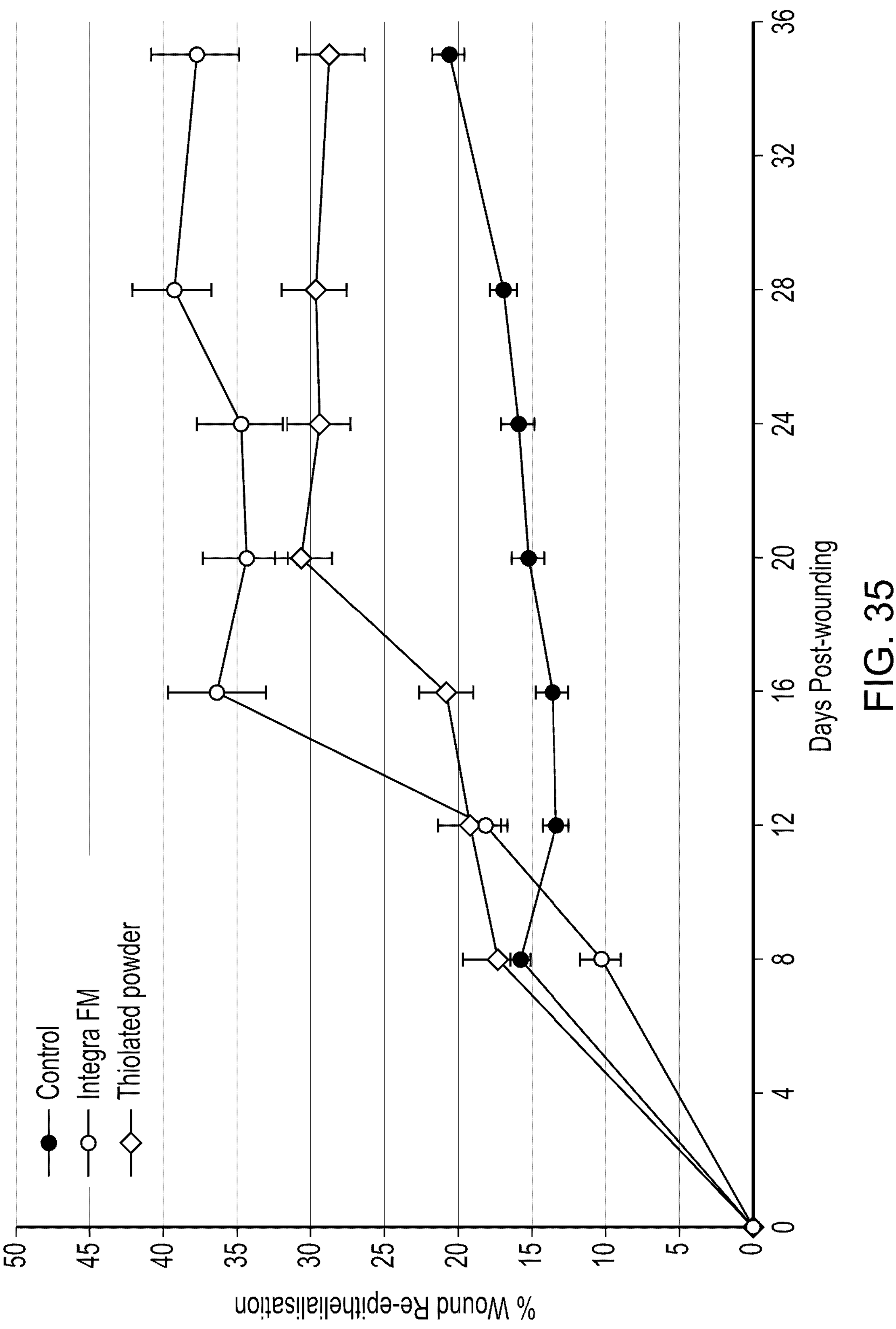
FIG. 35 shows profiles for re-epithelialisation of the wound for the thiolated powder and Integra FM treatment groups tested as "% wound re-epithelialisation" that was first measurable on day 4 post-wounding between the different treatment groups in a db/db (BKS.CG-m Dock 7m+/_+Leprdb/J) diabetic mouse model. The experiments were carried out as described in Example 4. Results are shown for all animals in the test groups—mean t s.e.m. (n=12 to day 35).

When the 1% EDC XL-powder and thiolated powder were compared (FIG. 34), wounds in receipt of the thiolated powder demonstrated the greatest re-epithelialisation to day 35 (where n=12), with 1% EDC XL-powder promoting slightly lower re-epithelialisation.

When the thiolated powder was compared to the Integra product (FIG. 34), the Integra product generally showed slightly increased levels of re-epithelialisation to day 35 post-wounding, reaching significance on days 16, 28, and 35 ($p \leq 0.039$). However, the thiolated powder showed significantly increased re-epithelialisation on day 8 post-wounding ($p=0.010$).

The invention claimed is:

1. A method for the treatment of a wound, the method comprising administering a composition comprising thiolated jellyfish collagen to a human or non-human animal in need thereof to effectively treat the wound in the subject.

2. The method of claim 1, wherein the jellyfish collagen is not in a hydrolysate form.

3. The method of claim 1, wherein the jellyfish collagen is in its atelo form or its telo form.

4. The method of claim 1, wherein the jellyfish collagen is cross-linked.

5. The method of claim 1, wherein the source of the jellyfish collagen is from the sub-phylum Scyphozoa.

6. The method of claim 5, wherein the source of the jellyfish collagen is selected from the group consisting of *Rhizostomas pulmo, Rhopilema esculentum, Rhopilema nomadica, Stomolophus meleagris, Aurelia* sp., *Cassiopea andromeda, Nemopilema nomurai*, and combinations thereof.

7. The method of claim 1, wherein the jellyfish collagen is in a form selected from the group consisting of a hydrogel, a paste, a micronized powder, a membrane, a scaffold, a solution, a sponge matrix, a nano-fibre electrospun matrix, and lyophilized.

8. The method of claim 1, wherein the composition further comprises a growth factor or an antimicrobial compound.

9. The method of claim 8, wherein the growth factor is selected from the group consisting of Platelet Rich Plasma (PRP), Epithelial Growth Factor 38 (EGF), Transforming Growth Factor-Beta (TGF-B, TGF-B2, TGF-B3), Hepatocyte Growth Factor (HGF), Keratinocyte Growth Factor (KGF), Granulocyte-Monocyte Colony Stimulating Growth Factor, Platelet Derived Growth Factor, Insulin-like Growth Factor 1 (IGF1), basic Fibroblast Growth Factor (bFGF), Vascular 5 Endothelial Growth Factor (VEGF), and combinations thereof.

10. The method of claim 8, wherein the antimicrobial compound is selected from the group consisting of nano silver, penicillin, ofloxacin, tetracycline, aminoglycosides, erythromycin, gentamycin, flucloxacillin, clarithromycin, doxycycline, gentamicin, metronidazole, co-amoxiclav, co-trimoxazole (in penicillin), ceftriaxone, piperacillin with tazobactam, clindamycin, ciprofloxacin, vancomycin, teicoplanin, linezolid, and combinations thereof.

11. The method of claim 1, wherein the jellyfish collagen is formulated for topical application to the wound.

12. The method of claim 1, wherein said jellyfish collagen is administered at a dose from 0.01 g/L to 200 g/L, per administration.

13. The method according to claim 1, wherein the composition further comprises a pharmaceutically acceptable excipient or carrier.

14. The method according to claim 1, wherein the composition further comprises a pharmaceutically active ingredient.

15. The method of claim 14, wherein the pharmaceutically active ingredient is lidocaine.

16. The method of claim 1, wherein the wound to be treated is selected from the group consisting of a pressure sore, a transplant site, a surgical wound, an ulcer, a thermal burn, a chemical burn, an electrical burn, a laceration, an abrasion, a puncture, an avulsion, a seroma, and a hematoma.

17. The method of claim 1, wherein the jellyfish collagen is in the form of a micronized powder or a collagen 3D sponge scaffold.

18. The method according to claim 17, wherein the micronized powder has a particle size of 1 μm to 1000 μm.

19. The method according to claim 1, wherein the thiolated jellyfish collagen is administered to the human.

* * * * *